(12) United States Patent
Wilson et al.

(10) Patent No.: US 12,134,641 B2
(45) Date of Patent: Nov. 5, 2024

(54) METHODS AND COMPOSITION FOR NEUTRALIZATION OF INFLUENZA

(71) Applicant: The University of Chicago, Chicago, IL (US)

(72) Inventors: Patrick Wilson, Chicago, IL (US); Yaoqing Chen, Chicago, IL (US); Haley L. Dugan, Chicago, IL (US)

(73) Assignee: The University of Chicago, Chicago, IL (US)

( * ) Notice: Subject to any disclaimer, the term of this patent is extended or adjusted under 35 U.S.C. 154(b) by 0 days.

(21) Appl. No.: 18/335,879

(22) Filed: Jun. 15, 2023

(65) Prior Publication Data

US 2024/0002478 A1    Jan. 4, 2024

Related U.S. Application Data

(62) Division of application No. 16/977,327, filed as application No. PCT/US2019/020223 on Mar. 1, 2019, now Pat. No. 11,702,464.

(60) Provisional application No. 62/637,508, filed on Mar. 2, 2018.

(51) Int. Cl.
| | |
|---|---|
| *C07K 16/10* | (2006.01) |
| *A61K 39/42* | (2006.01) |
| *A61K 45/06* | (2006.01) |
| *A61P 31/16* | (2006.01) |
| *A61K 39/00* | (2006.01) |

(52) U.S. Cl.
CPC .......... *C07K 16/1018* (2013.01); *A61K 39/42* (2013.01); *A61K 45/06* (2013.01); *A61P 31/16* (2018.01); *A61K 2039/505* (2013.01); *C07K 2317/565* (2013.01); *C07K 2317/76* (2013.01); *C07K 2317/92* (2013.01)

(58) Field of Classification Search
None
See application file for complete search history.

(56) References Cited

U.S. PATENT DOCUMENTS

| | | | |
|---|---|---|---|
| 4,676,980 | A | 6/1987 | Segal et al. |
| 4,816,567 | A | 3/1989 | Cabilly et al. |
| 4,831,175 | A | 5/1989 | Gansow et al. |
| 4,946,778 | A | 8/1990 | Ladner et al. |
| 5,260,203 | A | 11/1993 | Ladner et al. |
| 2014/0046039 | A1* | 2/2014 | Ahmed ............ A61P 31/16 530/389.4 |
| 2014/0331366 | A1 | 11/2014 | Yusibov et al. |
| 2015/0030607 | A1 | 1/2015 | Jiang et al. |
| 2016/0176953 | A1 | 6/2016 | Purcell Ngambo et al. |
| 2016/0376347 | A1 | 12/2016 | Saelens et al. |

FOREIGN PATENT DOCUMENTS

| | | |
|---|---|---|
| WO | WO 88/01649 | 3/1988 |
| WO | WO 2010/037046 | 4/2010 |
| WO | WO 2016/118937 | 7/2016 |
| WO | WO 2016/124682 | 8/2016 |

OTHER PUBLICATIONS

Abed et al., Divergent evolution of hemagglutinin and neuraminidase genes in recent influenza A:H3N2 viruses isolated in Canada. J Med Virol. Aug. 2002;67(4):589-95.
Air. Influenza neuraminidase. Influenza Other Respir Viruses. Jul. 2012;6(4):245-56.
Anderson et al., Natural and directed antigenic drift of the H1 influenza virus hemagglutinin stalk domain. Nov. 6, 2017;7(1):14614. 19 pages.
Andrews et al., Immune history profoundly affects broadly protective B cell responses to influenza. (2015). Immune history profoundly affects broadly protective B cell responses to influenza. Sci Transl Med. Dec. 2, 2015;7(316):316ra192. 26 pages.
Angeletti et al., Is It Possible to Develop a "Universal" Influenza Virus Vaccine? Outflanking Antibody Immunodominance on the Road to Universal Influenza Vaccination. Cold Spring Harb Perspect Biol. Jul. 2, 2018;10(7):a028852. 11 pages.
Arnon et al., "Monoclonal Antibodies for Immunotargeting of Drugs in Cancer Therapy," in Monoclonal Antibodies and Cancer Therapy. 1985. pp. 243-256.
Baldwin et al., Analysis, results, and future prospective of the therapeutic use of radiolableded antibody in cancer therapy. Academic Press, New York, 1985, pp. 303-316.
Benton et al., Biophysical measurement of the balance of influenza a hemagglutinin and neuraminidase activities. J Biol Chem. Mar. 6, 2015;290(10):6516-21.
Brett et al., Variation in the divalent cation requirements of influenza A virus N1 neuraminidases. J Biochem. Mar. 2006;139(3):439-47.
Chen et al., Influenza Infection in Humans Induces Broadly Cross-Reactive and Protective Neuraminidase-Reactive Antibodies. Cell. Apr. 5, 2018;173(2):417-429.e10.
Chothia et al., Canonical structures for the hypervariable regions of immunoglobulins. J Mol Biol. Aug. 20 , 1987;196(4):901-17.
Chothia et al., Conformations of immunoglobulin hypervariable regions. Nature. Dec. 21-28, 1989;342(6252):877-83.
Clackson et al., Making antibody fragments using phage display libraries. Nature. Aug. 15, 1991;352(6336):624-8.
Clements et al., Serum and nasal wash antibodies associated with resistance to experimental challenge with influenza A wild-type virus. J Clin Microbiol. Jul. 1986;24(1):157-60.

(Continued)

*Primary Examiner* — Shanon A. Foley
*Assistant Examiner* — Myron G Hill
(74) *Attorney, Agent, or Firm* — David W. Staple; Casimir Jones, S.C.

(57) ABSTRACT

Provided herein are anti-neuraminidase agents useful for neutralization of influenza virus infection, and methods of use and manufacture thereof. In particular, compositions comprising anti-neuraminidase agents (e.g., antibodies) that are cross-reactive with multiple influenza strains are provided, as well as methods of treatment and prevention of influenza infection therewith.

10 Claims, 24 Drawing Sheets

Specification includes a Sequence Listing.

(56) References Cited

OTHER PUBLICATIONS

Dharan, N.J., et al., Infections with oseltamivir-resistant influenza A(H1N1) virus in the United States. JAMA. Mar. 11, 2009;301(10):1034-41.
Dilillo et al., Broadly neutralizing anti-influenza antibodies require Fc receptor engagement for in vivo protection. J Clin Invest. Feb. 2016;126(2):605-10.
Doyle et al., Universal anti-neuraminidase antibody inhibiting all influenza A subtypes. Antiviral Res. Nov. 2013;100(2):567-74.
Dunand et al., Both Neutralizing and Non-Neutralizing Human H7N9 Influenza Vaccine-Induced Monoclonal Antibodies Confer Protection. Cell Host Microbe. Jun. 8, 2016;19(6):800-13.
Dunand et al., Preexisting human antibodies neutralize recently emerged H7N9 influenza strains. J Clin Invest. Mar. 2, 2015;125(3):1255-68.
Eichelberger et al., Influenza neuraminidase as a vaccine antigen. Curr Top Microbiol Immunol. 2015;386:275-99.
European Search Report for PCT/US2019/020223. mailed Mar. 4, 2022. 16 pages.
Flannery et al., Interim Estimates of 2016-17 Seasonal Influenza Vaccine Effectiveness—United States, Feb. 2017. MMWR Morb Mortal Wkly Rep. Feb. 17, 2017;66(6):167-171.
Genentech (2016). TAMIFLU (R) (oseltamivir phosphate) prescribing. https://www.gene.com/download/pdf/tamiflu_prescribing.pdf. Downloaded Jun. 30, 2022. 29 pages.
Gulati et al., Antibody epitopes on the neuraminidase of a recent H3N2 influenza virus (A/Memphis/31/98). J Virol. Dec. 2002;76(23):12274-80.
Hellstrom et al., "Antibodies for Drug Delivery," in Controlled Drug Delivery, ed. Robinson et al. (2d ed; Marcel Dekker, Inc.), 1987. pp. 623-653.
Hudson et al., Engineered antibodies. Nat Med. Jan. 2003;9(1):129-34.
Influenza Research Database. www.fludb.org/brc/home.spg?decorator=influenza. Retrieved from the internet Jun. 30, 2022. 3 pages.
International Search Report and Written Opinion for PCT/US2019/020223, mailed Jun. 21, 2019, pp. 10.
Johansson et al., Antigen-presenting B cells and helper T cells cooperatively mediate intravirionic antigenic competition between influenza A virus surface glycoproteins. Proc Natl Acad Sci U S A. Oct. 1987;84(19):6869-73.
Johansson et al., Influenza viral neuraminidase: the forgotten antigen. Expert Rev Vaccines. Dec. 2011;10(12):1683-95.
Kabat et al. Sequences of Proteins of Immunological Interest. National Institutes of Health. 1991. TOC only. 11 pages.
Kohler et al., Continuous cultures of fused cells secreting antibody of predefined specificity. Nature. Aug. 7, 1975;256(5517):495-7.
Krammer et al., Advances in the development of influenza virus vaccines. Nat Rev Drug Discov. Mar. 2015;14(3):167-82.
Lee et al., Molecular-level analysis of the serum antibody repertoire in young adults before and after seasonal influenza vaccination. Nat Med. Dec. 2016;22(12):1456-1464.
Li et al. Pandemic H1N1 influenza vaccine induces a recall response in humans that favors broadly cross-reactive memory B cells. Proc Natl Acad Sci U S A.Jun. 5, 2012;109(23):9047-52.
Margine et al., Expression of functional recombinant hemagglutinin and neuraminidase proteins from the novel H7N9 influenza virus using the baculovirus expression system. J Vis Exp. Nov. 6, 2013;(81):e51112. 10 pages.
Margine et al., H3N2 influenza virus infection induces broadly reactive hemagglutinin stalk antibodies in humans and mice. J Virol. Apr. 2013;87(8):4728-37.
Marks et al., By-passing immunization. Human antibodies from V-gene libraries displayed on phage. J Mol Biol. Dec. 5, 1991;222(3):581-97.
Matrosovich et al., Neuraminidase is important for the initiation of influenza virus infection in human airway epithelium. Journal of Virology. Nov. 2004;78(22):12665-7.

Memoli et al., Evaluation of Antihemagglutinin and Antineuraminidase Antibodies as Correlates of Protection in an Influenza A/H1N1 Virus Healthy Human Challenge Model. Mbio. Apr. 19, 2016;7(2):e00417-16. 12 pages.
Monto et al., Antibody to Influenza Virus Neuraminidase: An Independent Correlate of Protection. J Infect Dis. Oct. 15, 2015;212(8):1191-9.
Monto et al., Effect of neuraminidase antibody on Hong Kong influenza. Lancet. Mar. 24, 1973;1(7804):623-5.
Murphy et al., Association of serum anti-neuraminidase antibody with resistance to influenza in man. N Engl J Med. Jun. 22, 1972;286(25):1329-32.
Nachbagauer et al., Defining the antibody cross-reactome directed against the influenza virus surface glycoproteins. Nat Immunol. Apr. 2017;18(4):464-473.
Neu et al., Heads, stalks and everything else: how can antibodies eradicate influenza as a human disease? Curr Opin Immunol. Oct. 2016;42:48-55.
Nguyen et al., Assessment of pandemic and seasonal influenza A (H1N1) virus susceptibility to neuraminidase inhibitors in three enzyme activity inhibition assays. Antimicrob Agents Chemother. Sep. 2010;54(9):3671-7.
Nichol. Efficacy and effectiveness of influenza vaccination. Vaccine. Sep. 12, 2008;26 Suppl 4:D17-22.
Palese et al., Inhibition of influenza virus replication in tissue culture by 2-deoxy-2, 3-dehydro-N-trifluoroacetylneuraminic acid (FANA): mechanism of action. Journal of General Virology. Oct. 1976;33(1):159-63.
Rajendran et al., Analysis of Anti-Influenza Virus Neuraminidase Antibodies in Children, Adults, and the Elderly by ELISA and Enzyme Inhibition: Evidence for Original Antigenic Sin. mBio. Mar. 21, 2017;8(2):e02281-16.
Sandbulte et al., Discordant antigenic drift of neuraminidase and hemagglutinin in H1N1 and H3N2 influenza viruses. Proc Natl Acad Sci U S A. Dec. 20, 2011;108(51):20748-53.
Schulman et al., Protective effects of specific immunity to viral neuraminidase on influenza virus infection of mice. Journal of Virology. Aug. 1968;2(8):778-86.
Smith et al., Rapid generation of fully human monoclonal antibodies specific to a vaccinating antigen. Nature Protocols. Feb. 26, 2009; 4: 372-384.
Sultana et al., Stability of neuraminidase in inactivated influenza vaccines. Vaccine. Apr. 17, 2014;32(19):2225-30.
Thorpe et al. The preparation and cytotoxic properties of antibody-toxin conjugates. Immunol Rev. 1982;62:119-58.
Vavricka et al., Structural and functional analysis of laninamivir and its octanoate prodrug reveals group specific mechanisms for influenza NA inhibition. PLoS Pathogens. Oct. 2011;7(10):e1002249. 10 pages.
Wagner et al., Functional balance between haemagglutinin and neuraminidase in influenza virus infections. Rev Med Virol. May-Jun. 2002;12(3):159-66.
Wan et al., Molecular basis for broad neuraminidase immunity: conserved epitopes in seasonal and pandemic H1N1 as well as H5N1 influenza viruses. J Virol. Aug. 2013;87(16):9290-300.
Wan et al., Structural characterization of a protective epitope spanning A(H1N1)pdm09 influenza virus neuraminidase monomers. Nat Communictons. Feb. 10, 2015; 6: 6114. 10 pages.
Wardemann et al., Predominant autoantibody production by early human B cell precursors. Science. Sep. 5, 2003;301(5638):1374-7.
Wen-Chen et al., Cross-Reactive Neuraminidase-Inhibiting Antibodies Elicited by Immunization with Recombinant Neuraminidase Proteins of H5N1 and Pandemic H1N1 Influenza A Viruses. J Virol. Jul. 2015;89(14):7224-34.
Westgeest et al., Optimization of an enzyme-linked lectin assay suitable for rapid antigenic characterization of the neuraminidase of human influenza A(H3N2) viruses. J Virol Methods. Jun. 1, 2015;217:55-63.
Wilson et al., An influenza A virus (H7N9) anti-neuraminidase monoclonal antibody with prophylactic and therapeutic activity in vivo. Antiviral Res. Nov. 2016;135:48-55.
Wohlbold et al., Broadly protective murine monoclonal antibodies against influenza B virus target highly conserved neuraminidase epitopes. Nat Microbiol. Oct. 2017;2(10):1415-1424.

(56) References Cited

OTHER PUBLICATIONS

Wohlbold et al., In the shadow of hemagglutinin: a growing interest in influenza viral neuraminidase and its role as a vaccine antigen. Viruses. Jun. 23, 2014;6(6):2465-94.

Wohlbold et al., Vaccination with adjuvanted recombinant neuraminidase induces broad heterologous, but not heterosubtypic, cross-protection against influenza virus infection in mice. mBio. Mar. 10, 2015;6(2):e02556. 13 pages.

Wrammert et al., Broadly cross-reactive antibodies dominate the human B cell response against 2009 pandemic H1N1 influenza virus infection. J Exp Med. Jan. 17, 2011;208(1):181-93.

Wrammert et al., Rapid cloning of high-affinity human monoclonal antibodies against influenza virus. Nature. May 29, 2008;453(7195):667-71.

Wu et al., Induced opening of influenza virus neuraminidase N2 150-loop suggests an important role in inhibitor binding. Sci Rep. 2013;3:1551. 8 pages.

\* cited by examiner

FIG. 9A
229-1F06
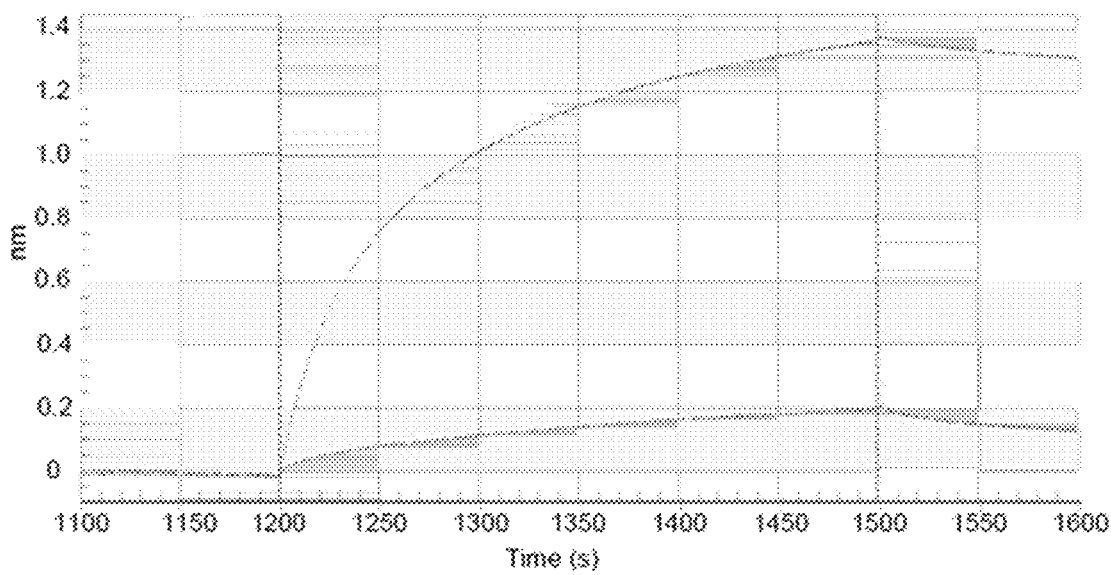
229-1G03
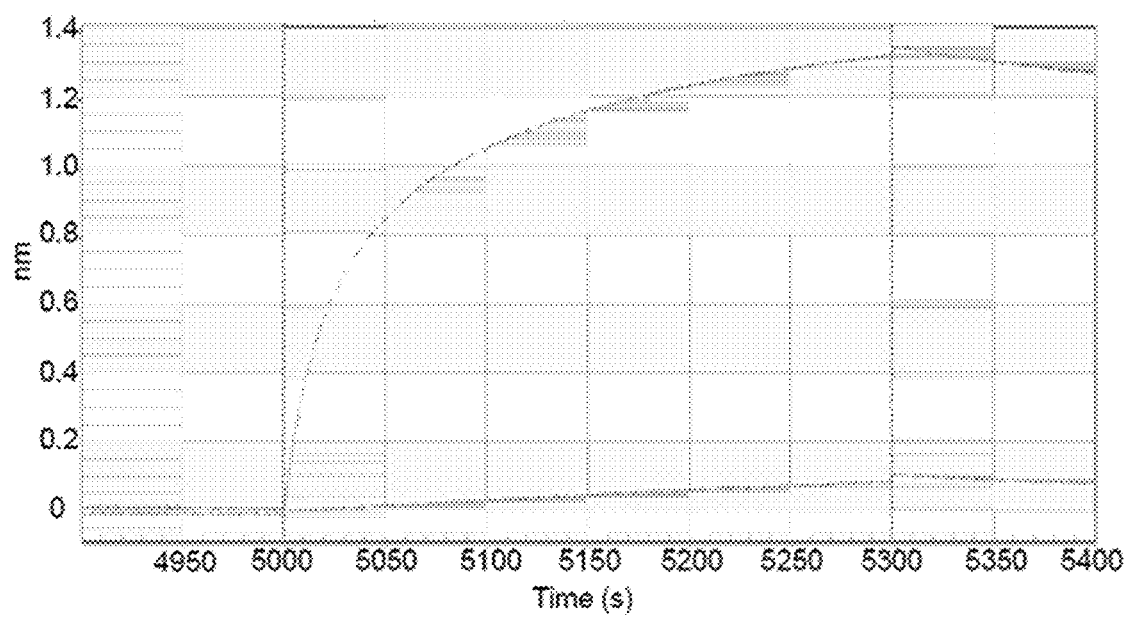
FIG. 9B

FIG. 9C
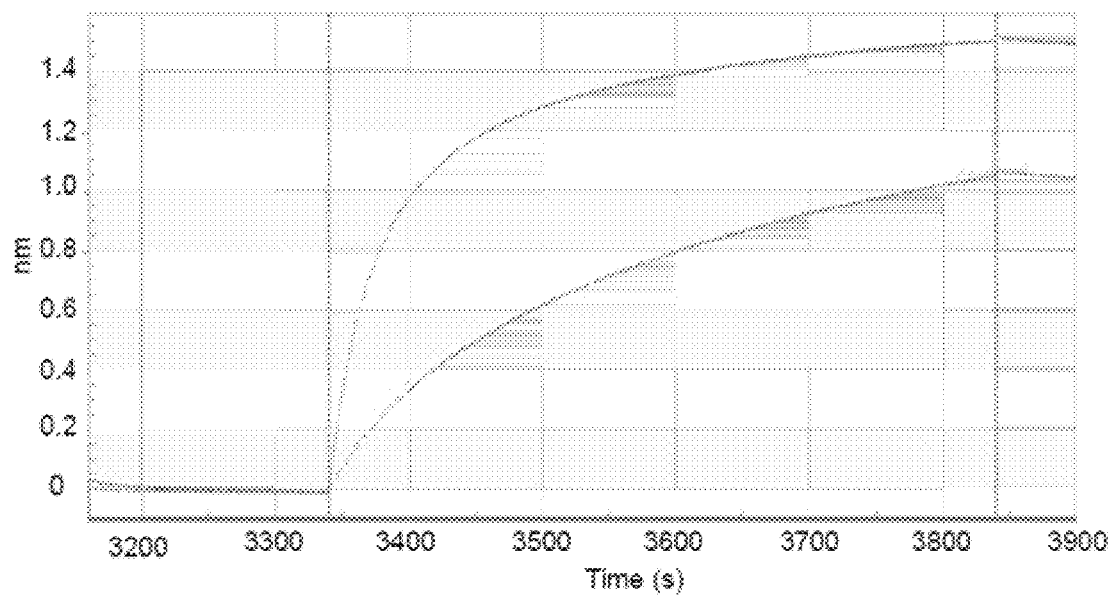
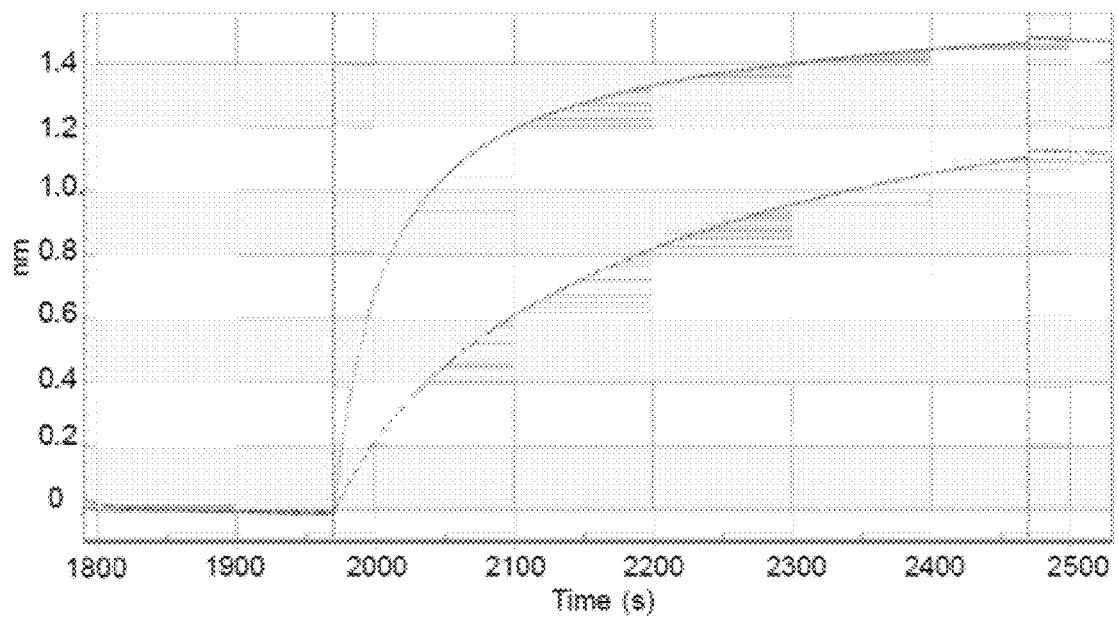
FIG. 9D

METHODS AND COMPOSITION FOR NEUTRALIZATION OF INFLUENZA

CROSS-REFERENCE TO RELATED APPLICATIONS

The present invention is a divisional of U.S. patent application Ser. No. 16/977,327, filed Sep. 1, 2020, allowed, which is a § 371 National Entry of PCT/US2019/020223, filed Mar. 1, 2019, which claims the benefit of U.S. Provisional Patent Application No. 62/637,508, filed Mar. 2, 2018, which is incorporated by reference in its entirety.

STATEMENT REGARDING FEDERAL FUNDING

This invention was made with government support under U19AI082724, U19AI109946, U19AI057266, awarded by the National Institutes of Health. The government has certain rights in the invention.

SEQUENCE LISTING

The text of the computer readable sequence listing filed herewith, titled "35579-407_SEQUENCE_LISTING_ST26", created Jun. 15, 2023, having a file size of 215,509 bytes, is hereby incorporated by reference in its entirety.

FIELD

Provided herein are anti-neuraminidase agents useful for neutralization of influenza virus, and methods of use and manufacture thereof. In particular, compositions comprising anti-neuraminidase agents (e.g., antibodies) that are cross-reactive with multiple influenza strains are provided, as well as methods of treatment and prevention of influenza infection therewith.

BACKGROUND

Influenza is an acute respiratory illness that has caused epidemics and pandemics in the human population for centuries. There are up to 5 million cases of influenza virus infection and about 250,000 to 500,000 deaths annually around the world (WHO, 2016; herein incorporated by reference in its entirety). The influenza virus has two main surface glycoproteins, hemagglutinin (HA) and neuraminidase (NA). HA, the more abundant protein, mediates binding to sialic acid receptors and subsequent fusion between the virus and host cell membranes. The less abundant tetrameric NA protein is essential for cleaving terminal sialic acid residues present on host cell surfaces, allowing the release of the newly formed viral particles (Matrosovich et al., 2004; Palese and Compans, 1976; herein incorporated by reference in their entireties). Currently, the seasonal influenza virus vaccine is the most widely available method to reduce the annual impact of influenza infection (Nichol, 2008; herein incorporated by reference in its entirety). Antibodies are the primary mediators of protection against influenza infection (Neu et al., 2016; herein incorporated by reference in its entirety). Antibodies to HA are typically considered the de facto mediators of protection from influenza infection; indeed, inhibition of HA activity has been the primary measure of influenza vaccine efficacy for decades. Therefore, most of the current approaches for vaccine design focus on inducing an antibody response to influenza virus HA. Influenza vaccine effectiveness can vary widely from season to season such that protection is always limited and in some years, is quite weak. For example, vaccine effectiveness ranged from only 19% to 48% during the past three influenza seasons according to the United States Centers for Disease Control (Flannery, 2017; herein incorporated by reference in its entirety). Studies have shown that HA antigenic drift (viral genome point mutations) is the primary reason for the limited effectiveness of the seasonal influenza vaccine (Karron and Collins, 2013; herein incorporated by reference in its entirety). Due to frequent mutations of the HA antigen, especially those located near the receptor binding domain, preexisting antibodies often show limited neutralization against currently circulating viruses (Wohlbold and Krammer, 2014; herein incorporated by reference in its entirety). Although point mutations also occur in the NA protein, the rate of antigenic drift around the active site of NA in the head domain is slower than that for HA among seasonal influenza A viruses (Abed et al., 2002; Air, 2012; herein incorporated by reference in its entirety).

SUMMARY

Provided herein are anti-neuraminidase agents useful for neutralization of influenza virus, and methods of use and manufacture thereof. In particular, compositions comprising anti-neuraminidase agents (e.g., antibodies) that are cross-reactive with multiple influenza strains are provided, as well as methods of treatment and prevention of influenza infection therewith.

Provided herein, in part, is the isolation from individuals that have been exposed to the influenza virus (e.g., live attenuated virus, fully infectious virus, etc.) of antibodies with further selection and characterization (e.g., antibodies that bind to NA, human antibodies, monoclonal antibodies, antibody fragments, etc.) that neutralize (e.g., therapeutically and/or prophylactically) influenza infection (e.g., of more than one strains of influenza A virus) and/or inhibit NA activity. In some embodiments, provided herein are epitopes to which the antibodies of the invention bind, and antibodies, antibody fragments, and/or modified antibodies based thereon (e.g., that bind to such epitopes). Accordingly, in one aspect, provided herein are antibodies and antigen binding fragments thereof that neutralize influenza infection (e.g., neutralize infection of one or more than one strain of influenza A virus).

In some embodiments, provided herein are NA-reactive antibodies and antibody fragments that bind to one or more NA types (e.g., N1, N2, N3, N4, N5, N6, N7, N8, N9, N10, and/or N11). In some embodiments, provided herein are NA-reactive antibodies and antibody fragments that cross-bind to heterologous NA proteins (e.g., from human influenza, swine influenza, avian influenza, different NA types, etc.).

In some embodiments, provided herein is an isolated antibody, or an antigen binding fragment thereof, that neutralizes infection of an N1 strain of influenza (e.g., an H1N1 virus). In another embodiment, an antibody or an antigen-binding fragment thereof also neutralizes infection of one or more additional NA influenza types (e.g., N2, N3, N4, N5, N6, N7, N8, N9, N10, and/or N11). In some embodiments, an antibody or antibody fragment binds to N309, G249, and/or N273 of N1 neuraminidase (e.g., N309 and N273, G249 and N273, etc.).

In some embodiments, provided herein is an isolated antibody, or an antigen binding fragment thereof, that neutralizes infection of an N2 strain of influenza (e.g., an H3N2 virus). In another embodiment, an antibody or an antigen-binding fragment thereof also neutralizes infection of one or more additional NA influenza types (e.g., N1, N3, N4, N5, N6, N7, N8, N9, N10, and/or N11). In some embodiments, an antibody or antibody fragment binds to the conserved enzymatic active site on the head of N2 neuraminidase.

In certain embodiments, provided herein is an antibody, or antigen binding fragment thereof, that neutralizes infection of influenza A virus (e.g., by binding and/or inhibiting NA), wherein the antibody or fragment thereof is expressed by an immortalized B cell clone. In some embodiments, the antibody or fragment thereof is expressed from the immunoglobulin genes of an isolated B cell.

In some embodiments, provided herein are NA-inhibiting (NI) antibodies and/or antibody fragments. In some embodiments, antibodies and/or antibody fragments inhibit viral egress from infected cells. In some embodiments, antibodies and/or antibody fragments inhibit release from mucins. In some embodiments, provided herein are non-NI antibodies and/or antibody fragments.

In another aspect, provided herein are nucleic acids comprising a polynucleotide encoding an antibody or antibody fragment described herein. In some embodiments, provided herein are vectors comprising a nucleic acid molecule or a cell expressing an antibody or an antigen binding fragment described herein. In some embodiments, provided herein are cells comprising a vector described herein. In some embodiments, provided herein are isolated or purified immunogenic polypeptides comprising an epitope that binds to an antibody or antigen binding fragment described herein.

Also provided herein are pharmaceutical compositions comprising an antibody or an antigen binding fragment described herein, a nucleic acid molecule described herein, a vector comprising a nucleic acid molecule described herein, a cell expressing an antibody or an antibody fragment described herein, a cell comprising a vector, or an immunogenic polypeptide; and a pharmaceutically acceptable diluent or carrier. In some embodiments, provided herein are pharmaceutical compositions comprising a first antibody or an antigen binding fragment thereof, and a second antibody, or an antigen binding fragment thereof, wherein the first antibody is an antibody described herein, and the second antibody is any antibody, or antigen binding fragment thereof, that neutralizes influenza A or influenza B virus infection.

The use of an antibody or an antigen binding fragment thereof, a nucleic acid, a vector comprising a nucleic acid, a cell expressing a vector, an isolated or purified immunogenic polypeptide comprising an epitope that binds to an antibody or antibody fragment described herein, or a pharmaceutical composition: (i) in the manufacture of a medicament for the treatment of influenza A virus infection, (ii) in a vaccine, (iii) in a composition for inducing an immune response, (iv) in diagnosis of influenza A virus infection, or (v) for research purposes, is also within the scope described herein.

In another aspect, provided herein are methods of preventing, treating or reducing influenza A virus infection or lowering the risk of influenza A virus infection comprising administering to a subject in need thereof, a therapeutically effective amount of an antibody or an antigen binding antibody fragment of the invention.

Also provided herein are epitopes which are specifically bound by an antibody or an antigen binding fragment described herein, for use (i) in therapy, (ii) in the manufacture of a medicament for treating influenza A virus infection, (iii) as a vaccine, or (iv) in screening for ligands able to neutralize influenza A virus infection.

In some embodiments, provided herein are binding agents (e.g., antibodies or antibody fragments) comprising: (a) a polypeptide comprising a region having at least 70% sequence identity (e.g., 70%, 75%, 80%, 85%, 90%, 95%, 98%, 99%, 100%, and any ranges with such endpoints (e.g., 70-100%, 80-100%, 85-99%, 90-99%, etc.)) with a polypeptide of SEQ ID NOs. 2, 18, 34, 50, 66, 82, 98, 114, 130, 146, 162, 178, 194, 209, 217, and 225; and (b) a polypeptide comprising a region having at least 70% sequence identity (e.g., 70%, 75%, 80%, 85%, 90%, 95%, 98%, 99%, 100%, and any ranges with such endpoints (e.g., 70-100%, 85-99%, 90-99%, etc.)) with a polypeptide of SEQ ID NOs. 10, 26, 42, 58, 74, 90, 106, 122, 138, 154, 170, 186, 202, 213, 221, and 229; wherein the binding agent exhibits similar influenza epitope-binding characteristics to an antibody comprising a heavy and light chain variable regions with 100% sequence identity to those of 228-14-035-2D04, 229-14-036-1D05, 229-14-036-1G03, 229-14-036-2B04, 229-14-036-2C06, 235-15-042-1E06, 1000-2E06, 294-16-009-A-1C02, 294-16-009-A-1C06, 294-16-009-A-1D05, 294-16-009-G-1F01, 296-16-003-G-2F04, 300-16-005-G-2A04, 229-1D02, 229-1F06, and/or 229-2D03.

In some embodiments, provided herein are binding agents (e.g., antibodies or antibody fragments) comprising: (a) a polypeptide comprising a region having at least 70% sequence identity (e.g., 70%, 75%, 80%, 85%, 90%, 95%, 98%, 99%, 100%, and any ranges with such endpoints (e.g., 70-100%, 80-100%, 85-99%, 90-99%, etc.)) with a polypeptide of SEQ ID NOs. 2, 18, 34, 50, 66, 82, 98, 114, 130, 146, 162, 178, 194, 209, 217, and 225; and (b) a polypeptide comprising a region having at least 70% sequence identity (e.g., 70%, 75%, 80%, 85%, 90%, 95%, 98%, 99%, 100%, and any ranges with such endpoints (e.g., 70-100%, 85-99%, 90-99%, etc.)) with a polypeptide of SEQ ID NOs. 10, 26, 42, 58, 74, 90, 106, 122, 138, 154, 170, 186, 202, 213, 221, and 229; wherein the binding agent exhibits similar influenza epitope-binding characteristics to an antibody comprising a heavy and light chain variable regions with 100% sequence identity to those of 228-14-035-2D04, 229-14-036-1D05, 229-14-036-1G03, 229-14-036-2B04, 229-14-036-2C06, 235-15-042-1E06, 1000-2E06, 294-16-009-A-1C02, 294-16-009-A-1C06, 294-16-009-A-1D05, 294-16-009-G-1F01, 296-16-003-G-2F04, 300-16-005-G-2A04, 229-1D02, 229-1F06, and/or 229-2D03.

Experiments conducted during development of embodiments herein indicate the presence of certain amino acids in a neuraminidase enzyme that are recognized by the antibodies disclosed herein (Table 2). In some embodiments, the amino acids of Table 2 are recognized by binding agents corresponding to 229-14-036-1D05, 235-15-042-1E06, 294-16-009-A-1C02, or 294-16-009-A-1D05, respectively.

TABLE 2

| Antibody name | Critical amino acid |
|---|---|
| 229-14-036-1D05 | N221, G248 and G429 |
| 235-15-042-1E06 | G248 and G429 |
| 294-16-009-A-1C02 | N270 and N309 |
| 294-16-009-A-1D05 | N309 |

In some embodiments, provided herein is a neuraminidase protein (e.g., recombinant neuraminidase) comprising amino acids of Table 2. In some embodiments, a neuraminidase protein is used to generate or purify therapeutic antibodies. In some embodiments, provided herein is a virus particle expressing a recombinant neuraminidase comprising amino acids of Table 2. In some embodiments, provided herein is a neuraminidase antigen (e.g., recombinant neuraminidase antigen) comprising the amino acids of Table 2.

In some embodiments, provided herein are binding agents (e.g., antibodies or antibody fragments) comprising: (a) a polypeptide comprising a region having at least 70% sequence identity (e.g., 70%, 75%, 80%, 85%, 90%, 95%, 98%, 99%, 100%, and any ranges with such endpoints (e.g., 70-100%, 80-100%, 85-99%, 90-99%, etc.)) with a polypeptide encoded by a nucleic acid of SEQ ID NOs. 1, 17, 33, 49, 65, 81, 97, 113, 129, 145, 161, 177, and/or 193; and (b) a polypeptide comprising a region having at least 70% sequence identity (e.g., 70%, 75%, 80%, 85%, 90%, 95%, 98%, 99%, 100%, and any ranges with such endpoints (e.g., 70-100%, 80-100%, 85-99%, 90-99%, etc.)) with a polypeptide encoded by a nucleic acid of SEQ ID NOs. 9, 25, 41, 57, 73, 89, 105, 121, 137, 153, 169, 185, and/or 201; wherein the binding agent exhibits similar influenza epitope-binding characteristics to an antibody comprising a heavy and light chain variable regions with 100% sequence identity to those of 228-14-035-2D04, 229-14-036-1D05, 229-14-036-1G03, 229-14-036-2B04, 229-14-036-2C06, 235-15-042-1E06, 1000-2E06, 294-16-009-A-1C02, 294-16-009-A-1C06, 294-16-009-A-1D05, 294-16-009-G-1F01, 296-16-003-G-2F04, 300-16-005-G-2A04, 229-1D02, 229-1F06, and/or 229-2D03.

In some embodiments, similar influenza epitope-binding characteristics comprises: (1) binding to the same epitope, (2) binding to the same epitope with the same affinity (e.g., as measured by immunofluorescence, ELISA, etc.), binding to the same epitope with less than reduction (e.g., 8-fold, 6-fold, 4-fold, 2-fold, etc.) in affinity (e.g., as measured by immunofluorescence, ELISA, etc.).

In some embodiments, the polypeptide of (a) and the polypeptide of (b) comprise first and second polypeptides. In some embodiments, the binding agent is a monoclonal antibody or monobody. In some embodiments, the binding agent is an antibody fragment (e.g., Fab, F(ab') 2, Fab'. scFv, di-scFv, sdAb, etc.). In some embodiments, the polypeptide of (a) and the polypeptide of (b) are a single polypeptide chain.

In some embodiments, the binding agent comprises a binding affinity for an epitope or epitopes displayed on two or more different virus strains. In some embodiments, the two or more different virus strains are influenza strains (e.g., N1, N2, N3, N4, N5, N6, N7, N8, N9, N10, and/or N11 influenza stains). In some embodiments, a first influenza strain is an N1 strain (e.g., H1N1). In some embodiments, a first influenza strain is an N2 strain (e.g., H3N2).

In some embodiments, provided herein is a binding agent (e.g., antibody, antibody fragment, etc.) that bind to an epitope of an influenza NA protein, neutralizes infection of one or more strains of influenza A virus, and/or inhibits an influenza NA protein, and comprises:

(i) a heavy chain variable region comprising a CDR1 of SEQ ID NO: 4, a CDR2 of SEQ ID NO: 6 and CDR3 of SEQ ID NO: 8, and a light chain variable region comprising a CDR1 of SEQ ID NO: 12, a CDR2 of SEQ ID NO: 14 and CDR3 of SEQ ID NO: 16;

(ii) a heavy chain variable region comprising a CDR1 of SEQ ID NO: 20, a CDR2 of SEQ ID NO: 22 and CDR3 of SEQ ID NO: 24, and a light chain variable region comprising a CDR1 of SEQ ID NO: 28, a CDR2 of SEQ ID NO: 30 and CDR3 of SEQ ID NO: 32;

(iii) a heavy chain variable region comprising a CDR1 of SEQ ID NO: 36, a CDR2 of SEQ ID NO: 38 and CDR3 of SEQ ID NO: 40, and a light chain variable region comprising a CDR1 of SEQ ID NO: 44, a CDR2 of SEQ ID NO: 46 and CDR3 of SEQ ID NO: 48;

(iv) a heavy chain variable region comprising a CDR1 of SEQ ID NO: 52, a CDR2 of SEQ ID NO: 54 and CDR3 of SEQ ID NO: 56, and a light chain variable region comprising a CDR1 of SEQ ID NO: 60, a CDR2 of SEQ ID NO: 62 and CDR3 of SEQ ID NO: 64;

(v) a heavy chain variable region comprising a CDR1 of SEQ ID NO: 68, a CDR2 of SEQ ID NO: 70 and CDR3 of SEQ ID NO: 72, and a light chain variable region comprising a CDR1 of SEQ ID NO: 76, a CDR2 of SEQ ID NO: 78 and CDR3 of SEQ ID NO: 80;

(vi) a heavy chain variable region comprising a CDR1 of SEQ ID NO: 84, a CDR2 of SEQ ID NO: 86 and CDR3 of SEQ ID NO: 88, and a light chain variable region comprising a CDR1 of SEQ ID NO: 92, a CDR2 of SEQ ID NO: 94 and CDR3 of SEQ ID NO: 96;

(vii) a heavy chain variable region comprising a CDR1 of SEQ ID NO: 100, a CDR2 of SEQ ID NO: 102 and CDR3 of SEQ ID NO: 104, and a light chain variable region comprising a CDR1 of SEQ ID NO: 108, a CDR2 of SEQ ID NO: 110 and CDR3 of SEQ ID NO: 112;

(viii) a heavy chain variable region comprising a CDR1 of SEQ ID NO: 116, a CDR2 of SEQ ID NO: 118 and CDR3 of SEQ ID NO: 120, and a light chain variable region comprising a CDR1 of SEQ ID NO: 124, a CDR2 of SEQ ID NO: 126 and CDR3 of SEQ ID NO: 128;

(ix) a heavy chain variable region comprising a CDR1 of SEQ ID NO: 132, a CDR2 of SEQ ID NO: 134 and CDR3 of SEQ ID NO: 136, and a light chain variable region comprising a CDR1 of SEQ ID NO: 140, a CDR2 of SEQ ID NO: 142 and CDR3 of SEQ ID NO: 144;

(x) a heavy chain variable region comprising a CDR1 of SEQ ID NO: 148, a CDR2 of SEQ ID NO: 150 and CDR3 of SEQ ID NO: 152, and a light chain variable region comprising a CDR1 of SEQ ID NO: 156, a CDR2 of SEQ ID NO: 158 and CDR3 of SEQ ID NO: 160;

(xi) a heavy chain variable region comprising a CDR1 of SEQ ID NO: 164, a CDR2 of SEQ ID NO: 166 and CDR3 of SEQ ID NO: 168, and a light chain variable region comprising a CDR1 of SEQ ID NO: 172, a CDR2 of SEQ ID NO: 174 and CDR3 of SEQ ID NO: 176;

(xii) a heavy chain variable region comprising a CDR1 of SEQ ID NO: 180, a CDR2 of SEQ ID NO: 182 and CDR3 of SEQ ID NO: 184, and a light chain variable region comprising a CDR1 of SEQ ID NO: 188, a CDR2 of SEQ ID NO: 190 and CDR3 of SEQ ID NO: 192;

(xiii) a heavy chain variable region comprising a CDR1 of SEQ ID NO: 196, a CDR2 of SEQ ID NO: 198 and CDR3 of SEQ ID NO: 200, and a light chain variable region comprising a CDR1 of SEQ ID NO: 204, a CDR2 of SEQ ID NO: 206 and CDR3 of SEQ ID NO: 208.

(xix) a heavy chain variable region comprising a CDR1 of SEQ ID NO: 210, a CDR2 of SEQ ID NO: 211 and CDR3 of SEQ ID NO: 212, and a light chain variable region comprising a CDR1 of SEQ ID NO: 214, a CDR2 of SEQ ID NO: 215 and CDR3 of SEQ ID NO: 216;

(xx) a heavy chain variable region comprising a CDR1 of SEQ ID NO: 218, a CDR2 of SEQ ID NO: 219 and CDR3 of SEQ ID NO: 220, and a light chain variable region comprising a CDR1 of SEQ ID NO: 222, a CDR2 of SEQ ID NO: 223 and CDR3 of SEQ ID NO: 224; and/or (xxi) a heavy chain variable region comprising a CDR1 of SEQ ID NO: 226, a CDR2 of SEQ ID NO: 227 and CDR3 of SEQ ID NO: 228, and a light chain variable region comprising a CDR1 of SEQ ID NO: 230, a CDR2 of SEQ ID NO: 231 and CDR3 of SEQ ID NO: 232.

In some embodiments, provided herein a heavy chain variable region comprising:

(i) a CDR1 of SEQ ID NO: 4, a CDR2 of SEQ ID NO: 6 and CDR3 of SEQ ID NO: 8, wherein the heavy chain variable region comprises less than 100% sequence identity (e.g., 99%, 95%, 90%, 85%, 80%, 75%, 70%, or less or ranges therebetween) with SEQ ID NO: 2;

(ii) a CDR1 of SEQ ID NO: 20, a CDR2 of SEQ ID NO: 22 and CDR3 of SEQ ID NO: 24, wherein the heavy chain variable region comprises less than 100% sequence identity (e.g., 99%, 95%, 90%, 85%, 80%, 75%, 70%, or less or ranges therebetween) with SEQ ID NO: 18;

(iii) a CDR1 of SEQ ID NO: 36, a CDR2 of SEQ ID NO: 38 and CDR3 of SEQ ID NO: 40, wherein the heavy chain variable region comprises less than 100% sequence identity (e.g., 99%, 95%, 90%, 85%, 80%, 75%, 70%, or less or ranges therebetween) with SEQ ID NO: 34;

(iv) a CDR1 of SEQ ID NO: 52, a CDR2 of SEQ ID NO: 54 and CDR3 of SEQ ID NO: 56, wherein the heavy chain variable region comprises less than 100% sequence identity (e.g., 99%, 95%, 90%, 85%, 80%, 75%, 70%, or less or ranges therebetween) with SEQ ID NO: 50;

(v) a CDR1 of SEQ ID NO: 68, a CDR2 of SEQ ID NO: 70 and CDR3 of SEQ ID NO: 72, wherein the heavy chain variable region comprises less than 100% sequence identity (e.g., 99%, 95%, 90%, 85%, 80%, 75%, 70%, or less or ranges therebetween) with SEQ ID NO: 66;

(vi) a CDR1 of SEQ ID NO: 84, a CDR2 of SEQ ID NO: 86 and CDR3 of SEQ ID NO: 88, wherein the heavy chain variable region comprises less than 100% sequence identity (e.g., 99%, 95%, 90%, 85%, 80%, 75%, 70%, or less or ranges therebetween) with SEQ ID NO: 82;

(vii) a CDR1 of SEQ ID NO: 100, a CDR2 of SEQ ID NO: 102 and CDR3 of SEQ ID NO: 104, wherein the heavy chain variable region comprises less than 100% sequence identity (e.g., 99%, 95%, 90%, 85%, 80%, 75%, 70%, or less or ranges therebetween) with SEQ ID NO: 98;

(viii) a CDR1 of SEQ ID NO: 116, a CDR2 of SEQ ID NO: 118 and CDR3 of SEQ ID NO: 120, wherein the heavy chain variable region comprises less than 100% sequence identity (e.g., 99%, 95%, 90%, 85%, 80%, 75%, 70%, or less or ranges therebetween) with SEQ ID NO: 114;

(ix) a CDR1 of SEQ ID NO: 132, a CDR2 of SEQ ID NO: 134 and CDR3 of SEQ ID NO: 136, wherein the heavy chain variable region comprises less than 100% sequence identity (e.g., 99%, 95%, 90%, 85%, 80%, 75%, 70%, or less or ranges therebetween) with SEQ ID NO: 130;

(x) a CDR1 of SEQ ID NO: 148, a CDR2 of SEQ ID NO: 150 and CDR3 of SEQ ID NO: 152, wherein the heavy chain variable region comprises less than 100% sequence identity (e.g., 99%, 95%, 90%, 85%, 80%, 75%, 70%, or less or ranges therebetween) with SEQ ID NO: 146;

(xi) a CDR1 of SEQ ID NO: 164, a CDR2 of SEQ ID NO: 166 and CDR3 of SEQ ID NO: 168, wherein the heavy chain variable region comprises less than 100% sequence identity (e.g., 99%, 95%, 90%, 85%, 80%, 75%, 70%, or less or ranges therebetween) with SEQ ID NO: 162;

(xii) a CDR1 of SEQ ID NO: 180, a CDR2 of SEQ ID NO: 182 and CDR3 of SEQ ID NO: 184, wherein the heavy chain variable region comprises less than 100% sequence identity (e.g., 99%, 95%, 90%, 85%, 80%, 75%, 70%, or less or ranges therebetween) with SEQ ID NO: 178;

(xiii) a CDR1 of SEQ ID NO: 196, a CDR2 of SEQ ID NO: 198 and CDR3 of SEQ ID NO: 200, wherein the heavy chain variable region comprises less than 100% sequence identity (e.g., 99%, 95%, 90%, 85%, 80%, 75%, 70%, or less or ranges therebetween) with SEQ ID NO: 194;

(xix) a CDR1 of SEQ ID NO: 210, a CDR2 of SEQ ID NO: 211 and CDR3 of SEQ ID NO: 212, wherein the heavy chain variable region comprises less than 100% sequence identity (e.g., 99%, 95%, 90%, 85%, 80%, 75%, 70%, or less or ranges therebetween) with SEQ ID NO: 209;

(xx) a CDR1 of SEQ ID NO: 218, a CDR2 of SEQ ID NO: 219 and CDR3 of SEQ ID NO: 220, wherein the heavy chain variable region comprises less than 100% sequence identity (e.g., 99%, 95%, 90%, 85%, 80%, 75%, 70%, or less or ranges therebetween) with SEQ ID NO: 217; and/or (xxi) a CDR1 of SEQ ID NO: 226, a CDR2 of SEQ ID NO: 227 and CDR3 of SEQ ID NO: 228, wherein the heavy chain variable region comprises less than 100% sequence identity (e.g., 99%, 95%, 90%, 85%, 80%, 75%, 70%, or less or ranges therebetween) with SEQ ID NO: 225.

In some embodiments, provided herein is a binding agent (e.g., antibody, antibody fragment, etc.) comprising a heavy chain variable region of one or (i) through (xiii) above.

In some embodiments, provided herein is a light chain variable region comprising:

(i) a CDR1 of SEQ ID NO: 12, a CDR2 of SEQ ID NO: 14 and CDR3 of SEQ ID NO: 16, wherein the light chain variable region comprises less than 100% sequence identity (e.g., 99%, 95%, 90%, 85%, 80%, 75%, 70%, or less or ranges therebetween) with SEQ ID NO: 10;

(ii) a CDR1 of SEQ ID NO: 28, a CDR2 of SEQ ID NO: 30 and CDR3 of SEQ ID NO: 32, wherein the light chain variable region comprises less than 100% sequence identity (e.g., 99%, 95%, 90%, 85%, 80%, 75%, 70%, or less or ranges therebetween) with SEQ ID NO: 26;

(iii) a CDR1 of SEQ ID NO: 44, a CDR2 of SEQ ID NO: 46 and CDR3 of SEQ ID NO: 48, wherein the light chain variable region comprises less than 100% sequence identity (e.g., 99%, 95%, 90%, 85%, 80%, 75%, 70%, or less or ranges therebetween) with SEQ ID NO: 42;

(iv) a CDR1 of SEQ ID NO: 60, a CDR2 of SEQ ID NO: 62 and CDR3 of SEQ ID NO: 64, wherein the light chain variable region comprises less than 100% sequence identity (e.g., 99%, 95%, 90%, 85%, 80%, 75%, 70%, or less or ranges therebetween) with SEQ ID NO: 58;

(v) a CDR1 of SEQ ID NO: 76, a CDR2 of SEQ ID NO: 78 and CDR3 of SEQ ID NO: 80, wherein the light chain variable region comprises less than 100% sequence identity (e.g., 99%, 95%, 90%, 85%, 80%, 75%, 70%, or less or ranges therebetween) with SEQ ID NO: 74;

(vi) a CDR1 of SEQ ID NO: 92, a CDR2 of SEQ ID NO: 94 and CDR3 of SEQ ID NO: 96, wherein the light chain variable region comprises less than 100% sequence identity (e.g., 99%, 95%, 90%, 85%, 80%, 75%, 70%, or less or ranges therebetween) with SEQ ID NO: 90;

(vii) a CDR1 of SEQ ID NO: 108, a CDR2 of SEQ ID NO: 110 and CDR3 of SEQ ID NO: 112, wherein the light chain variable region comprises less than 100% sequence identity (e.g., 99%, 95%, 90%, 85%, 80%, 75%, 70%, or less or ranges therebetween) with SEQ ID NO: 106;

(viii) a CDR1 of SEQ ID NO: 124, a CDR2 of SEQ ID NO: 126 and CDR3 of SEQ ID NO: 128, wherein the light chain variable region comprises less than 100% sequence identity (e.g., 99%, 95%, 90%, 85%, 80%, 75%, 70%, or less or ranges therebetween) with SEQ ID NO: 122;

(ix) a CDR1 of SEQ ID NO: 140, a CDR2 of SEQ ID NO: 142 and CDR3 of SEQ ID NO: 144, wherein the light chain variable region comprises less than 100% sequence identity (e.g., 99%, 95%, 90%, 85%, 80%, 75%, 70%, or less or ranges therebetween) with SEQ ID NO: 138;

(x) a CDR1 of SEQ ID NO: 156, a CDR2 of SEQ ID NO: 158 and CDR3 of SEQ ID NO: 160, wherein the light chain variable region comprises less than 100% sequence identity (e.g., 99%, 95%, 90%, 85%, 80%, 75%, 70%, or less or ranges therebetween) with SEQ ID NO: 154;

(xi) a CDR1 of SEQ ID NO: 172, a CDR2 of SEQ ID NO: 174 and CDR3 of SEQ ID NO: 176, wherein the light chain variable region comprises less than 100% sequence identity (e.g., 99%, 95%, 90%, 85%, 80%, 75%, 70%, or less or ranges therebetween) with SEQ ID NO: 170;

(xii) a CDR1 of SEQ ID NO: 188, a CDR2 of SEQ ID NO: 190 and CDR3 of SEQ ID NO: 192, wherein the light chain variable region comprises less than 100% sequence identity (e.g., 99%, 95%, 90%, 85%, 80%, 75%, 70%, or less or ranges therebetween) with SEQ ID NO: 186;

(xiii) a CDR1 of SEQ ID NO: 204, a CDR2 of SEQ ID NO: 206 and CDR3 of SEQ ID NO: 208, wherein the light chain variable region comprises less than 100% sequence identity (e.g., 99%, 95%, 90%, 85%, 80%, 75%, 70%, or less or ranges therebetween) with SEQ ID NO: 202;

(xix) a CDR1 of SEQ ID NO: 214, a CDR2 of SEQ ID NO: 215 and CDR3 of SEQ ID NO: 216, wherein the heavy chain variable region comprises less than 100% sequence identity (e.g., 99%, 95%, 90%, 85%, 80%, 75%, 70%, or less or ranges therebetween) with SEQ ID NO: 213;

(xx) a CDR1 of SEQ ID NO: 222, a CDR2 of SEQ ID NO: 223 and CDR3 of SEQ ID NO: 224, wherein the heavy chain variable region comprises less than 100% sequence identity (e.g., 99%, 95%, 90%, 85%, 80%, 75%, 70%, or less or ranges therebetween) with SEQ ID NO: 221; and/or (xxi) a CDR1 of SEQ ID NO: 230, a CDR2 of SEQ ID NO: 231 and CDR3 of SEQ ID NO: 232, wherein the heavy chain variable region comprises less than 100% sequence identity (e.g., 99%, 95%, 90%, 85%, 80%, 75%, 70%, or less or ranges therebetween) with SEQ ID NO: 229.

In some embodiments, provided herein is a binding agent (e.g., antibody, antibody fragment, etc.) comprising a light chain variable region of one or (i) through (xiii) above.

In some embodiments, provided herein are methods comprising administering a therapeutic dose of a pharmaceutical preparation, composition, and/or formulation described herein (e.g., comprising a binding agents (e.g., antibodies, antibody fragments, etc.) described herein) to a subject. In some embodiments, the subject is a human or non-human animal. In some embodiments, the subject is infected with influenza (e.g., influenza A). In some embodiments, the subject is at risk of influenza infection. In some embodiments, the subject is infected with strain of influenza that expresses a neuraminidase selected from N1, N2, N3, N4, N5, N6, N7, N8, N9, N10, N11. In some embodiments, the binding agent comprises an amino acid sequence that is the same or is substantially similar (e.g., sequence similarity of 70%, 75%, 80%, 85%, 90%, 95%, 98%, 99%, 100%, or ranges therebetween) or is encoded by a nucleic acid sequence that is the same or is substantially similar (e.g., sequence similarity of 70%, 75%, 80%, 85%, 90%, 95%, 98%, 99%, 100%, or ranges therebetween) to a sequence described herein (e.g., SEQ ID NOs: 1-232). In some embodiments, the binding agent is purified and/or isolated from a subject that has been infected with influenza. In some embodiments, the binding agent is the same or is substantially similar (e.g., sequence similarity of 70%, 75%, 80%, 85%, 90%, 95%, 98%, 99%, 100%, or ranges therebetween) to sequences from a binding agent purified and/or isolated from a subject that has been infected with influenza. In some embodiments, the binding agent is co-administered with one or more additional therapeutic agents. In some embodiments, the one or more additional therapeutic agents are selected from the group consisting of antivirals, immunologic agents, antibiotics, and agents for relieving symptoms of influenza infection.

In some embodiments, provided herein are methods of treating or preventing an influenza virus infection comprising administering to a first subject an antibody generated by a second subject infected with an influenza virus. In some embodiments, an antibody from the second subject is isolated. In some embodiments, an antibody or antibody fragment comprising the same or similar binding and/or neutralization characteristics (e.g., variable region, CDRs, etc.) to the antibody isolated from the second subject is administered. In some embodiments, the antibody is a monoclonal antibody. In some embodiments, the antibody is an antibody fragment. In some embodiments, the antibody is produced by hybridoma, recombinant technology, and/or chemical synthesis. In some embodiments, the antibody administered to the first subject is a modified version of the antibody obtained from second subject.

In some embodiments, provided herein are binding agents (e.g., antibodies, antibody fragments, etc.) that neutralize infection of one or more strains of influenza (e.g., influenza A virus). In some embodiments, binding agents bind the same epitope an antibody selected from the group consisting of 228-14-035-2D04, 229-14-036-1D05, 229-14-036-1G03, 229-14-036-2B04, 229-14-036-2C06, 235-15-042-1E06, 1000-2E06, 294-16-009-A-1C02, 294-16-009-A-1C06, 294-16-009-A-1D05, 294-16-009-G-1F01, 296-16-003-G-2F04, 300-16-005-G-2A04, 229-1D02, 229-1F06, and/or 229-2D03. In some embodiments, the binding agent has an affinity for the epitope of at least $10^7$ $M^{-1}$. In some embodiments, the binding agent comprises variable regions and/or CDRs that are at least 70% (e.g., 70%, 75%, 80%, 85%, 90%, 95%, 100%, or ranges therebetween) identical to the heavy and light (e.g., lambda or kappa) chains and/or CDRH and CDRL/CDRK of 228-14-035-2D04, 229-14-036-1D05, 229-14-036-1G03, 229-14-036-2B04, 229-14-036-2C06, 235-15-042-1E06, 1000-2E06, 294-16-009-A-1C02, 294-16-009-A-1C06, 294-16-009-A-1D05, 294-16-009-G-1F01, 296-16-003-G-2F04, 300-16-005-G-2A04, 229-1D02, 229-1F06, and/or 229-2D03.

In some embodiments, provided herein is the use of the antibodies or antibody fragments described herein for the treatment of influenza infection. In some embodiments, provided herein are the antibodies or antibody fragments described herein for use as a medicament. In some embodiments, provided herein are antibodies or antibody fragments for use in the treatment of influenza infection. In some embodiments, provided herein is the use of the antibodies or antibody fragments described herein for the manufacture of a medicament for the treatment of influenza infection.

In some embodiments, provided herein is the use of the antibodies, antibody fragments, antigens, and/or epitopes described herein for the diagnosis and/or characterization of an influenza infection. In some embodiments, detection of one or more antigens/epitopes described herein (e.g., using the antibodies/antibody fragments described herein) indicates that a subject or sample is infected with influenza (e.g., a particular strain or type of influenza). In some embodiments, diagnostic methods herein find use in directing the treatment of influenza infection. In some embodiments, provided herein are assays and/or devices comprising the antibodies, antibody fragments, antigens, and/or epitopes described herein for use in the diagnosis and/or characterization of an influenza infection.

In some embodiments, provided herein are quality control reagents comprising the antibodies, antibody fragments, antigens, and/or epitopes described herein. In some embodiments, provided herein are research reagents comprising the antibodies, antibody fragments, antigens, and/or epitopes described herein.

BRIEF DESCRIPTION OF THE DRAWINGS

FIGS. 9A-E. Binding competition between 5 N2-reactive mAbs and oseltamivir to A/Texas/50/2012 rNA were measured by bio-layer interferometry. (A) 229-1F06 (B) 229-1G03 (C) 235-1C02 (D) 235-1E06 (E) 229-2C06.

DEFINITIONS

Figure 1:
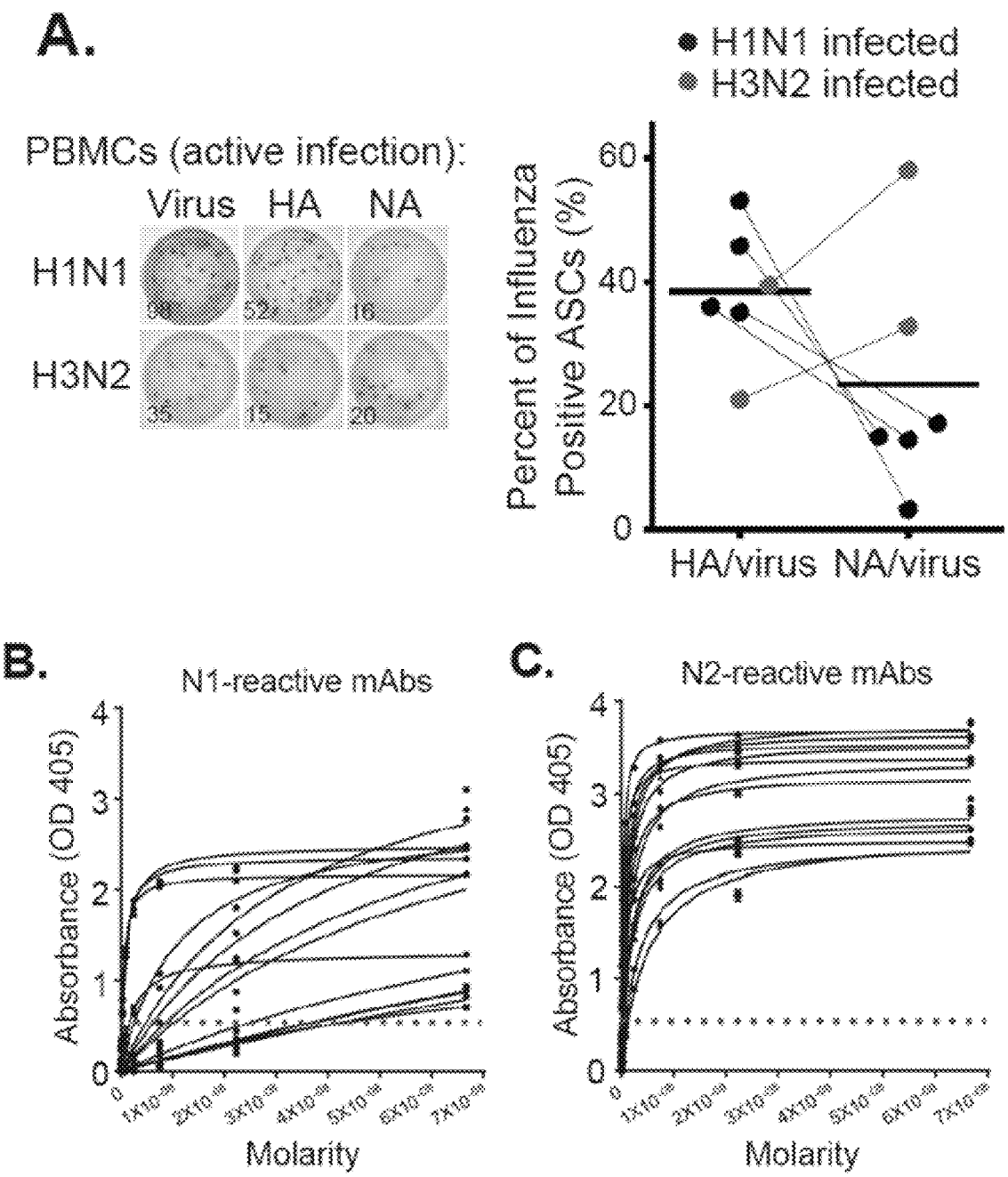
FIG. 1. Influenza virus infection induces a greater prevalence of NA-reactive antibodies as compared to vaccination (Panel A) The proportions of HA-reactive and NA-reactive secreting cells (ASCs) out of the total virus-reactive cells were determined by ELISPOT assay. Individuals infected with an H1N1 influenza virus were compared to individuals infected with an H3N2 influenza virus. Each dot represents a subject (n=6). (Panels B-C) Binding of NA-reactive mAbs to rNA proteins by ELISA. Represented are ELISA binding curves. The antibody starting concentration is 10 µg/ml. The assays were performed in duplicate at least 3 times for each antibody. (Panel B) Binding to A/California/7/2009 (H1N1) rN1 protein or (Panel C) A/Texas/50/2012 (H3N2) rN2 protein. (Panels D-E) Proportion of influenza virus-reactive mAbs that bind to HA, NA or other antigens (Panel D) One hundred and twenty-eight mAbs were isolated from influenza virus infected individuals (H1N1 and H3N2). Pie charts show the percentages of mAbs that bind a given antigen (HA, NA, or other). Graphed on the right are the percentages of HA- and NA-reactive antibodies per individual. Each dot represents one individual (n=11). Red indicates patients with no NA B cells detected on first exposure to the pandemic H1N1 strain in 2009 (E) Two hundred and fifty-eight mAbs were isolated from influenza virus vaccinated individuals from previously published studies in our laboratory (Andrews et al., 2015; Wrammert et al., 2008). As in (Panel D), pie charts show the percentages of mAbs that bind a given antigen (HA, NA, or other) in individuals vaccinated with influenza virus subunit vaccine (seasons 2006-2008 and 2010-2011), influenza virus split vaccine (2008-2010), or monovalent pandemic H1N1 vaccine (2009-2010). For the panels (Panel A) and (Panel D), the dots indicate patients infected with an H3N2 virus.
Figure 1:
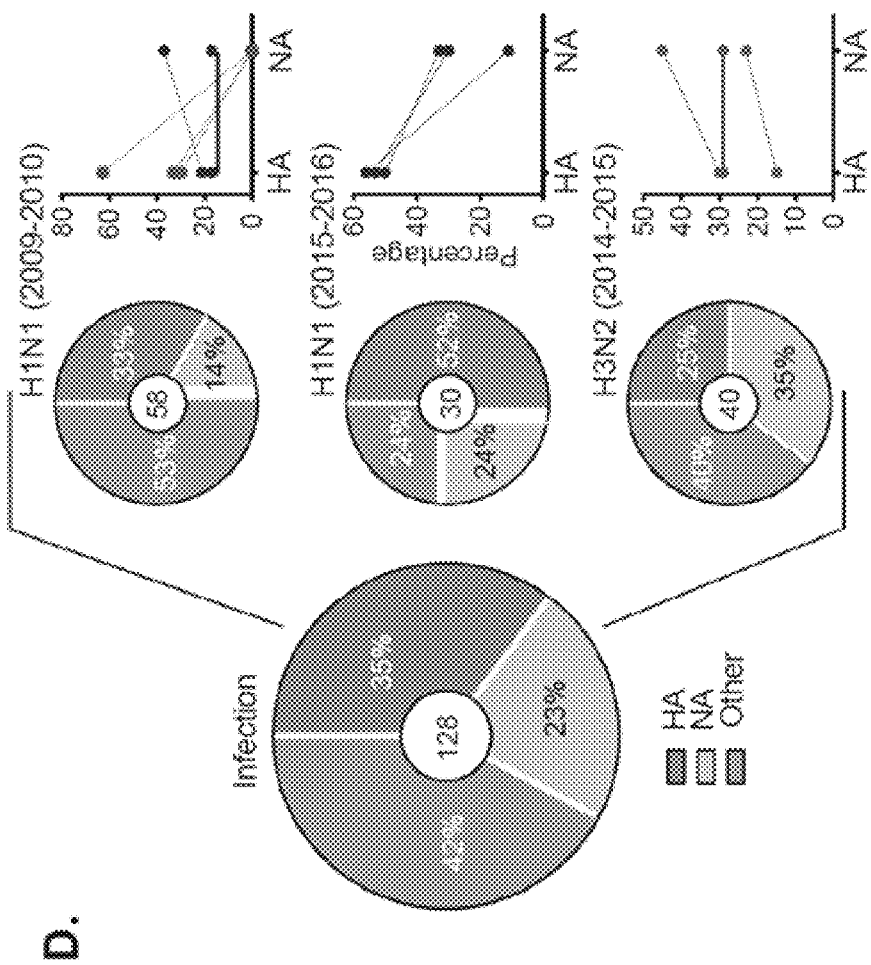

As used herein, the term "subject" broadly refers to any animal, including but not limited to, human and non-human animals (e.g., dogs, cats, cows, horses, sheep, poultry, fish, crustaceans, etc.). As used herein, the term "patient" typically refers to a subject that is being treated for a disease or condition.

As used herein, the term "antibody" refers to a whole antibody molecule or a fragment thereof (e.g., fragments such as Fab, Fab', and F(ab') 2), it may be a polyclonal or monoclonal antibody, a chimeric antibody, a humanized antibody, a human antibody, etc.

A native antibody typically has a tetrameric structure. A tetramer typically comprises two identical pairs of polypeptide chains, each pair having one light chain (in certain embodiments, about 25 kDa) and one heavy chain (in certain embodiments, about 50-70 kDa). In a native antibody, a heavy chain comprises a variable region, $V_H$, and three constant regions, $C_{H1}$, $C_{H2}$, and $C_{H3}$. The $V_H$ domain is at the amino-terminus of the heavy chain, and the $C_{H3}$ domain is at the carboxy-terminus. In a native antibody, a light chain comprises a variable region, $V_L$, and a constant region, $C_L$. The variable region of the light chain is at the amino-terminus of the light chain. In a native antibody, the variable regions of each light/heavy chain pair typically form the antigen binding site. The constant regions are typically responsible for effector function.

In a native antibody, the variable regions typically exhibit the same general structure in which relatively conserved framework regions (FRs) are joined by three hypervariable regions, also called complementarity determining regions (CDRs). The CDRs from the two chains of each pair typically are aligned by the framework regions, which may enable binding to a specific epitope. From N-terminus to C-terminus, both light and heavy chain variable regions typically comprise the domains FR1, CDR1, FR2, CDR2, FR3, CDR3 and PR4. The CDRs on the heavy chain are referred to as H1, H2, and H3, while the CDRs on the light chain are referred to as L1, L2, and L3. Typically, CDR3 is the greatest source of molecular diversity within the antigen-binding site. H3, for example, in certain instances, can be as short as two amino acid residues or greater than 26. The assignment of amino acids to each domain is typically in accordance with the definitions of Kabat et al. (1991) Sequences of Proteins of Immunological Interest (National Institutes of Health, Publication No. 91-3242, vols. 1-3, Bethesda, Md.); Chothia, C., and Lesk, A. M. (1987) J. Mol. Biol. 196:901-917; or Chothia, C. et al. Nature 342:878-883 (1989). In the present application, the term "CDR" refers to a CDR from either the light or heavy chain, unless otherwise specified.

As used herein, the term "heavy chain" refers to a polypeptide comprising sufficient heavy chain variable region sequence to confer antigen specificity either alone or in combination with a light chain.

As used herein, the term "light chain" refers to a polypeptide comprising sufficient light chain variable region sequence to confer antigen specificity either alone or in combination with a heavy chain.

As used herein, when an antibody or other entity "specifically recognizes" or "specifically binds" an antigen or epitope, it preferentially recognizes the antigen in a complex mixture of proteins and/or macromolecules, and binds the antigen or epitope with affinity which is substantially higher than to other entities not displaying the antigen or epitope. In this regard, "affinity which is substantially higher" means affinity that is high enough to enable detection of an antigen or epitope which is distinguished from entities using a desired assay or measurement apparatus. Typically, it means binding affinity having a binding constant ($K_a$) of at least $10^7$ $M^{-1}$ (e.g., $>10^7 M^{-1}$, $>10^8 M^{-1}$, $>10^9 M^{-1}$, $>10^{10} M^{-1}$, $>10^{11} M^{-1}$, $>10^{12} M^{-1}$, $>10^{13} M^{-1}$, etc.). In certain such embodiments, an antibody is capable of binding different antigens so long as the different antigens comprise that particular epitope. In certain instances, for example, homologous proteins from different species may comprise the same epitope.

As used herein, the term "anti-influenza antibody" refers to an antibody which specifically recognizes an antigen and/or epitope presented by one or more strains of influenza virus. A "cross-reactive influenza antibody" refers to an antibody which specifically recognizes an antigen and/or epitope presented by more than one strain of influenza virus. For example, an "N1/N7 cross-reactive influenza antibody" or "N1/N7 cross-reactive antibody" specifically recognizes an antigen and/or epitope presented by N1 and N7 strains of influenza.

As used herein, the term "monoclonal antibody" refers to an antibody which is a member of a substantially homogeneous population of antibodies that specifically bind to the same epitope. In certain embodiments, a monoclonal antibody is secreted by a hybridoma. In certain such embodiments, a hybridoma is produced according to certain methods known to those skilled in the art. See, e.g., Kohler and Milstein (1975) Nature 256: 495-499; herein incorporated by reference in its entirety. In certain embodiments, a monoclonal antibody is produced using recombinant DNA methods (see, e.g., U.S. Pat. No. 4,816,567). In certain embodiments, a monoclonal antibody refers to an antibody fragment isolated from a phage display library. See, e.g., Clackson et al. (1991) Nature 352: 624-628; and Marks et al. (1991) J. Mol. Biol. 222: 581-597; herein incorporated by reference in their entireties. The modifying word "monoclonal" indicates properties of antibodies obtained from a substantially-homogeneous population of antibodies, and does not limit a method of producing antibodies to a specific method. For various other monoclonal antibody production techniques, see, e.g., Harlow and Lane (1988) Antibodies: A Laboratory Manual (Cold Spring Harbor Laboratory, Cold Spring Harbor, N.Y.); herein incorporated by reference in its entirety.

As used herein, the term "antibody fragment" refers to a portion of a full-length antibody, including at least a portion antigen binding region or a variable region. Antibody fragments include, but are not limited to, Fab, Fab', F(ab')$_2$, Fv, scFv, Fd, diabodies, and other antibody fragments that retain at least a portion of the variable region of an intact antibody. See, e.g., Hudson et al. (2003) Nat. Med. 9:129-134; herein incorporated by reference in its entirety. In certain embodiments, antibody fragments are produced by enzymatic or chemical cleavage of intact antibodies (e.g., papain digestion and pepsin digestion of antibody), produced by recombinant DNA techniques, or chemical polypeptide synthesis.

For example, a "Fab" fragment comprises one light chain and the $C_{H1}$ and variable region of one heavy chain. The heavy chain of a Fab molecule cannot form a disulfide bond with another heavy chain molecule. A "Fab'" fragment comprises one light chain and one heavy chain that comprises additional constant region, extending between the $C_{H1}$ and $C_{H2}$ domains. An interchain disulfide bond can be formed between two heavy chains of a Fab' fragment to form a "F(ab')$_2$" molecule.

An "Fv" fragment comprises the variable regions from both the heavy and light chains, but lacks the constant regions. A single-chain Fv (scFv) fragment comprises heavy and light chain variable regions connected by a flexible linker to form a single polypeptide chain with an antigen-binding region. Exemplary single chain antibodies are discussed in detail in WO 88/01649 and U.S. Pat. Nos. 4,946,778 and 5,260,203; herein incorporated by reference in their entireties. In certain instances, a single variable region (e.g., a heavy chain variable region or a light chain variable region) may have the ability to recognize and bind antigen.

Other antibody fragments will be understood by skilled artisans.

As used herein, the term "chimeric antibody" refers to an antibody made up of components from at least two different sources. In certain embodiments, a chimeric antibody comprises a portion of an antibody derived from a first species fused to another molecule, e.g., a portion of an antibody derived from a second species. In certain such embodiments, a chimeric antibody comprises a portion of an antibody derived from a non-human animal fused to a portion of an antibody derived from a human. In certain such embodiments, a chimeric antibody comprises all or a portion of a variable region of an antibody derived from a non-human animal fused to a constant region of an antibody derived from a human.

A "humanized" antibody refers to a non-human antibody that has been modified so that it more closely matches (in amino acid sequence) a human antibody. A humanized antibody is thus a type of chimeric antibody. In certain embodiments, amino acid residues outside of the antigen binding residues of the variable region of the non-human antibody are modified. In certain embodiments, a humanized antibody is constructed by replacing all or a portion of a complementarity determining region (CDR) of a human antibody with all or a portion of a CDR from another antibody, such as a non-human antibody, having the desired antigen binding specificity. In certain embodiments, a humanized antibody comprises variable regions in which all or substantially all of the CDRs correspond to CDRs of a non-human antibody and all or substantially all of the framework regions (FRs) correspond to FRs of a human antibody. In certain such embodiments, a humanized antibody further comprises a constant region (Fc) of a human antibody.

The term "human antibody" refers to a monoclonal antibody that contains human antibody sequences and does not contain antibody sequences from a non-human animal. In certain embodiments, a human antibody may contain synthetic sequences not found in native antibodies. The term is not limited by the manner in which the antibodies are made. For example, in various embodiments, a human antibody may be made in a transgenic mouse, by phage display, by human B-lymphocytes, or by recombinant methods.

As used herein, the term "natural antibody" refers to an antibody in which the heavy and light chains of the antibody have been made and paired by the immune system of a multicellular organism. For example, the antibodies produced by the antibody-producing cells isolated from a first animal immunized with an antigen are natural antibodies. Natural antibodies contain naturally-paired heavy and light chains. The term "natural human antibody" refers to an antibody in which the heavy and light chains of the antibody have been made and paired by the immune system of a human subject.

Native human light chains are typically classified as kappa and lambda light chains. Native human heavy chains are typically classified as mu, delta, gamma, alpha, or epsilon, and define the antibody's isotype as IgM, IgD, IgG, IgA, and IgE, respectively. IgG has subclasses, including, but not limited to, IgG1, IgG2, IgG3, and IgG4. IgM has subclasses including, but not limited to, IgM1 and IgM2. IgA has subclasses including, but not limited to, IgA1 and IgA2. Within native human light and heavy chains, the variable and constant regions are typically joined by a "J" region of about 12 or more amino acids, with the heavy chain also including a "D" region of about 10 more amino acids. See, e.g., Fundamental Immunology (1989) Ch. 7 (Paul, W., ed., 2nd ed. Raven Press, N.Y.); herein incorporated by reference in its entirety.

The term "neutralizing antibody" or "antibody that neutralizes" refers to an antibody that reduces at least one activity of a polypeptide comprising the epitope to which the antibody specifically binds. In certain embodiments, a neutralizing antibody reduces an activity in vitro and/or in vivo. In some embodiments, by neutralizing the polypeptide comprising the epitope, the neutralizing antibody inhibits the capacity of the organism (or virus) displaying the epitope. For example, an "influenza neutralizing antibody" reduces the capacity of one or more strains of influenza to infect a subject.

The term "antigen-binding site" refers to a portion of an antibody capable of specifically binding an antigen. In certain embodiments, an antigen-binding site is provided by one or more antibody variable regions.

The term "epitope" refers to any polypeptide determinant capable of specifically binding to an immunoglobulin or a T-cell receptor. In certain embodiments, an epitope is a region of an antigen that is specifically bound by an antibody. In certain embodiments, an epitope may include chemically active surface groupings of molecules such as amino acids, sugar side chains, phosphoryl, or sulfonyl groups. In certain embodiments, an epitope may have specific three-dimensional structural characteristics (e.g., a "conformational" epitope) and/or specific charge characteristics.

An epitope is defined as "the same" as another epitope if a particular antibody specifically binds to both epitopes. In certain embodiments, polypeptides having different primary amino acid sequences may comprise epitopes that are the same. In certain embodiments, epitopes that are the same may have different primary amino acid sequences. Different antibodies are said to bind to the same epitope if they compete for specific binding to that epitope.

As used herein, the term "artificial" refers to compositions and systems that are designed or prepared by man, and are not naturally occurring. For example, an artificial polypeptide (e.g., antibody or antibody fragment) or nucleic acid is one comprising a non-natural sequence (e.g., a polypeptide without 100% identity with a naturally-occurring protein or a fragment thereof).

The term "amino acid" refers to natural amino acids, unnatural amino acids, and amino acid analogs, all in their D and L stereoisomers, unless otherwise indicated, if their structures allow such stereoisomeric forms.

Natural amino acids include alanine (Ala or A), arginine (Arg or R), asparagine (Asn or N), aspartic acid (Asp or D), cysteine (Cys or C), glutamine (Gln or Q), glutamic acid (Glu or E), glycine (Gly or G), histidine (His or H), isoleucine (Ile or I), leucine (Leu or L), Lysine (Lys or K), methionine (Met or M), phenylalanine (Phe or F), proline (Pro or P), serine (Ser or S), threonine (Thr or T), tryptophan (Trp or W), tyrosine (Tyr or Y) and valine (Val or V).

Unnatural amino acids include, but are not limited to, azetidinecarboxylic acid, 2-aminoadipic acid, 3-aminoadipic acid, beta-alanine, naphthylalanine ("naph"), aminopropionic acid, 2-aminobutyric acid, 4-aminobutyric acid, 6-aminocaproic acid, 2-aminoheptanoic acid, 2-aminoisobutyric acid, 3-aminoisobutyric acid, 2-aminopimelic acid, tertiary-butylglycine ("tBuG"), 2,4-diaminoisobutyric acid, desmosine, 2,2'-diaminopimelic acid, 2,3-diaminopropionic acid, N-ethylglycine, N-ethylasparagine, homoproline ("hPro" or "homoP"), hydroxylysine, allo-hydroxylysine, 3-hydroxyproline ("3Hyp"), 4-hydroxyproline ("4Hyp"), isodesmosine, allo-isoleucine, N-methylalanine ("MeAla" or "Nime"), N-alkylglycine ("NAG") including N-methylglycine, N-methylisoleucine, N-alkylpentylglycine ("NAPG") including N-methylpentylglycine. N-methylvaline, naphthylalanine, norvaline ("Norval"), norleucine ("Norleu"), octylglycine ("OctG"), ornithine ("Orn"), pentylglycine ("pG" or "PGly"), pipecolic acid, thioproline ("ThioP" or "tPro"), homoLysine ("hLys"), and homoArginine ("hArg").

The term "amino acid analog" refers to a natural or unnatural amino acid where one or more of the C-terminal carboxy group, the N-terminal amino group and side-chain functional group has been chemically blocked, reversibly or irreversibly, or otherwise modified to another functional group. For example, aspartic acid-(beta-methyl ester) is an amino acid analog of aspartic acid; N-ethylglycine is an amino acid analog of glycine; or alanine carboxamide is an amino acid analog of alanine. Other amino acid analogs include methionine sulfoxide, methionine sulfone, S-(carboxymethyl)-cysteine, S-(carboxymethyl)-cysteine sulfoxide and S-(carboxymethyl)-cysteine sulfone.

As used herein, the term "artificial polypeptide", "artificial antibody", or "artificial binding agent", consistent with the definition of "artificial" above, refers to a polypeptide, antibody, or binding agent having a distinct amino acid sequence or chemical makeup from those found in natural polypeptides, antibodies, and binding agents. An artificial polypeptide or antibody is not a subsequence of a naturally occurring protein, either the wild-type (i.e., most abundant) or mutant versions thereof. An "artificial polypeptide", "artificial antibody", or "artificial binding agent", as used herein, may be produced or synthesized by any suitable method (e.g., recombinant expression, chemical synthesis, enzymatic synthesis, purification from whole animal, etc.).

As used herein, a "conservative" amino acid substitution refers to the substitution of an amino acid in a peptide or polypeptide with another amino acid having similar chemical properties, such as size or charge. For purposes of the present disclosure, each of the following eight groups contains amino acids that are conservative substitutions for one another:

1) Alanine (A) and Glycine (G);
2) Aspartic acid (D) and Glutamic acid (E);
3) Asparagine (N) and Glutamine (Q);
4) Arginine (R) and Lysine (K);
5) Isoleucine (I), Leucine (L), Methionine (M), and Valine (V);
6) Phenylalanine (F), Tyrosine (Y), and Tryptophan (W);
7) Serine (S) and Threonine (T); and
8) Cysteine (C) and Methionine (M).

Naturally occurring residues may be divided into classes based on common side chain properties, for example: polar positive (histidine (H), lysine (K), and arginine (R)); polar negative (aspartic acid (D), glutamic acid (E)); polar neutral (serine (S), threonine (T), asparagine (N), glutamine (Q)); non-polar aliphatic (alanine (A), valine (V), leucine (L), isoleucine (I), methionine (M)); non-polar aromatic (phenylalanine (F), tyrosine (Y), tryptophan (W)); proline and glycine; and cysteine. As used herein, a "semi-conservative" amino acid substitution refers to the substitution of an amino acid in a peptide or polypeptide with another amino acid within the same class.

In some embodiments, unless otherwise specified, a conservative or semi-conservative amino acid substitution may also encompass non-naturally occurring amino acid residues that have similar chemical properties to the natural residue. These non-natural residues are typically incorporated by chemical peptide synthesis rather than by synthesis in biological systems. These include, but are not limited to, peptidomimetics (e.g., chemically modified peptides, peptoids (side chains are appended to the nitrogen atom of the peptide backbone, rather than to the α-carbons), β-peptides (amino group bonded to the β carbon rather than the a carbon), etc.) and other reversed or inverted forms of amino acid moieties. Embodiments herein may, in some embodiments, be limited to natural amino acids, non-natural amino acids, and/or amino acid analogs.

Non-conservative substitutions may involve the exchange of a member of one class for a member from another class.

As used herein, the term "sequence identity" refers to the degree to which two polymer sequences (e.g., peptide, polypeptide, nucleic acid, etc.) have the same sequential composition of monomer subunits. The term "sequence similarity" refers to the degree with which two polymer sequences (e.g., peptide, polypeptide, nucleic acid, etc.) have similar polymer sequences. For example, similar amino acids are those that share the same biophysical characteristics and can be grouped into the families (see above). The "percent sequence identity" (or "percent sequence similarity") is calculated by: (1) comparing two optimally aligned sequences over a window of comparison (e.g., the length of the longer sequence, the length of the shorter sequence, a specified window, etc.), (2) determining the number of positions containing identical (or similar) monomers (e.g., same amino acids occurs in both sequences, similar amino acid occurs in both sequences) to yield the number of matched positions, (3) dividing the number of matched positions by the total number of positions in the comparison window (e.g., the length of the longer sequence, the length of the shorter sequence, a specified window), and (4) multiplying the result by 100 to yield the percent sequence identity or percent sequence similarity. For example, if peptides A and B are both 20 amino acids in length and have identical amino acids at all but 1 position, then peptide A and peptide B have 95% sequence identity. If the amino acids at the non-identical position shared the same biophysical characteristics (e.g., both were acidic), then peptide A and peptide B would have 100% sequence similarity. As another example, if peptide C is 20 amino acids in length and peptide D is 15 amino acids in length, and 14 out of 15 amino acids in peptide D are identical to those of a portion of peptide C, then peptides C and D have 70% sequence identity, but peptide D has 93.3% sequence identity to an optimal comparison window of peptide C. For the purpose of calculating "percent sequence identity" (or "percent sequence similarity") herein, any gaps in aligned sequences are treated as mismatches at that position.

Any polypeptides described herein as having a particular percent sequence identity or similarity (e.g., at least 70%) with a reference sequence ID number, may also be expressed as having a maximum number of substitutions (or terminal deletions) with respect to that reference sequence.

The term "effective dose" or "effective amount" refers to an amount of an agent, e.g., a neutralizing antibody, that results in the reduction of symptoms in a patient or results in a desired biological outcome. In certain embodiments, an effective dose or effective amount is sufficient to reduce or inhibit the infectivity of one or more strains of influenza.

As used herein, the terms "administration" and "administering" refer to the act of giving a drug, prodrug, or other agent, or therapeutic to a subject or in vivo, in vitro, or ex vivo cells, tissues, and organs. Exemplary routes of administration to the human body can be through space under the arachnoid membrane of the brain or spinal cord (intrathecal), the eyes (ophthalmic), mouth (oral), skin (topical or transdermal), nose (nasal), lungs (inhalant), oral mucosa (buccal), ear, rectal, vaginal, by injection (e.g., intravenously, subcutaneously, intratumorally, intraperitoneally, etc.) and the like.

The term "treatment" encompasses both therapeutic and prophylactic/preventative measures unless otherwise indicated. Those in need of treatment include, but are not limited to, individuals already having a particular condition (e.g., influenza infection) as well as individuals who are at risk of acquiring a particular condition or disorder (e.g., those needing prophylactic/preventative measures, those at risk of influenza exposure, those at risk of having particularly bad outcomes from influenza infection, etc.). The term "treating" refers to administering an agent to a subject for therapeutic and/or prophylactic/preventative purposes.

A "therapeutic agent" refers to an agent that may be administered in vivo to bring about a therapeutic and/or prophylactic/preventative effect.

A "therapeutic antibody" refers to an antibody that may be administered in vivo to bring about a therapeutic and/or prophylactic/preventative effect.

As used herein, the terms "co-administration" and "co-administering" refer to the administration of at least two agent(s) or therapies to a subject. In some embodiments, the co-administration of two or more agents or therapies is concurrent. In other embodiments, a first agent/therapy is administered prior to a second agent/therapy. Those of skill in the art understand that the formulations and/or routes of administration of the various agents or therapies used may vary. The appropriate dosage for co-administration can be readily determined by one skilled in the art. In some embodiments, when agents or therapies are co-administered, the respective agents or therapies are administered at lower dosages than appropriate for their administration alone. Thus, co-administration is especially desirable in embodiments where the co-administration of the agents or therapies lowers the requisite dosage of a potentially harmful (e.g., toxic) agent(s), and/or when co-administration of two or more agents results in sensitization of a subject to beneficial effects of one of the agents via co-administration of the other agent.

As used herein, the term pharmaceutical composition" refers to the combination of an active agent (e.g., binding agent) with a carrier, inert or active, making the composition especially suitable for diagnostic or therapeutic use in vitro, in vivo or ex vivo.

The terms "pharmaceutically acceptable" or "pharmacologically acceptable," as used herein, refer to compositions that do not substantially produce adverse reactions, e.g., toxic, allergic, or immunological reactions, when administered to a subject.

As used herein, the term "pharmaceutically acceptable carrier" refers to any of the standard pharmaceutical carriers including, but not limited to, phosphate buffered saline solution, water, emulsions (e.g., such as an oil/water or water/oil emulsions), and various types of wetting agents, any and all solvents, dispersion media, coatings, sodium lauryl sulfate, isotonic and absorption delaying agents, disintigrants (e.g., potato starch or sodium starch glycolate), and the like. The compositions also can include stabilizers and preservatives. For examples of carriers, stabilizers and adjuvants, see, e.g., Martin, Remington's Pharmaceutical Sciences, 15th Ed., Mack Publ. Co., Easton, Pa. (1975), incorporated herein by reference in its entirety.

DETAILED DESCRIPTION

Provided herein are anti-neuraminidase agents useful for neutralization of influenza virus, and methods of use and manufacture thereof. In particular, compositions comprising anti-neuraminidase agents (e.g., antibodies) that are cross-reactive with multiple influenza strains are provided, as well as methods of treatment and prevention of influenza infection therewith.

Antibodies to the hemagglutinin (HA) and neuraminidase (NA) glycoproteins are the major mediators of protection against influenza virus infection. Experiments conducted during development of embodiments herein demonstrate that available influenza vaccines poorly display key NA epitopes and rarely induce NA-reactive B cells. Conversely, influenza virus infection induces NA-reactive B cells at a frequency that approaches (H1N1) or exceeds (H3N2) that of HA-reactive B cells. NA-reactive antibodies display broad binding activity spanning the entire history of influenza A virus circulation in humans, including the original pandemic strains of both H1N1 and H3N2 subtypes. The antibodies robustly inhibit the enzymatic activity of NA, including oseltamivir-resistant variants, and provide robust prophylactic protection in vivo, including against avian H5N1 viruses. When used therapeutically, NA-reactive antibodies protected mice from lethal influenza virus challenge even 48-hours post-infection. These findings indicate that influenza vaccines optimized to improve targeting of NA provide durable and broad protection against divergent influenza strains.

NA is an important target for antivirals or therapeutics, due to its critical role in the influenza virus replication cycle (Wohlbold and Krammer, 2014; herein incorporated by reference in its entirety). Inhibition of NA activity is the basis of commonly used influenza therapeutics including oseltamivir (TAMIFLU), zanamivir (RELENZA), laninamivir (INAVIR), and peramivir (RAPIVAB). Oseltamivir reduces the median duration of influenza illness by 1.3 days and markedly reduces symptoms compared to placebo if given within 48 hours of symptom onset. In a prophylactic study, oseltamivir decreased rates of influenza infection five-fold from 5% (25/519) for the placebo group to 1% (6/520) for the oseltamivir-treated group (Genentech, 2016; herein incorporated by reference in its entirety). Thus, inhibition of NA activity has become a standard of care for the treatment of influenza virus infections. The limitations of neuraminidase inhibitors such as oseltamivir are that resistant strains of influenza virus have readily emerged (Dharan et al., 2009; herein incorporated by reference in its entirety) and the window for efficacy is limited to the first 48 hours of symptom onset. There are several mechanisms of NA-reactive antibody inhibition of influenza virus infection (Krammer and Palese, 2015; herein incorporated by reference in its entirety). NA-reactive antibodies bind to influenza virus infected cells and prevent virus budding and viral egress. These antibodies similarly inhibit viral escape from the natural defense proteins that trap the virus via HA-sialic acid interactions on mucosal surfaces. Moreover, NA-reactive antibody bound to NA at the surface of infected cells aids in the clearance of the virus through antibody-dependent cell-mediated cytotoxicity (ADCC) and complement-dependent cytotoxicity (CDC) (Wan et al., 2013; Wohlbold et al., 2017; herein incorporated by reference in their entireties). The polyclonal antibody response to NA is broadly reactive and conferrs protection against heterologous viruses in mice (Schulman et al., 1968; herein incorporated by reference in its entirety). This cross-reactivity is evident even when there is substantial change within strain specific NA epitopes, resulting in a phenomenon of one-way drift (Sandbulte et al., 2011; herein incorporated by reference in its entirety). NA-reactive monoclonal antibodies (mAbs) isolated from mice and rabbits protected against both homologous and heterologous influenza infection in vivo (Doyle et al., 2013; Wan et al., 2013; Wan et al., 2015; Wilson et al., 2016; Wohlbold et al., 2017; herein incorporated by reference in their entireties). Several conserved amino acids were identified in these studies as the basis for the broad reactivity of NA-reactive mAbs against influenza A or B viruses (Wan et al., 2013; Wohlbold et al., 2017; herein incorporated by reference in their entireties). Studies in humans have also shown that pre-existing NA-reactive antibodies reduce the number of cases of infection and decrease disease severity from a naturally circulating virus (Monto and Kendal, 1973; Murphy et al., 1972; herein incorporated by reference in its entirety). However, little is known about human antibody responses to NA, and most influenza vaccine development efforts both past and present are focused on targeting HA.

Experiments conducted during development of embodiments herein demonstrate that, unlike vaccination, natural influenza virus infection readily induces a high proportion of NA-reactive B cells. Thus, from infected patients, protective antibodies that bind NA epitopes were isolated and characterized, informing on the design of an NA-based component for influenza vaccination. The NA-reactive antibodies are inducible in human or mouse by infection or immunization with whole virions, but bind epitopes not efficiently detected in the FLUARIX or FLUZONE influenza vaccines. These NA-reactive mAbs bind a broad spectrum of influenza virus strains, often spanning the entire circulation history in humans for that NA group. Moreover, these antibodies have robust NA inhibition (NI) activity and provide prophylactic as well as therapeutic protection in vivo. Experiments conducted during development of embodiments herein provide next-generation influenza vaccines should that are optimized to improve the NA humoral immune response to induce broadly cross-reactive and protective NA-reactive antibody responses.

The results presented herein demonstrate that NA induces a potent, broadly cross-reactive, and protective humoral immune response (e.g., with the right immunogen). The NA-reactive mAbs were more broadly reactive, the potency of protection and neutralization rivaled that of HA-reactive mAbs, and for H3N2 infections there were more NA-reactive than HA-reactive B cells activated. This response is consistent with a recent report that by molar composition, NA is the most immunogenic influenza protein (Angeletti and Yewdell, 2017; herein incorporated by reference in its entirety). The relative conservation of NA epitopes (Sandbulte et al., 2011; herein incorporated by reference in its entirety) also drives a back-boost effect against NAs of historical isolates (Rajendran et al., 2017; herein incorporated by reference in its entirety). In contrast, after vaccination, experiments conducted during development of embodiments herein demonstrate that there is only a 1:87 ratio of NA to HA plasmablasts activated (FIG. 1E). The NA-reactive mAbs induced by infection reported here have substantially reduced binding to the inactivated vaccines tested, indicating that the vaccines do not efficiently present important conserved and protective NA epitopes. This observation is explained by several factors. Firstly, the inactivated influenza vaccines are optimized only for the HA antigen, as the FDA requires that licensed influenza virus vaccines contain at least 15 lag of each HA subtype (Air, 2012; herein incorporated by reference in its entirety). Secondly, antigenic competition between HA and NA may affect the NA humoral immune response (Johansson et al., 1987; herein incorporated by reference in its entirety). However, this mechanism did not appear to preclude the response to NA during infection or to whole virions in mice as reported above. Thirdly, although influenza vaccine compositions contain varying amounts of NA (Wohlbold et al., 2015; herein incorporated by reference in its entirety), it is unclear if the NA antigen retains its natural tetramer structure, which is important to maintain immunogenicity (Johansson and Cox, 2011; herein incorporated by reference in its entirety). Conversely, during an influenza virus infection, NA replicates along with the virus so that B cells can respond to intact NA on whole virions and infected cells.

The rate of NA antigenic drift is slower than that of HA, which explains the high frequency of broadly cross-reactive antibodies (Sandbulte et al., 2011; herein incorporated by reference in its entirety). The NA-reactive mAbs isolated herein typically cross-bind to heterologous NA proteins from most human influenza A virus strains and a subset also bound to avian H5N1, H7N9 and had reactivity to H7N3, H4N4, and H3N8 strains. This breadth was evident for the antibodies that were used to map the epitopes. On N1, two of the primary amino acids targeted (N309 and N273) are 99.7% conserved (present in 6835 of 6855 strains) in H1N1 virus from 1918 to 2017 H1N1 strain in the United States (www.fludb.org; herein incorporated by reference in its entirety). Also, N1-reactive mAbs that selected changes at two conserved epitopes (G249 and N273) shared between the human and avian strains were able to mediate prophylactic protection against H5N1 challenge in vivo in mice. Five of the N2-reactive mAbs bind to the conserved enzymatic active site on the head of the NA. The broad reactivity and conservation of the targeted epitopes suggest that NA may be an essential component of universal influenza virus vaccine compositions.

Both NA-inhibiting and non-inhibiting mAbs to either N1 or N2 protected from influenza virus challenge in vivo. Inhibition of viral egress from infected cells or inhibition of release from mucins are the appreciated mechanisms of action of NA-inhibiting antibodies (Krammer and Palese, 2015; herein incorporated by reference in its entirety). For non-NI mAbs, there are several mechanisms that account for protection. Fc-FcR interactions have been shown to be required for full protection by some NA-reactive mAbs (DiLillo et al., 2016; Henry Dunand et al., 2016; Wohlbold et al., 2017; herein incorporated by reference in their entireties). Although not all of the protective NA-reactive mAbs were neutralizing in vitro, most had some degree of NA-inhibiting activity. Thus, the NA-reactive mAbs may also alter the functional balance of opposing actions between HA and NA to disrupt efficient viral replication (Benton et al., 2015; Wagner et al., 2002; herein incorporated by reference in their entireties).

In some cases, infection with influenza virus induces broader and longer lasting protection than vaccination (Margine et al., 2013a; Nachbagauer et al., 2017; Wrammert et al., 2011; herein incorporated by reference in their entireties). NA inhibiting antibody titers are recognized as a correlate of protection (Clements et al., 1986; herein incorporated by reference in its entirety). Adult influenza virus challenge studies showed that antibodies inhibiting NA but not HA are associated with reduced severity and duration of illness (Memoli et al., 2016 herein incorporated by reference in its entirety). This observation explains why HA and NA inhibiting antibodies are independent correlates of vaccine effectiveness (Monto et al., 2015; herein incorporated by reference in its entirety). Experiments conducted during development of embodiments herein demonstrate that part of such protection is mediated by polyclonal NA-reactive antibodies that are not efficiently induced by vaccination.

There are obstacles to exploiting the broadly cross-reactive and protective response to NA for improving influenza virus vaccines. The immunogenicity of NA is strain-dependent (Sultana et al., 2014; herein incorporated by reference in its entirety) and the stability of NAs of each of the vaccine strains differ when subjected to various destabilizing agents. Using recombinant NA to induce an NA-based immune response is one solution (Krammer and Palese, 2015; herein incorporated by reference in its entirety), but the NA immunogens need to be in tetrameric form for optimal immunogenicity. It is challenging to keep the native structure of NA within vaccine formulations (Brett and Johansson, 2006;

Eichelberger and Wan, 2015; herein incorporated by reference in their entireties). Another solution is the use of live-attenuated vaccines that express NA on their surface and the surface of infected cells. The findings described herein demonstrate that optimized NA content and structural integrity in influenza vaccines induces a broadly cross-reactive and protective anti-NA response.

NA-reactive antibodies are readily or even dominantly induced, protecting levels comparable to HA-reactive antibodies, but with increased breadth. The data presented herein indicates that inclusion of an improved NA component to influenza vaccine compositions reduced the severity of infections. In some embodiments, the degree of protection conferred protects across most (e.g., all) influenza infections occurring at all, and in certain embodiments provides broad-ranging protection against pandemic strains that express, for example, N1 or N2 NAs.

Some embodiments described herein relate to antibodies, and antigen binding fragments thereof, that specifically bind to epitopes on the NA protein (e.g., N1, N2, N3, N4, N5, N6, N7, N8, N9, N10, N11) of one or more strains of influenza. Embodiments also relate to nucleic acids that encode, immortalized B cells and cultured single plasma cells that produce, and to epitopes that bind, to such antibodies and antibody fragments. In some embodiments, provided herein are vaccines comprising the antibodies and antigen binding fragments described herein. In addition, described herein is the use of the antibodies, antibody fragments, and epitopes in screening methods as well as in the diagnosis, treatment and prevention of influenza virus infection.

In an exemplary embodiment, an antibody or an antibody fragment thereof is provided that binds an epitope on two or more (e.g., 3, 4, 5, 6, 7, 8, 9, 10, 11, or ranges therebetween) NA types (e.g., N1, N2, N3, N4, N5, N6, N7, N8, N9, N10, N11) and thereby treats or prevents infection by two or more types of influenza virus (e.g. H1N1, H3N2, H5N1, H7N1, H7N7, H9N2, etc.). Treatment/prevention of infection by other exemplary combinations of subtypes of influenza A virus is also provided.

In some embodiments, an antibody or antibody fragment comprises a heavy chain variable region having an amino acid sequence that is about 70%, 75%, 80%, 85%, 90%, 95%, 97%, 98%, 99% or 100% identical (or any ranges therein) to the sequence recited in any one of SEQ ID NOs: 2, 18, 34, 50, 66, 82, 98, 114, 130, 146, 162, 178, 194, 209, 217, or 225. In some embodiments, an antibody or antibody fragment comprises a heavy chain variable region having >50%, >60%, >70%, >75%, >80%, >85%, >90%, >95%, >97%, >98%, >99% or 100% sequence similarity (or any ranges therein) to one of SEQ ID NOs: 2, 18, 34, 50, 66, 82, 98, 114, 130, 146, 162, 178, 194, 209, 217, or 225. In another embodiment, an antibody or antibody fragment of the invention comprises a light chain variable region having an amino acid sequence that is about 70%, 75%, 80%, 85%, 90%, 95%, 97%, 98%, 99% or 100% identical (or any ranges therein) to the sequence recited in SEQ ID NOs: 10, 26, 42, 58, 74, 90, 106, 122, 138, 154, 170, 186, 202, 213, 221, or 229. In some embodiments, an antibody or antibody fragment comprises a light chain variable region having >50%, >60%, >70%, >75%, >80%, >85%, >90%, >95%, >97%, >98%, >99% or 100% sequence similarity (or any ranges therein) to one of SEQ ID NOs: 10, 26, 42, 58, 74, 106, 122, 138, 154, 170, 186, 202, 213, 221, or 229.

In some embodiments, an antibody or antibody fragment exhibits all or a portion of the epitope binding affinity of one of 228-14-035-2D04, 229-14-036-1D05, 229-14-036-1G03, 229-14-036-2B04, 229-14-036-2C06, 235-15-042-1E06, 1000-2E06, 294-16-009-A-1C02, 294-16-009-A-1C06, 294-16-009-A-1D05, 294-16-009-G-1F01, 296-16-003-G-2F04, 300-16-005-G-2A04, 229-1D02, 229-1F06, and/or 229-2D03. In some embodiments, an antibody or antibody fragment binds the same epitope as one of 228-14-035-2D04, 229-14-036-1D05, 229-14-036-1G03, 229-14-036-2B04, 229-14-036-2C06, 235-15-042-1E06, 1000-2E06, 294-16-009-A-1C02, 294-16-009-A-1C06, 294-16-009-A-1D05, 294-16-009-G-1F01, 296-16-003-G-2F04, 300-16-005-G-2A04, 229-1D02, 229-1F06, and/or 229-2D03. In some embodiments, an antibody or antibody fragment exhibits the influenza neutralizing activity of one of 228-14-035-2D04, 229-14-036-1D05, 229-14-036-1G03, 229-14-036-2B04, 229-14-036-2C06, 235-15-042-1E06, 1000-2E06, 294-16-009-A-1C02, 294-16-009-A-1C06, 294-16-009-A-1D05, 294-16-009-G-1F01, 296-16-003-G-2F04, 300-16-005-G-2A04, 229-1D02, 229-1F06, and/or 229-2D03. In some embodiments, an antibody or antibody fragment neutralizes the same influenza strains as one of 228-14-035-2D04, 229-14-036-1D05, 229-14-036-1G03, 229-14-036-2B04, 229-14-036-2C06, 235-15-042-1E06, 1000-2E06, 294-16-009-A-1C02, 294-16-009-A-1C06, 294-16-009-A-1D05, 294-16-009-G-1F01, 296-16-003-G-2F04, 300-16-005-G-2A04, 229-1D02, 229-1F06, and/or 229-2D03. In some embodiments, an antibody is not a natural antibody. In some embodiments, an antibody is not a natural human antibody.

The CDRs of the antibody heavy chains are referred to as CDRH1 (or HCDR1), CDRH2 (or HCDR2) and CDRH3 (or HCDR3), respectively. Similarly, the CDRs of the antibody light chains are referred to either as CDRK1 (or KCDR1), CDRK2 (or KCDR1) and CDRK3 (or KCDR1), or CDRL1 (or LCDR1), CDRL2 (or LCDR1) and CDRL3 (or LCDR1), respectively. In some embodiments, antibodies or antibody fragments are provided with heavy chain CDR1 corresponding to one of SEQ ID NOs: 4, 20, 36, 52, 68, 84, 100, 116, 132, 148, 164, 180, or 196. In some embodiments, antibodies or antibody fragments are provided with heavy chain CDR2 corresponding to one of SEQ ID NOs: 6, 22, 38, 54, 70, 86, 102, 118, 134, 150, 166, 182, 198. In some embodiments, antibodies or antibody fragments are provided with heavy chain CDR3 corresponding to one of SEQ ID NOs: 8, 24, 40, 56, 72, 88, 104, 120, 136, 152, 168, 184, 200. In some embodiments, antibodies or antibody fragments are provided with light chain CDRs corresponding to one or SEQ ID NOs: 22-24, 28-30, or 40-42. In some embodiments, antibodies or antibody fragments are provided with light chain CDR1 corresponding to one of SEQ ID NOs: 12, 28, 44, 60, 76, 92, 108, 124, 140, 156, 172, 188, 204. In some embodiments, antibodies or antibody fragments are provided with light chain CDR2 corresponding to one of SEQ ID NOs: 14, 30, 46, 62, 78, 94, 110, 126, 142, 158, 174, 190, 206. In some embodiments, antibodies or antibody fragments are provided with light chain CDR3 corresponding to one of SEQ ID NOs: 16, 32, 48, 64, 80, 96, 112, 128, 144, 160, 176, 192, 208. In some embodiments, CDRs are provided having at least 70% sequence identity (e.g., 70%, 75%, 80%, 85%, 90%, 95%, 98%, 99%, 100%, and any ranges with such endpoints (e.g., 70-100%, 80-100%, 85-99%, 90-99%, etc.)) with one of SEQ ID NOs: 4, 20, 36, 52, 68, 84, 100, 116, 132, 148, 164, 180, 196, 6, 22, 38, 54, 70, 86, 102, 118, 134, 150, 166, 182, 198, 8, 24, 40, 56, 72, 88, 104, 120, 136, 152, 168, 184, 200, 12, 28, 44, 60, 76, 92, 108, 124, 140, 156, 172, 188, 204, 14, 30, 46, 62, 78, 94, 110, 126, 142, 158, 174, 190, 206, 16, 32, 48, 64, 80, 96, 112, 128, 144, 160, 176, 192, and/or 208. In some embodiments, CDRs are provided having at least 50% sequence similarity (e.g., 50%, 60%, 70%, 75%, 80%, 85%, 90%, 95%, 98%, 99%, 100%, and any ranges with such endpoints (e.g., 50-100%, 80-100%, 85-99%, 90-99%, etc.)) with one of SEQ ID NOs: 4, 20, 36, 52, 68, 84, 100, 116, 132, 148, 164, 180, 196, 6, 22, 38, 54, 70, 86, 102, 118, 134, 150, 166, 182, 198, 8, 24, 40, 56, 72, 88, 104, 120, 136, 152, 168, 184, 200, 12, 28, 44, 60, 76, 92, 108, 124, 140, 156, 172, 188, 204, 14, 30, 46, 62, 78, 94, 110, 126, 142, 158, 174, 190, 206, 16, 32, 48, 64, 80, 96, 112, 128, 144, 160, 176, 192, and/or 208. In some embodiments, CDRs (or a combination thereof) are provided that recognize the same HA epitopes as 228-14-035-2D04, 229-14-036-1D05, 229-14-036-1G03, 229-14-036-2B04, 229-14-036-2C06, 235-15-042-1E06, 1000-2E06, 294-16-009-A-1C02, 294-16-009-A-1C06, 294-16-009-A-1D05, 294-16-009-G-1F01, 296-16-003-G-2F04, 300-16-005-G-2A04, 229-1D02, 229-1F06, and/or 229-2D03.

In certain embodiments, an antibody or antigen binding fragment comprises the light chain CDRs, heavy chain CDRs, or all of the CDRs of antibody 228-14-035-2D04 (SEQ ID NOs: 4, 6, 8, 12, 14, and 16), and neutralizes influenza virus infection. In some embodiments, an antibody or antigen binding fragment comprises CDRs with at least 70% sequence identity (e.g., >70%, >75%, >80%, >85%, >90%, >95%, >97%, >98%, >99% or 100%, and ranges therein) and/or at least 50% sequence similarity (e.g., >50%, >60%, >70%, >75%, >80%, >85%, >90%, >95%, >97%, >98%, >99% or 100%, and ranges therein) with the CDRs of antibody 228-14-035-2D04 (SEQ ID NOs: 4, 6, 8, 12, 14, and 16), binds the epitope(s) of antibody 228-14-035-2D04, and/or neutralizes influenza virus infection.

In certain embodiments, an antibody or antigen binding fragment comprises all of the CDRs of antibody 229-14-036-1D05 (SEQ ID NOs: 20, 22, 24, 28, 30, and 32), and neutralizes influenza virus infection. In some embodiments, an antibody or antigen binding fragment comprises CDRs with at least 70% sequence identity (e.g., >70%, >75%, >80%, >85%, >90%, >95%, >97%, >98%, >99% or 100%, and ranges therein) and/or at least 50% sequence similarity (e.g., >50%, >60%, >70%, >75%, >80%, >85%, >90%, >95%, >97%, >98%, >99% or 100%, and ranges therein) with the CDRs of antibody 229-14-036-1D05 (SEQ ID NOs: 20, 22, 24, 28, 30, and 32), binds the epitope(s) of antibody 229-14-036-1D05, and/or neutralizes influenza virus infection.

In certain embodiments, an antibody or antigen binding fragment comprises all of the CDRs of antibody 229-14-036-1G03 (SEQ ID NOs: 36, 38, 40, 44, 46, and 48), and neutralizes influenza virus infection. In some embodiments, an antibody or antigen binding fragment comprises CDRs with at least 70% sequence identity (e.g., >70%, >75%, >80%, >85%, >90%, >95%, >97%, >98%, >99% or 100%, and ranges therein) and/or at least 50% sequence similarity (e.g., >50%, >60%, >70%, >75%, >80%, >85%, >90%, >95%, >97%, >98%, >99% or 100%, and ranges therein) with the CDRs of antibody 229-14-036-1G03 (SEQ ID NOs: 36, 38, 40, 44, 46, and 48), binds the epitope(s) of antibody 229-14-036-1G03, and/or neutralizes influenza virus infection.

In certain embodiments, an antibody or antigen binding fragment comprises all of the CDRs of antibody 229-14-036-2B04 (SEQ ID NOs: 52, 54, 56, 60, 62, and 64), and neutralizes influenza virus infection. In some embodiments, an antibody or antigen binding fragment comprises CDRs with at least 70% sequence identity (e.g., >70%, >75%, >80%, >85%, >90%, >95%, >97%, >98%, >99% or 100%, and ranges therein) and/or at least 50% sequence similarity (e.g., >50%, >60%, >70%, >75%, >80%, >85%, >90%, >95%, >97%, >98%, >99% or 100%, and ranges therein) with the CDRs of antibody 229-14-036-2B04 (SEQ ID NOs: 52, 54, 56, 60, 62, and 64), binds the epitope(s) of antibody 229-14-036-2B04, and/or neutralizes influenza virus infection.

In certain embodiments, an antibody or antigen binding fragment comprises all of the CDRs of antibody 229-14-036-2C06 (SEQ ID NOs: 68, 70, 72, 76, 78, and 80), and neutralizes influenza virus infection. In some embodiments, an antibody or antigen binding fragment comprises CDRs with at least 70% sequence identity (e.g., >70%, >75%, >80%, >85%, >90%, >95%, >97%, >98%, >99% or 100%, and ranges therein) and/or at least 50% sequence similarity (e.g., >50%, >60%, >70%, >75%, >80%, >85%, >90%, >95%, >97%, >98%, >99% or 100%, and ranges therein) with the CDRs of antibody 229-14-036-2C06 (SEQ ID NOs: 68, 70, 72, 76, 78, and 80), binds the epitope(s) of antibody 229-14-036-2C06, and/or neutralizes influenza virus infection.

In certain embodiments, an antibody or antigen binding fragment comprises the light chain CDRs, heavy chain CDRs, or all of the CDRs of antibody 235-15-042-1E06 (SEQ ID NOs: 84, 86, 88, 92, 94, and 96), and neutralizes influenza virus infection. In some embodiments, an antibody or antigen binding fragment comprises CDRs with at least 70% sequence identity (e.g., >70%, >75%, >80%, >85%, >90%, >95%, >97%, >98%, >99% or 100%, and ranges therein) and/or at least 50% sequence similarity (e.g., >50%, >60%, >70%, >75%, >80%, >85%, >90%, >95%, >97%, >98%, >99% or 100%, and ranges therein) with the CDRs of antibody 235-15-042-1E06 (SEQ ID NOs: 84, 86, 88, 92, 94, and 96), binds the epitope(s) of antibody 235-15-042-1E06, and/or neutralizes influenza virus infection.

In certain embodiments, an antibody or antigen binding fragment comprises the light chain CDRs, heavy chain CDRs, or all of the CDRs of antibody 1000-2E06 (SEQ ID NOs: 100, 102, 104, 108, 110, and 112), and neutralizes influenza virus infection. In some embodiments, an antibody or antigen binding fragment comprises CDRs with at least 70% sequence identity (e.g., >70%, >75%, >80%, >85%, >90%, >95%, >97%, >98%, >99% or 100%, and ranges therein) and/or at least 50% sequence similarity (e.g., >50%, >60%, >70%, >75%, >80%, >85%, >90%, >95%, >97%, >98%, >99% or 100%, and ranges therein) with the CDRs of antibody 1000-2E06 (SEQ ID NOs: 84, 86, 88, 92, 94, and 96), binds the epitope(s) of antibody 1000-2E06, and/or neutralizes influenza virus infection.

In certain embodiments, an antibody or antigen binding fragment comprises the light chain CDRs, heavy chain CDRs, or all of the CDRs of antibody 294-16-009-A-1C02 (SEQ ID NOs: 116, 118, 120, 124, 126, and 128), and neutralizes influenza virus infection. In some embodiments, an antibody or antigen binding fragment comprises CDRs with at least 70% sequence identity (e.g., >70%, >75%, >80%, >85%, >90%, >95%, >97%, >98%, >99% or 100%, and ranges therein) and/or at least 50% sequence similarity (e.g., >50%, >60%, >70%, >75%, >80%, >85%, >90%, >95%, >97%, >98%, >99% or 100%, and ranges therein) with the CDRs of antibody 294-16-009-A-1C02 (SEQ ID NOs: 116, 118, 120, 124, 126, and 128), binds the epitope(s) of antibody 294-16-009-A-1C02, and/or neutralizes influenza virus infection.

In certain embodiments, an antibody or antigen binding fragment comprises the light chain CDRs, heavy chain CDRs, or all of the CDRs of antibody 294-16-009-A-1C06 (SEQ ID NOs: 132, 134, 136, 140, 142, and 144), and neutralizes influenza virus infection. In some embodiments, an antibody or antigen binding fragment comprises CDRs with at least 70% sequence identity (e.g., >70%, >75%, >80%, >85%, >90%, >95%, >97%, >98%, >99% or 100%, and ranges therein) and/or at least 50% sequence similarity (e.g., >50%, >60%, >70%, >75%, >80%, >85%, >90%, >95%, >97%, >98%, >99% or 100%, and ranges therein) with the CDRs of antibody 294-16-009-A-1C06 (SEQ ID NOs: 132, 134, 136, 140, 142, and 144), binds the epitope(s) of antibody 294-16-009-A-1C06, and/or neutralizes influenza virus infection.

In certain embodiments, an antibody or antigen binding fragment comprises the light chain CDRs, heavy chain CDRs, or all of the CDRs of antibody 294-16-009-A-1D05 (SEQ ID NOs: 148, 150, 152, 156, 158, and 160), and neutralizes influenza virus infection. In some embodiments, an antibody or antigen binding fragment comprises CDRs with at least 70% sequence identity (e.g., >70%, >75%, >80%, >85%, >90%, >95%, >97%, >98%, >99% or 100%, and ranges therein) and/or at least 50% sequence similarity (e.g., >50%, >60%, >70%, >75%, >80%, >85%, >90%, >95%, >97%, >98%, >99% or 100%, and ranges therein) with the CDRs of antibody 294-16-009-A-1D05 (SEQ ID NOs: 148, 150, 152, 156, 158, and 160), binds the epitope(s) of antibody 294-16-009-A-1D05, and/or neutralizes influenza virus infection.

In certain embodiments, an antibody or antigen binding fragment comprises the light chain CDRs, heavy chain CDRs, or all of the CDRs of antibody 294-16-009-G-1F01 (SEQ ID NOs: 164, 166, 168, 172, 174, and 176), and neutralizes influenza virus infection. In some embodiments, an antibody or antigen binding fragment comprises CDRs with at least 70% sequence identity (e.g., >70%, >75%, >80%, >85%, >90%, >95%, >97%, >98%, >99% or 100%, and ranges therein) and/or at least 50% sequence similarity (e.g., >50%, >60%, >70%, >75%, >80%, >85%, >90%, >95%, >97%, >98%, >99% or 100%, and ranges therein) with the CDRs of antibody 294-16-009-G-1F01 (SEQ ID NOs: 164, 166, 168, 172, 174, and 176), binds the epitope(s) of antibody 294-16-009-G-1F01, and/or neutralizes influenza virus infection.

In certain embodiments, an antibody or antigen binding fragment comprises the light chain CDRs, heavy chain CDRs, or all of the CDRs of antibody 296-16-003-G-2F04 (SEQ ID NOs: 180, 182, 184, 188, 190, and 192), and neutralizes influenza virus infection. In some embodiments, an antibody or antigen binding fragment comprises CDRs with at least 70% sequence identity (e.g., >70%, >75%, >80%, >85%, >90%, >95%, >97%, >98%, >99% or 100%, and ranges therein) and/or at least 50% sequence similarity (e.g., >50%, >60%, >70%, >75%, >80%, >85%, >90%, >95%, >97%, >98%, >99% or 100%, and ranges therein) with the CDRs of antibody 296-16-003-G-2F04 (SEQ ID NOs: 180, 182, 184, 188, 190, and 192), binds the epitope(s) of antibody 296-16-003-G-2F04, and/or neutralizes influenza virus infection.

In certain embodiments, an antibody or antigen binding fragment comprises the light chain CDRs, heavy chain CDRs, or all of the CDRs of antibody 300-16-005-G-2A04 (SEQ ID NOs: 196, 198, 200, 204, 206, and 208), and neutralizes influenza virus infection. In some embodiments, an antibody or antigen binding fragment comprises CDRs with at least 70% sequence identity (e.g., >70%, >75%, >80%, >85%, >90%, >95%, >97%, >98%, >99% or 100%, and ranges therein) and/or at least 50% sequence similarity (e.g., >50%, >60%, >70%, >75%, >80%, >85%, >90%, >95%, >97%, >98%, >99% or 100%, and ranges therein) with the CDRs of antibody 300-16-005-G-2A04 (SEQ ID NOs: 196, 198, 200, 204, 206, and 208), binds the epitope(s) of antibody 300-16-005-G-2A04, and/or neutralizes influenza virus infection.

Figure 11:
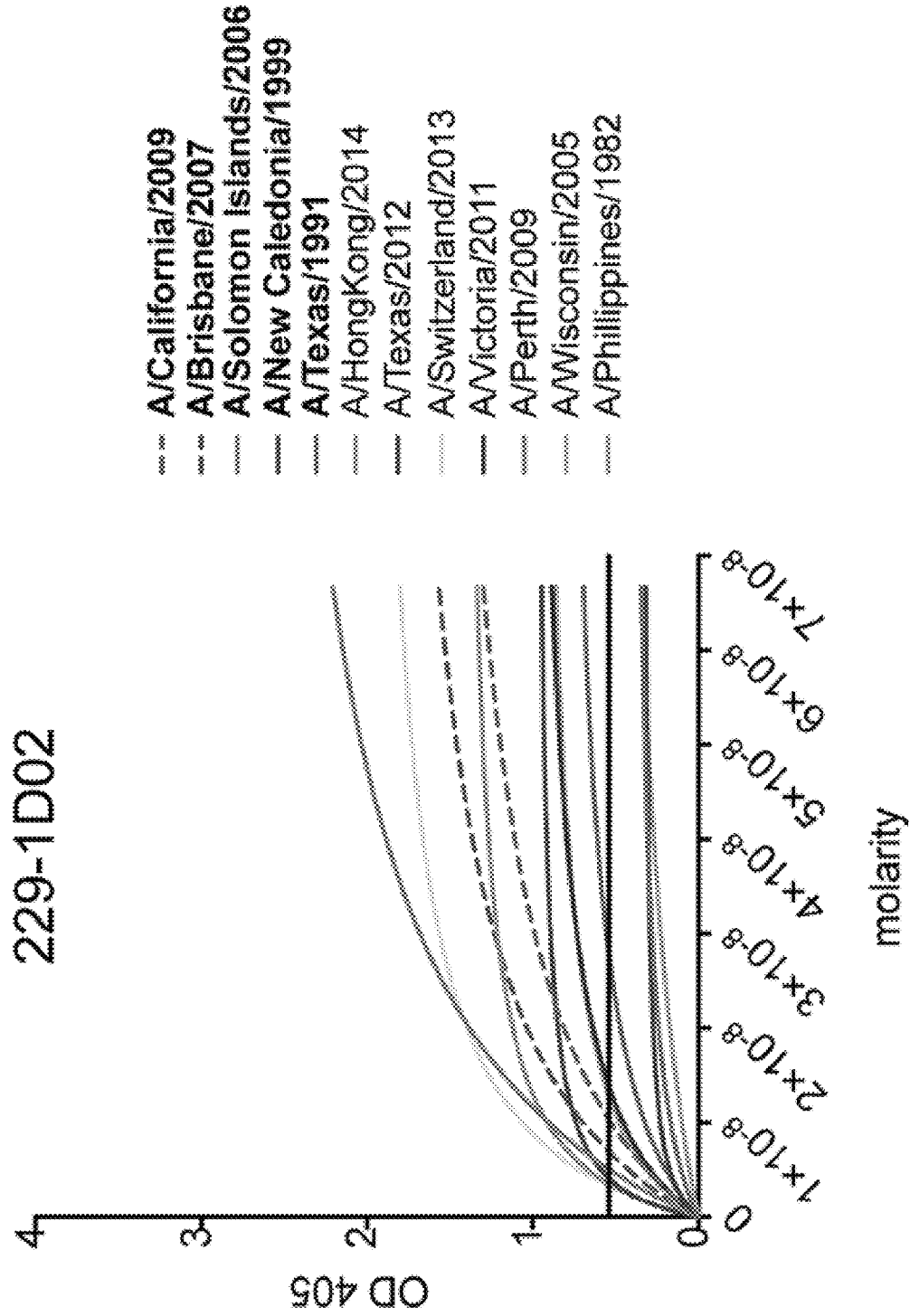
FIG. 11. Binding curves for 229-1D02 against several H1N1 and H3N2 strains.

In certain embodiments, an antibody or antigen binding fragment comprises the light chain CDRs, heavy chain CDRs, or all of the CDRs of antibody 229-1D02 (SEQ ID NOs: 210-212 and 214-216), and neutralizes influenza virus infection. In some embodiments, an antibody or antigen binding fragment comprises CDRs with at least 70% sequence identity (e.g., >70%, >75%, >80%, >85%, >90%, >95%, >97%, >98%, >99% or 100%, and ranges therein) and/or at least 50% sequence similarity (e.g., >50%, >60%, >70%, >75%, >80%, >85%, >90%, >95%, >97%, >98%, >99% or 100%, and ranges therein) with the CDRs of antibody 229-1D02 (SEQ ID NOs: 210-212 and 14-216), binds the epitope(s) of antibody 229-1D02, and/or neutralizes influenza virus infection. 229-1D02 exhibits low affinity binding toward the recent H1N1 strains, A/California/2009 (Kd=2.316×10^-8) and A/Brisbane/2007 (Kd=1.893×10^-8). Such heterosubtypic binding of NA antibodies is rare. Binding curves for 229 1D02 against several H1N1 and H3N2 strains are depicted in FIG. 11.

In certain embodiments, an antibody or antigen binding fragment comprises the light chain CDRs, heavy chain CDRs, or all of the CDRs of antibody 229-1F06 (SEQ ID NOs: 218-220 and 222-224), and neutralizes influenza virus infection. In some embodiments, an antibody or antigen binding fragment comprises CDRs with at least 70% sequence identity (e.g., >70%, >75%, >80%, >85%, >90%, >95%, >97%, >98%, >99% or 100%, and ranges therein) and/or at least 50% sequence similarity (e.g., >50%, >60%, >70%, >75%, >80%, >85%, >90%, >95%, >97%, >98%, >99% or 100%, and ranges therein) with the CDRs of antibody 229-1F06 (SEQ ID NOs: 218-220 and 222-224), binds the epitope(s) of antibody 229-1F06, and/or neutralizes influenza virus infection.

In certain embodiments, an antibody or antigen binding fragment comprises the light chain CDRs, heavy chain CDRs, or all of the CDRs of antibody 229-2D03 (SEQ ID NOs: 226-218 and 230-232), and neutralizes influenza virus infection. In some embodiments, an antibody or antigen binding fragment comprises CDRs with at least 70% sequence identity (e.g., >70%, >75%, >80%, >85%, >90%, >95%, >97%, >98%, >99% or 100%, and ranges therein) and/or at least 50% sequence similarity (e.g., >50%, >60%, >70%, >75%, >80%, >85%, >90%, >95%, >97%, >98%, >99% or 100%, and ranges therein) with the CDRs of antibody 229-2D03 (SEQ ID NOs: 226-218 and 230-232), binds the epitope(s) of antibody 229-2D03, and/or neutralizes influenza virus infection.

In some embodiments, an antibody or antigen binding fragment comprises less than 100% sequence identity with the light chain, heavy chain, or all of any of the antibody sequences of 228-14-035-2D04, 229-14-036-1D05, 229-14-036-1G03, 229-14-036-2B04, 229-14-036-2C06, 235-15-042-1E06, 1000-2E06, 294-16-009-A-1C02, 294-16-009-A-1C06, 294-16-009-A-1D05, 294-16-009-G-1F01, 296-16-003-G-2F04, 300-16-005-G-2A04, 229-1D02, 229-1F06, and/or 229-2D03. In some embodiments, an antibody or antigen binding fragment comprises less than 100% sequence identity with SEQ ID NOs: 2, 10, 18, 26, 34, 42, 50, 58, 66, 74, 82, 90, 98, 106, 114, 122, 130, 138, 146, 154, 162, 170, 178, 186, 194, 209, 213, 217, 221, 225, and/or 229.

The invention further comprises an antibody, or fragment thereof, that binds to the same epitope as an antibody described herein (e.g., 228-14-035-2D04, 229-14-036-

1D05, 229-14-036-1G03, 229-14-036-2B04, 229-14-036-2C06, 235-15-042-1E06, 1000-2E06, 294-16-009-A-1C02, 294-16-009-A-1C06, 294-16-009-A-1D05, 294-16-009-G-1F01, 296-16-003-G-2F04, 300-16-005-G-2A04, 229-1D02, 229-1F06, and/or 229-2D03), or an antibody that competes with an antibody or antigen binding fragment described herein.

Antibodies within the scope described herein may also include hybrid antibody molecules that comprise one or more CDRs from an antibody described herein (e.g., 228-14-035-2D04, 229-14-036-1D05, 229-14-036-1G03, 229-14-036-2B04, 229-14-036-2C06, 235-1000-2E06, 294-16-009-A-1C02, 294-16-009-A-1C06, 294-16-009-A-1D05, 294-16-009-G-1F01, 296-16-003-G-2F04, 300-16-005-G-2A04, 229-1D02, 229-1F06, and/or 229-2D03) and one or more CDRs from another antibody to the same epitope. In one embodiment, such hybrid antibodies comprise three CDRs from an antibody described herein and three CDRs from another antibody to the same epitope. Exemplary hybrid antibodies comprise: (i) the three light chain CDRs from an antibody described herein and the three heavy chain CDRs from another antibody to the same epitope, or (ii) the three heavy chain CDRs from an antibody described herein and the three light chain CDRs from another antibody to the same epitope.

Variant antibodies are also included within the scope herein. Thus, variants of the sequences recited in the application are also included within the scope herein. Such variants include natural variants generated by somatic mutation in vivo during the immune response or in vitro upon culture of immortalized B cell clones. Alternatively, variants may arise due to the degeneracy of the genetic code, or may be produced due to errors in transcription or translation.

Further variants of the antibody sequences having improved affinity and/or potency may be obtained using methods known in the art and are included within the scope herein. For example, amino acid substitutions may be used to obtain antibodies with further improved affinity. Alternatively, codon optimization of the nucleotide sequence may be used to improve the efficiency of translation in expression systems for the production of the antibody. Further, polynucleotides comprising a sequence optimized for antibody specificity or neutralizing activity by the application of a directed evolution method to any of the nucleic acid sequences here are also within the scope included herein.

In some embodiments, variant antibody sequences may share 70% or more (e.g., 75%, 80%, 85%, 90%, 95%, 97%, 98%, 99% or more, or ranges therein) amino acid sequence identity with the sequences recited herein. In some embodiments, variant antibody sequences may share 50% or more (e.g., 55%, 60%, 65%, 75%, 80%, 85%, 90%, 95%, 97%, 98%, 99% or more, or ranges therein) amino acid sequence similarity with the sequences recited herein.

In one embodiment, nucleic acid sequences described herein include nucleic acid sequences having at least 70%, at least 75%, at least 80%, at least 85%, at least 90%, at least 95%, at least 98%, or at least 99% identity to the nucleic acid encoding a heavy or light chain of an antibody described herein (e.g., SEQ ID NOs: 1, 17, 33, 49, 65, 81, 97, 113, 129, 145, 161, 177, 193, 9, 25, 41, 57, 73, 89, 105, 121, 137, 153, 169, 185, and/or 201). In another embodiment, a nucleic acid sequence has the sequence of a nucleic acid encoding a heavy or light chain CDR of an antibody of the invention (e.g., SEQ ID NOs: 3, 19, 35, 51, 67, 83, 99, 115, 131, 147, 163, 179, 195, 5, 21, 37, 53, 69, 85, 101, 117, 133, 149, 165, 181, 197, 7, 23, 39, 55, 71, 87, 103, 119, 135, 151, 167, 183, 199, 11, 27, 43, 59, 75, 91, 107, 123, 139, 155, 171, 187, 203, 13, 29, 45, 61, 77, 93, 109, 125, 141, 157, 173, 189, 205, 15, 31, 47, 63, 79, 95, 111, 127, 143, 159, 175, 191, and/or 207).

In some embodiments, provided herein are modified antibodies and/or modified antibody fragments (e.g., antibodies and antibody fragments comprising non-natural amino acids, substituents, bonds, moieties, connections, etc.). For example, modifications may comprise the introduction of disulfide bonds, glycosylation, lipidation, acetylation, phosphorylation, or any other manipulation or modification, such as conjugation with a labeling or therapeutic agent. Modifications may also include the substitution of natural amino acids for amino acid analogs (including, for example, unnatural amino acids, etc.), as well as other modifications known in the art.

In some embodiments, an antibody finding use in embodiments herein is a non-natural immunogenic agent, such as: an antibody fragment, a non-natural antibody comprising the CDRs herein, a modified antibody, a monoclonal antibody, a humanized antibody, a chimeric antibody, and non-natural combinations thereof.

Further included within the scope of the invention are vectors, for example, expression vectors, comprising a nucleic acid sequence described herein. Cells transformed with such vectors are also included. Examples of such cells include but are not limited to, eukaryotic cells, e.g. yeast cells, animal cells or plant cells. In one embodiment the cells are mammalian, e.g. human, CHO, HEK293T, PER.C6, NS0, myeloma or hybridoma cells.

Embodiments within the scope of this disclosure include methods of preventing or treating influenza infections comprising administering a therapeutically-effective or prophylactically effective amount of a monoclonal antibody having specificity for an NA epitope. In some embodiments, an antibody recognizes (e.g., has affinity and/or specificity for) epitopes having at least 90%, at least 92%, at least 95%, at least 97%, at least 98%, or at least 99% homology to epitope(s) recognized by (e.g., has affinity and/or specificity for) the antibodies described herein.

In some embodiments, a pharmaceutical composition comprising the antibodies disclosed herein includes an acceptable carrier and is formulated into a suitable dosage form according to administration modes. Pharmaceutical preparations suitable for administration modes are known, and generally include surfactants that facilitate transport across the membrane. Such surfactants may be derived from steroids, or may be cationic lipids such as N-[1-(2,3-dioleyloxy)propyl]-N,N,N-trimethylammonium chloride (DOTMA), or various compounds such as cholesterol hemisuccinate and phosphatidyl glycerol.

For oral administration, the pharmaceutical composition may be presented as discrete units, for example, capsules or tablets; powders or granules; solutions, syrups or suspensions (edible foam or whip formulations in aqueous or non-aqueous liquids); or emulsions.

For parenteral administration, the pharmaceutical composition may include aqueous and non-aqueous sterile injection solutions which may contain anti-oxidants, buffers, bacteriostats and solutes which render the formulation substantially isotonic with the blood of the intended recipient; and aqueous and non-aqueous sterile suspensions which may include suspending agents and thickening agents. Excipients available for use in injectable solutions include, for example, water, alcohol, polyols, glycerin, and vegetable oils. Such a composition may be presented in unit-dose (single dose) or multiple dose (several doses) containers, for example, sealed ampoules and vials, and may be stored in a freeze-dried (lyophilized) condition requiring only the addition of the sterile liquid carrier, for example water for injections, immediately prior to use. Extemporaneous injection solutions and suspensions may be prepared from sterile powders, granules and tablets.

The pharmaceutical composition may include antiseptics, solubilizers, stabilizers, wetting agents, emulsifiers, sweeteners, colorants, odorants, salts, buffering agents, coating agents, or anti-oxidants.

Compositions may comprise, in addition to the antibody or antibodies described herein, a therapeutically active agent (e.g., drug), additional antibodies (e.g., against influenza or another target), etc.

The present composition may be formulated into dosage forms for use in humans or veterinary use. The composition comprising the antibodie(s) may be administered to influenza-infected or highly susceptible humans and livestock, such as cows, horses, sheep, swine, goats, camels, and antelopes, in order to prevent or treat the incidence of influenza. When a subject is already infected, the present antibodie(s) may be administered alone or in combination with another antiviral treatment.

The antibody composition may be administered in a pharmaceutically effective amount in a single- or multiple-dose. The pharmaceutical composition may be administered via any of the common routes, as long as it is able to reach the desired tissue. Thus, the present composition may be administered via oral or parenteral (e.g., subcutaneous, intramuscular, intravenous, or intradermal administration) routes, and may be formulated into various dosage forms. In one embodiment, the formulation is an injectable preparation. Intravenous, subcutaneous, intradermal, intramuscular and dropping injectable preparations are possible.

Antibodies may be coupled to a drug for delivery to a treatment site or coupled to a detectable label to facilitate imaging of a site comprising cells of interest, such as cells infected with influenza A virus. Methods for coupling antibodies to drugs and detectable labels are well known in the art, as are methods for imaging using detectable labels. Labeled antibodies may be employed in a wide variety of assays, employing a wide variety of labels. Detection of the formation of an antibody-antigen complex between an antibody of the invention and an epitope of interest (an influenza A virus epitope) can be facilitated by attaching a detectable substance to the antibody. Suitable detection means include the use of labels such as radionuclides, enzymes, coenzymes, fluorescers, chemiluminescers, chromogens, enzyme substrates or co-factors, enzyme inhibitors, prosthetic group complexes, free radicals, particles, dyes, and the like. Examples of suitable enzymes include horseradish peroxidase, alkaline phosphatase, β-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material is luminol; examples of bioluminescent materials include luciferase, luciferin, and aequorin; and examples of suitable radioactive material include $^{125}I$, $^{131}I$, $^{35}S$, or $^{3}H$. Such labeled reagents may be used in a variety of well-known assays, such as radioimmunoassays, enzyme immunoassays, e.g., ELISA, fluorescent immunoassays, and the like.

An antibody may be conjugated to a therapeutic moiety. Such antibody conjugates can be used for modifying a given biological response; the drug moiety is not to be construed as limited to classical chemical therapeutic agents. For example, the drug moiety may be a protein or polypeptide possessing a desired biological activity. Techniques for conjugating such therapeutic moiety to antibodies are well known. See, for example, Arnon et al. (1985) "Monoclonal Antibodies for Immunotargeting of Drugs in Cancer Therapy," in Monoclonal Antibodies and Cancer Therapy, ed. Reisfeld et al. (Alan R. Liss, Inc.), pp. 243-256; ed. Hellstrom et al. (1987) "Antibodies for Drug Delivery," in Controlled Drug Delivery, ed. Robinson et al. (2d ed; Marcel Dekker, Inc.), pp. 623-653; Thorpe (1985) "Antibody Carriers of Cytotoxic Agents in Cancer Therapy: A Review," in Monoclonal Antibodies '84: Biological and Clinical Applications, ed. Pinchera et al. pp. 475-506 (Editrice Kurds, Milano, Italy, 1985); "Analysis, Results, and Future Prospective of the Therapeutic Use of Radiolabeled Antibody in Cancer Therapy," in Monoclonal Antibodies for Cancer Detection and Therapy, ed. Baldwin et al. (Academic Press, New York, 1985), pp. 303-316; and Thorpe et al. (1982) Immunol. Rev. 62:119-158; herein incorporated by reference in their entireties.

Alternatively, an antibody, or antibody fragment thereof, can be conjugated to a second antibody, or antibody fragment thereof, to form an antibody heteroconjugate as described in U.S. Pat. No. 4,676,980; herein incorporated by reference in its entirety. In addition, linkers may be used between the labels and the antibodies of the invention (e.g. U.S. Pat. No. 4,831,175; herein incorporated by reference in its entirety).

Antibodies of the invention may also be attached to a solid support. Additionally, antibodies of the invention, or functional antibody fragments thereof, can be chemically modified by covalent conjugation to a polymer to, for example, increase their circulating half-life. In some embodiments the polymers may be selected from polyoxyethylated polyols and polyethylene glycol (PEG). PEG is soluble in water at room temperature and has the general formula: R(O—CH$_2$—CH$_2$)$_n$O—R where R can be hydrogen, or a protective group such as an alkyl or alkanol group.

Water-soluble polyoxyethylated polyols may also be employed. They include polyoxyethylated sorbitol, polyoxyethylated glucose, polyoxyethylated glycerol (POG), and the like. Another drug delivery system that can be used for increasing circulatory half-life is the liposome.

Antibodies may be provided in purified form. Typically, the antibody will be present in a composition that is substantially free of other polypeptides e.g. where less than 90% (by weight), usually less than 60% and more usually less than 50% of the composition is made up of other polypeptides.

Antibodies of the invention can be of any isotype (e.g. IgA, IgG, IgM (e.g., an alpha, gamma or mu heavy chain). Within the IgG isotype, antibodies may be IgG1, IgG2, IgG3 or IgG4 subclass. Antibodies may have a kappa or a lamda light chain.

EXPERIMENTAL

Example 1

Materials and Methods

Cell, Viruses and Recombinant Proteins

Human embryo kidney (HEK) 293T and Madin-Darby canine kidney (MDCK) cells were obtained from the American Type Culture Collection (ATCC). All influenza virus stocks used for the assays were freshly grown in specific pathogen free (SPF) eggs, harvested, purified and titered. A reassortant H6N2 virus with the backbone from A/Puerto Rico/8/34 (PR8) containing the HA gene of A/turkey/Massachusetts/3740/76 and the NA from A/Minnesota/11/2010 was used to generate the mutant viruses (S153T, N199K, N221K, G248E, S322F, K344E, G346D, E369T, K400R, G429E, K435E and W437R single mutation in the NA gene). A/Switzerland/9715293/2013 (H3N2) was treated with 0.02% formaldehyde for 48 h to generate the inactive virus particles. The inactivation was verified by injecting treated virus into eggs followed by HA measurements. Recombinant NA proteins derived from A/Puerto Rico/8/1934 (H1N1), A/New Caledonia/20/1999 (H1N1), A/Brisbane/59/2007 (H1N1), A/California/7/2009 (H1N1), A/grey teal/Australia/2/1979 (H4N4), A/Shanghai/1/2013 (H7N9), A/equine/Pennsylvania/1/2007 (H3N8), A/turkey/Wisconsin/1/1966 (H9N2) were obtained from BEI resources and A/Canada/444/2004 (H7N3) N3 NA was obtained from the Influenza Reagent Resource (IRR). The other recombinant NA and HA proteins were expressed in-house, in a baculovirus expression system (Margine et al., 2013b; herein incorporated by reference in its entirety).

Monoclonal Antibodies

Antibodies were generated as described in Smith et al., 2009; Wrammert et al., 2008; herein incorporated by reference in their entireties. Peripheral blood was obtained from each subject 7 days after infection or vaccination. Lymphocytes were isolated and enriched for B cells using RosetteSep. Plasmablasts (CD3− CD19+ CD20low CD27hi CD38hi) were single cell-sorted into 96-well plates Immunoglobulin variable genes from plasmablasts were amplified by reverse transcriptase polymerase chain reaction (RT-PCR) and sequenced, then cloned into human IgG1 expression vectors and co-transfected into HEK293 cells. Secreted mAbs were purified from the supernatant using protein A beads.

Enzyme Linked Immunosorbent Assay (ELISA)

High-protein binding microtiter plates (Costar) were coated with 8 hemagglutinating units (HAU) of whole virus per well or recombinant NAs or HAs at 1 µg/ml in phosphate buffered saline (PBS) overnight at 4° C. After blocking, serially diluted antibodies 1:3 starting at were incubated for 1 h at 37° C. Horse radish peroxidase (HRP)-conjugated goat anti-human IgG antibody diluted 1:1000 (Jackson Immuno Research) was used to detect binding of mAbs, and was developed with Super Aquablue ELISA substrate (eBiosciences). Absorbance was measured at 405 nm on a microplate spectrophotometer (BioRad). To standardize the assays, antibodies with known binding characteristics were included on each plate and the plates were developed when the absorbance of the control reached 3.0 OD units. Competition ELISAs were performed by inhibiting binding of each biotinylated antibody of interest at the half-maximal binding concentration with a 10-fold molar excess of competitor antibody. HRP conjugated streptavidin diluted 1:1000 (Southern Biotech) was used for detection. Plates were developed until samples in the absence of competitor antibody reached an OD of 1 (Henry Dunand et al., 2015; herein incorporated by reference in its entirety).

Cell-Based ELISA

A/California/7/2009 NA and its mutants were expressed on 293T cells by transfecting with wild type or mutant pCAGGS-CA/09NA plasmids using Lipofectamine 2000 reagent (Invitrogen). ELISA was performed with the transfected cells as described previously (Wan et al., 2013). For all other NAs (mutant and wild type), the signals generated by mAb binding to each NA were normalized to those generated by mouse serum (the background signals generated with mock-transfected cells were subtracted from both the mAb and mouse serum signals) and therefore expressed as relative binding.

Microneutralization Assay (MN)

MN assay for antibody characterization was carried out (Henry Dunand et al., 2015; herein incorporated by reference in its entirety). MDCK cells were maintained in Dulbecco's modified Eagle's medium (DMEM) supplemented with 10% fetal bovine serum (FBS) at 37° C. with 5% $CO_2$. On the day before the experiment, confluent MDCK cells in a 96-well format were washed twice with PBS and incubated in minimal essential medium (MEM) supplemented with 1 µg/ml trypsin-ethylenediamine tetraacetic acid (EDTA). Serial 2-fold dilutions (starting concentration 128 µg/ml) of mAb were mixed with an equal volume of 100 50% tissue culture infectious doses ($TCID_{50}$) virus and incubated for 1 h at 37° C. The mixture was removed and cells were cultured for 20 h at 37° C. with 1×MEM supplemented with 1 µg/ml trypsin-TPCK and appropriate mAb concentration. Cells were washed twice with PBS, fixed with 80% ice cold acetone at −20° C. for 1 h, washed 3 times with PBS, blocked for 30 min with 10% FBS and then treated for 30 min with 2% $H_2O_2$. An anti-NP-biotinylated antibody (1:3000) in 3% BSA-PBS was incubated for 1 h at room temperature. The plates were developed with Super Aquablue ELISA substrate at 405 nm. The signal from uninfected wells were averaged to represent 100% inhibition. Virus infected wells without mAb were averaged to represent 0% inhibition. Duplication wells were used to calculate the mean and SD of neutralization, and inhibitory concentration 50 ($IC_{50}$) was determined by a sigmoidal dose response curve. The inhibition ratio (%) was calculated as below:

$$(OD\ (Pos.\ Control) - OD\ (Sample))/(OD\ (Pos.\ Control) - OD\ (Neg.\ Control)) \times 100\%$$

The final concentration of antibody that reduced infection to 50% ($IC_{50}$) was determined using Prism software (GraphPad).

NA Enzyme-Linked Lectin Assay (ELLA)

ELLAs were performed as described (Westgeest et al., 2015; herein incorporated by reference in its entirety). Flat-bottom nonsterile 96-well plates (Thermo Scientific) were coated with 100 µl of fetuin (Sigma) at 25 µg/ml at 4° C. overnight. 50 µl antibodies were serially diluted (two-fold) in Dulbecco's phosphate-buffered saline (DPBS) containing 0.133 g/L $CaCl_2$ and 0.1 g/L $MgCl_2$ with 0.05% Tween 20 and 1% BSA (DPBST BSA), then incubated in duplicate fetuin-coated plates with an equal volume of the selected antigen dilution in DPBSTBSA. These plates were subsequently sealed and incubated for 18 h at 37° C. The plates were subsequently washed six times with PBS with 0.05% Tween 20, and 100 µl/well of HRP-conjugated peanut agglutinin lectin (PNA-HRPO, Sigma-Aldrich) in $DPBST_{BSA}$ was added for 2 h at RT in the dark. The plates were washed six times and were developed with Super Aquablue ELISA substrate (eBiosciences). Absorbance was read at 405 nm on a microplate spectrophotometer (BioRad). Data points were analyzed using Prism software and the 50% inhibition concentration ($IC_{50}$) was defined as concentration at which 50% of the NA activity was inhibited compared to the negative control.

NA-STAR Assay

The NA-STAR assay was performed according to the Resistance Detection Kit manufacturer's instructions (Applied Biosystems, Darmstadt, Germany) (Nguyen et al., 2010; herein incorporated by reference in its entirety). 25 µl test mAbs in serial two-fold dilutions in NA-Star assay buffer (26 mM 2-(N-morpholino) ethanesulfonic acid; 4 mM calcium chloride; pH 6.0) were mixed with 25 µl of NA protein or 4×IC$_{50}$ of virus and incubated at 37° C. for 20 min After adding 10 µl of 1000× diluted NA-Star substrate, the plates were incubated at room temperature for 30 min. The reaction was stopped by adding 60 µl of NA Star accelerator. The chemiluminescent was determined by using the DTX 880 plate reader (Beckman Coulter). Data points were analyzed using Prism software and the 50% inhibition concentration (IC$_{50}$) was defined as concentration at which 50% of the NA activity was inhibited compared to the negative control.

Competition Studies Using Bio-Layer Interferometry

A forteBio Octet K2 instrument was used to measure the competition between the N2-reactive mAbs and oseltamivir. A/Texas/50/2012 rNA (5 µg/ml) in PBS was used to load anti-His probes for 300 s, then the probes were moved to oseltamivir (25 µg/ml) and control PBS for another 300 s, and following by binding of the complex to the N2-reactive mAbs (50 µg/ml) for 300 s to 500 s. The final volume for all the solutions was 200 µl/well. All of the assays were performed with agitation set to 1,000 r.p.m. in PBS buffer supplemented with 1% BSA to minimize nonspecific interactions at 30° C.

Mouse Challenge and Immunization Experiments

In prophylactic studies, five female BALB/c mice (The Jackson Laboratory) per group aged 6 to 8 weeks received a 5 mg/kg dose of mAbs intraperitoneally (i.p.). After 2 h treatment, the mice were anesthetized using a ketamine-xylazine mixture and intranasally infected with 10× the 50% lethal dose (LD$_{50}$) of A/Netherlands/602/2009 (H1N1), A/Philippines/2/1982 (H3N2, X-79-surface glycoproteins from A/Philippines/2/1982 and backbone from A/PR/8/34) or A/Vietnam/1203/2004 (H5N1-surface glycoproteins from A/Vietnam/1203/2004 and backbone from A/PR/8/34, polybasic cleavage site replaced with a regular cleavage site). In a therapeutic setting, mice received a 10 mg/kg dose of each mAbs i.p. 48 h after 10 LD$_{50}$ virus intranasal inoculation (in a 30 µl inoculum). In all groups, mice were monitored daily for survival and weight loss until day 14 post-infection. Mice that lost 25% or more of their initial body weights were euthanized. For the immunization assays, mice were infected by 0.25 LD$_{50}$ of A/Netherlands/602/2009 (H1N1) or immunized with 2 µg of inactivated A/Switzerland/9715293/2013 (H3N2) influenza virus intranasally and boosted on day 30 using the same immunogens/doses. Spleen cells were collected on day 38 and analyzed for the HA and NA humoral immune response by ELISPOT.

Purification of NA-Reactive IgG from Serum

Each serum sample analyzed was passed through a 5 ml Protein G Plus agarose (Pierce) affinity column in gravity mode. Serum flow-through was collected and passed through the column three times. The column was then washed with 15 column volume (CV) of PBS prior to elution with 5 CV of 100 mM glycine-HCl, pH 2.7. The eluate, containing total IgG from serum, was immediately neutralized with 5 ml of 1 M Tris-HCl, pH 8.0. The flow-through was subjected to the same purification process one more time to capture all IgG from serum, and the two eluates were combined. To isolate the NA-reactive IgG, recombinant N2 neuraminidase (rNA) from A/Hong Kong/4801/2014 was first biotinylated using the EZ-link Sulfo-NHS-Biotin (Thermo Scientific) according to the methods provided by the manufacturers. Biotinylated rNA was then bound to NeutrAvidin agarose resins (Pierce) packed into a 0.5 ml chromatography column (Clontech). The resins were equilibrated with 10 CV of PBS. Total IgG was applied to a column packed with Neutravidin agarose resins only, and flow-through was collected in order to remove any resin-binding IgGs. The collected samples were then subjected to the affinity column with rNA in gravity mode, and flow-through was collected and reapplied to the column three times. The column was washed with 10 CV of PBS and eluted with 5 CV of 100 mM glycine-HCl, pH 2.7 and immediately neutralized with 1 M Tris-HCl, pH 8.0. The flow-through from each pull-down was subjected to the same purification process until all of NA-reactive IgGs were isolated. All eluate samples from each donor were combined, then buffer-exchanged into PBS and concentrated using a 30 kDa Vivaspin 15 centrifuge tube (Sartorius).

Statistical Analysis

Statistical analysis was performed using Prism software (Graphpad). Specific tests for statistical significance are detailed in the figure legends. P values equal to or less than 0.05 were considered significant.

Example 2

Results

NA is Frequently Targeted by Plasmablasts Activated During Natural Influenza Virus Infection but not after Vaccination While characterizing the specificity of plasmablasts induced by influenza virus infection, a high proportion of NA-reactive cells was observed. The specificity of plasmablasts was evaluated by ELISPOT or mAb characterization from a total of sixteen confirmed influenza-infected patients.

Figure 8:
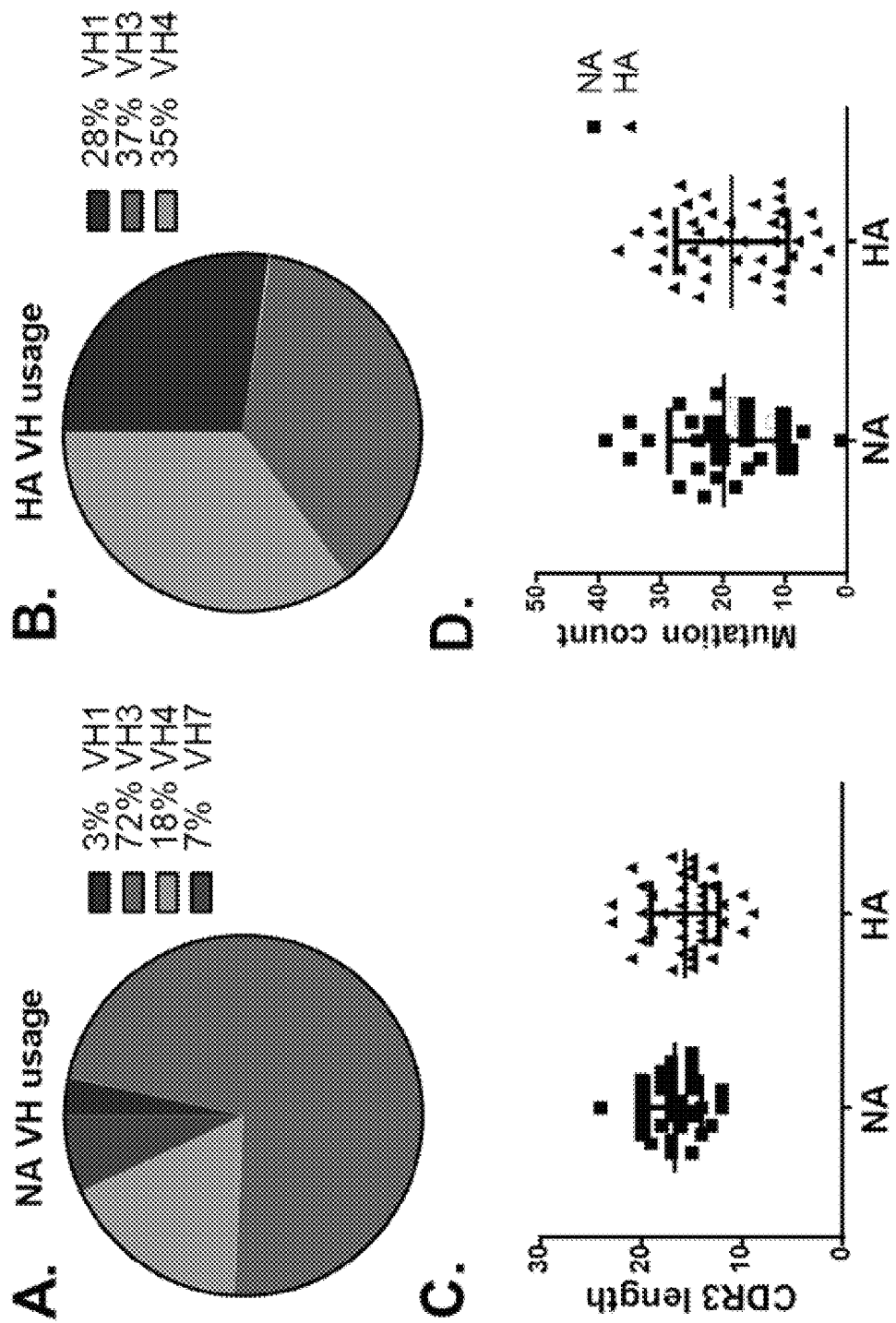
FIG. 8. Influenza virus infection induced NA-reactive plasmablasts that were VH3-biased. (Panels A-B) The usage of VH immunoglobulin genes by (Panel A) NA-reactive B cells and (Panel B) HA-reactive B cells (Panel C) CDR3 length of NA and HA-reactive mAbs, data are represented as mean±SD. (Panel D) Total mutation number of NA and HA-reactive mAbs, data are represented as mean±SD.
Figure 9E:
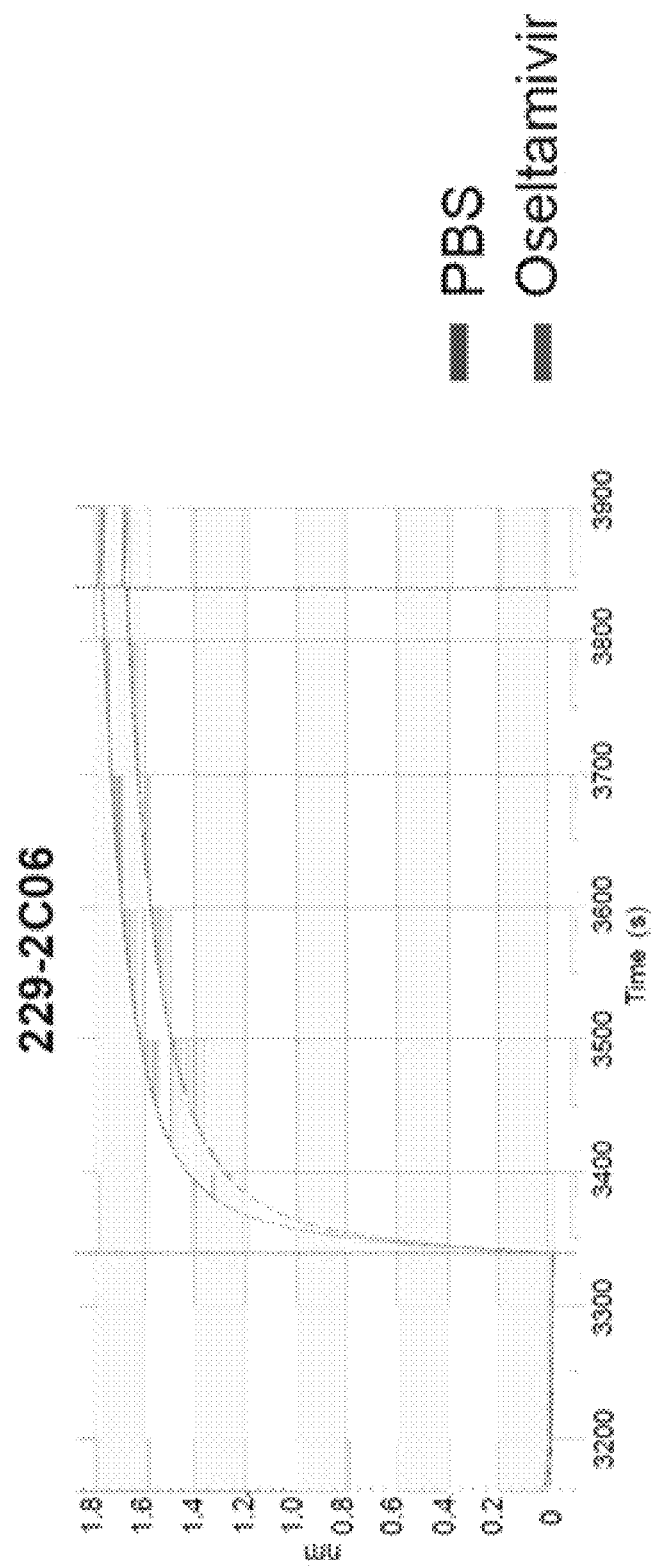
Figure 10:
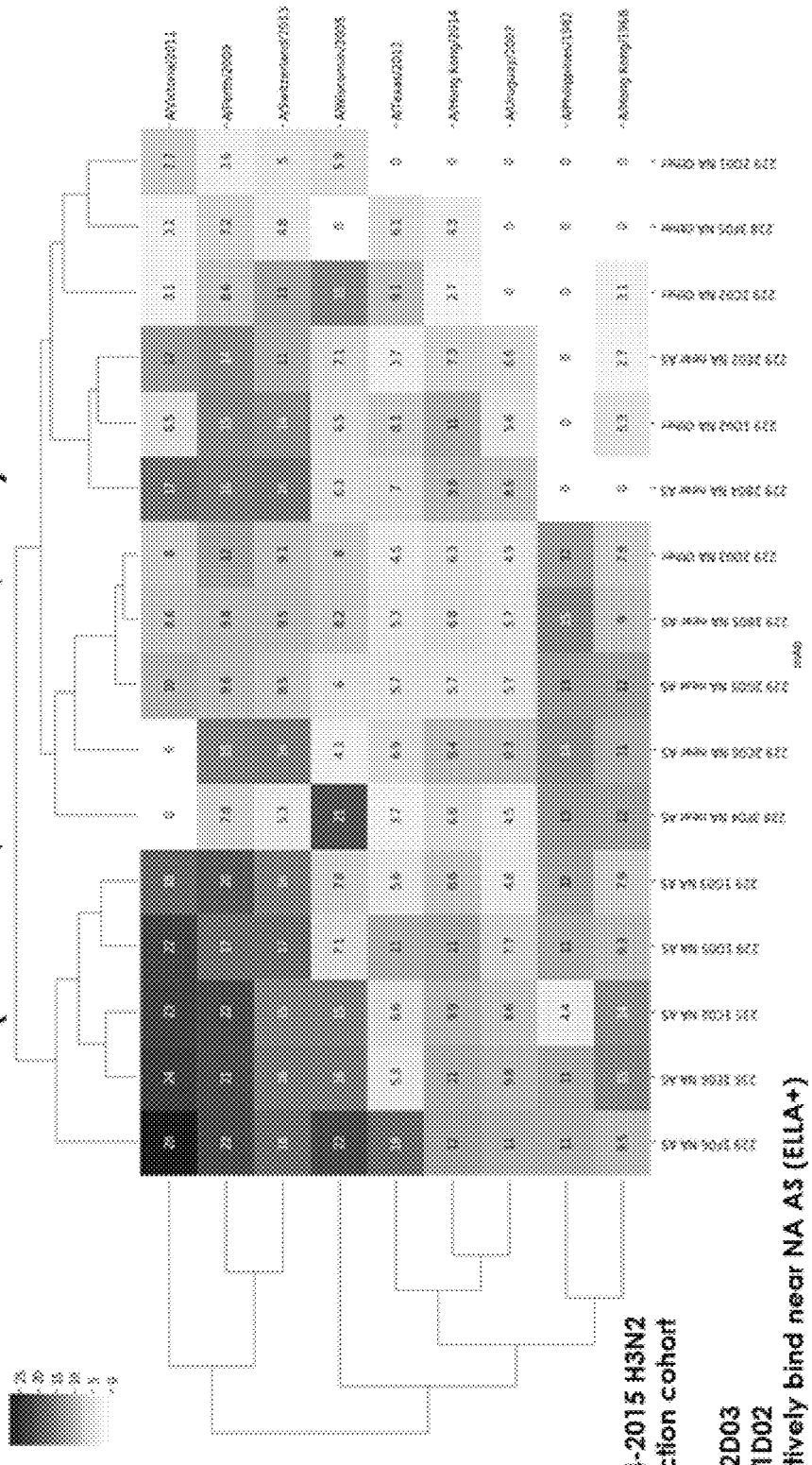
FIG. 10. Heat map of 2014-2015 H3N2-induced NA mAb binding to H3N2 strains; x-axis are individual mAbs, y-axis are H3N2 virus strains. The heat map depicts the mAb clustering based on similarity in viral binding patterns using Euclidean distance. The viruses cluster based on their binding to the mAbs, they are not clustered based on actual phylogenetic distance. Each individual box represents the ELISA area under the curve value for viral binding, with darker colors being stronger binding.

These patients included eleven patients infected with the H1N1 pandemic strain (five from 2009 and six from 2016), plus five patients were infected with H3N2 virus strains, including three in 2014 and two in 2017 (clinical data is provided in Table 1). First, large numbers of activated plasmablasts were analyzed in six influenza virus infected patients (four infected with H1N1 in 2016 and two infected with H3N2 in 2017). Scoring of thousands of activated plasmablasts by ELISPOT assay detected an average of 24% that were reactive to NA and 38% to HA (FIG. 1A). Plasmablasts from H3N2 infected patients predominantly targeted NA. To more rigorously assess the frequency of NA-reactive B cells activated during infection, mAbs obtained from patients were characterized. The isolated variable region genes from single plasmablasts activated by infection were used to express mAb proteins from 12 of the patients (See, e.g., Smith et al., 2009; Wardemann et al., 2003; Wrammert et al., 2008; herein incorporated by reference in their entireties). The NA-reactive mAbs were more often encoded by VH3 family genes, but used variable genes that were otherwise similar to HA antibodies (FIG. 8). Consistent with the ELISPOT assays, 22.6% (29/128), and on average 24% by year and strain, of plasmablast mAbs activated by influenza virus infection were reactive to recombinant NA (rNA) (FIGS. 1B, 1C, and 1D). As with the ELISPOT analysis, H3N2 virus infections consistently induced a higher proportion of NA-reactive B cells compared to HA-reactive B cells for all five patients assessed (FIGS. 1A and 1D, blue dots). By comparison, activation of NA-reactive B cells was quite rare after vaccination, accounting for only 1.2% (3/258) of induced plasmablasts relative to 87% that targeted HA (FIG. 1E). This observation was consistent for several influenza virus vaccine compositions, including 1.5% (2 of 133) of NA-reactive cells after immunization with a subunit vaccine (from 2006-2008 and in 2010), 1.1% (1 of 89) after the 2009 H1N1 monovalent vaccine, and none (0 of 36) induced by split vaccines (2008-2010) (FIG. 1E). The analysis demonstrates that a quarter of plasmablasts induced by natural influenza virus infection target NA—a percentage that nearly equals that of HA-specific plasmablasts—compared to only 1-2% from influenza vaccination.

TABLE 1

Summary of clinical data for patients with acute influenza virus infections

| YEAR | ID | Age | Gen | Influenza A Strain | Vaccine History | Comorbidities | Initial Symptoms* | Hospital course | Sample collection | Anti-viral treatment |
|---|---|---|---|---|---|---|---|---|---|---|
| 2009 | EM | 30 | F | Pan H1N1 | N/A | NONE | Dyspnea | Acute respiratory distress syndrome, bacterial pneumonia, pulmonary embolism, prolonged oscillatory ventilator support, tracheostomy, discharged after 2 months | D31 | Oseltamivir |
| 2009 | 1000 | 37 | M | Pan H1N1 | N/A | Hypertension, interstitial lung disease of unknown etiology | Shortness of breath, nausea, vomiting | Pneumonia, acute sinusitis, acute renal failure, discharged after 8 days | D18 | Oseltamivir Zanamavir |
| 2009 | 70 | 38 | F | Pan H1N1 | N/A | NONE | Body aches | N/A | D15 | NONE |
| 2009 | 1009 | 21 | M | Pan H1N1 | N/A | Congenital heart repair for disease, tetralogy of Fallot | Sore throat, nausea, diarrhea | N/A | D9 | Oseltamivir |
| 2009 | 1011 | 25 | M | Pan H1N1 | N/A | NONE | Sore throat, vomiting, headache, confusion | N/A | D9 | Oseltamivir |
| 2016 | 294-16-009 | 23 | M | Pan H1N1 | 2015 | NONE | Sore throat | N/A | D7 | NONE |
| 2016 | 296-16-003 | 26 | M | Pan H1N1 | No History | NONE | Myalgias | Dehydration, fainting, ER | D7 | NONE |
| 2016 | R005-14-0101 | 24 | F | Pan H1N1 | N/A | NONE | Fatigue, runny nose, headache, nausea, vomiting | Outpatient | D7 | NONE |
| 2016 | R018-14-0101 | 43 | F | Pan H1N1 | N/A | NONE | Sore throat, runny nose, tiredness, headache, body aches, nausea | N/A | D7 | NONE |
| 2016 | 300-16-005 | 30 | M | Pan H1N1 | No History | NONE | Sore throat fatigue, chills | ER | D11 | Oseltamivir |
| 2016 | 301-16-007 | 46 | F | Pan H1N1 | 2014 | Hypertension, asthma | Body ache, nausea | ER and then Hospitalized for dehydration and difficulty breathing | D8 | Oseltamivir |
| 2014 | 228-14-035 | 34 | M | S H3N2 | 2011-2013 | ASTHMA | Sore throat | Asthma exacerbation, ER | D7 | Oseltamivir |
| 2014 | 229-14-036 | 46 | F | S H3N2 | 2011-13 | COPD ASTHMA | Runny nose | Acute COPD exacerbation, ER | D7 | Oseltamivir |
| 2014 | 235-15-042 | 49 | M | S H3N2 | 2009-14 | OA, ASTHMA, CHF | Runny nose | Asthma exacerbation ER | D7 | Oseltamivir |
| 2017 | 319-17-008 | 38 | M | S H3N2 | 2013-14 | NONE | Sore throat | N/A | D15, D63 | NONE |
| 2017 | 323-17-012 | 31 | M | S H3N2 | N/A | NONE | Body ache, runny nose | N/A | D7, D21 | NONE |

*Initial Symptoms: Fever and cough experienced by all patients; S: seasonal; Pan: pandemic; ER: presented to emergency room; COPD: Chronic obstructive pulmonary disease; OA: Osteoarthritis; CHF: Congestive heart failure.

Figure 2A:
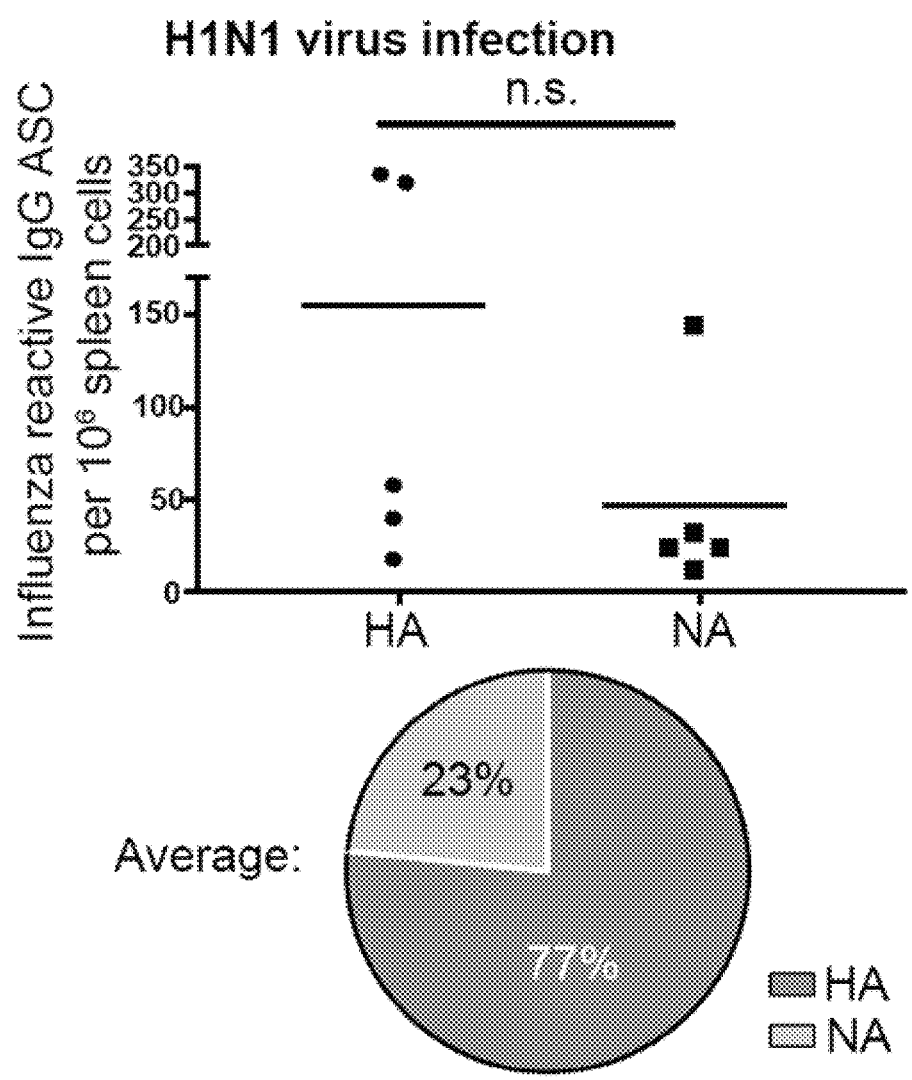
FIGS. 2A-F. Epitopes on NA are not efficiently presented in current commercially available inactivated influenza virus vaccines (A-B) The proportion of HA and NA-reactive IgG secreting cells (ASCs) in immunized mice was determined by ELISPOT. Mouse splenocytes were isolated 8 days after boost (A) with A/Netherlands/602/2009 (H1N1) virus by intranasal inoculation, or (B) after inactivated A/Switzerland/9715293/2013 (H3N2) virus particle intranasal immunization. Each dot represents one mouse. Pie charts show the average frequency of HA versus NA-reactive B cells. (C-F) HA and NA-reactive mAbs were tested for binding by ELISA to HA, NA and two influenza virus vaccine preparations. Binding avidities (KD) were estimated by Scatchard plot analyses of ELISA data. (C) Binding of 35 H1-reactive mAbs to A/California/7/2009 (H1N1) rHA was compared to binding to influenza virus vaccine Fluarix (2015-2016). Binding of 10 H3-reactive mAbs against A/Texas/50/2012 (H3N2) rHA was compared to binding to vaccine Fluarix (2014-2015), respectively. (E) Binding of 35 H1-reactive mAbs to A/California/7/2009 (H1N1) rHA was compared to binding to the influenza vaccine Fluzone (2016-2017). (D) Binding of 15 N1-reactive mAbs to A/California/7/2009 (H1N1) rNA was compared to binding to influenza virus vaccine Fluarix (2015-2016). Binding of 14 N2-reactive mAbs against A/Texas/50/2012 (H3N2) rNA was compared to binding to vaccine Fluarix (2014-2015), respectively. (F) Binding of 15 N1-reactive mAbs to A/California/7/2009 (H1N1) rNA was compared to binding to the influenza vaccine Fluzone (2016-2017). Data are representative of three independent experiments. Statistical significance was determined using the paired nonparametric Wilcoxon test. The line represents the median. n.s., not significant. *$p<0.05$; $p<0.001$; *$p<0.0001$.
Figure 2B:
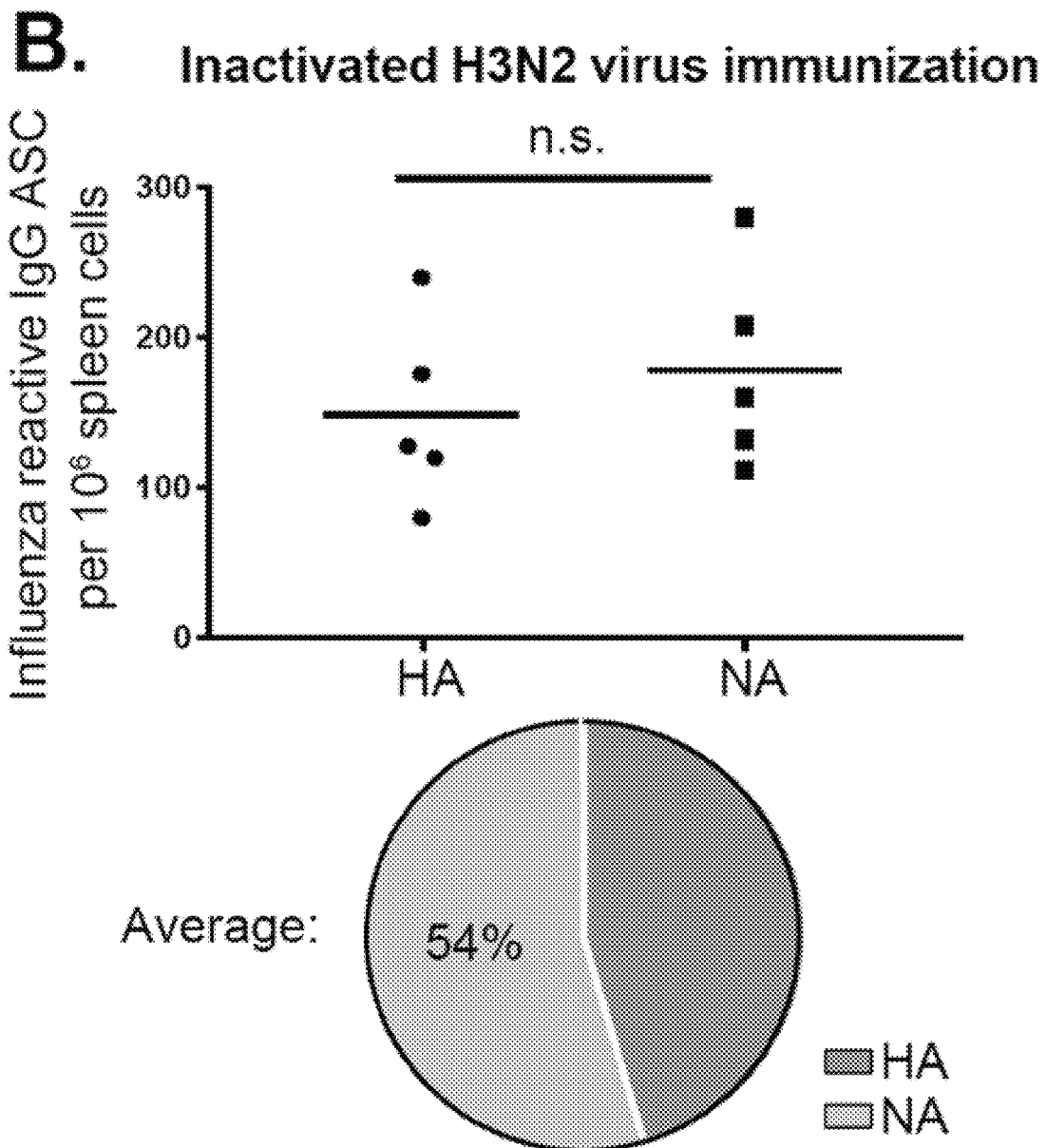
Figure 2C:
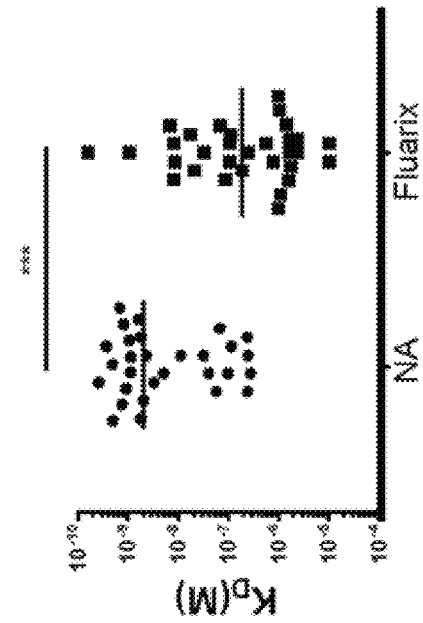
Figure 2D:
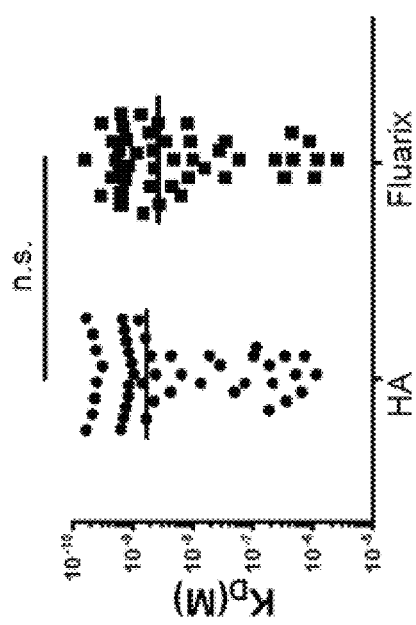
Figure 2E:
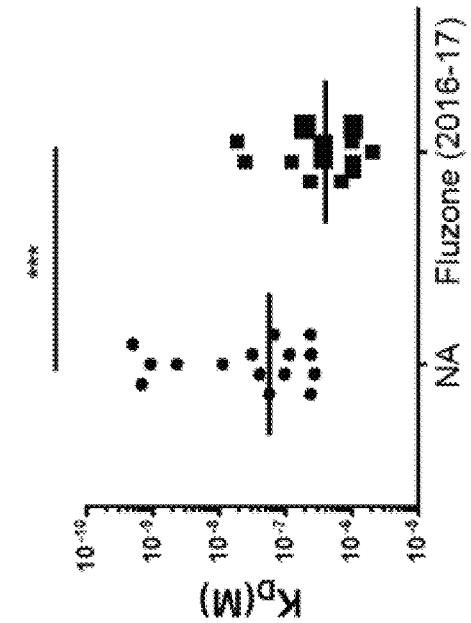
Figure 2F:
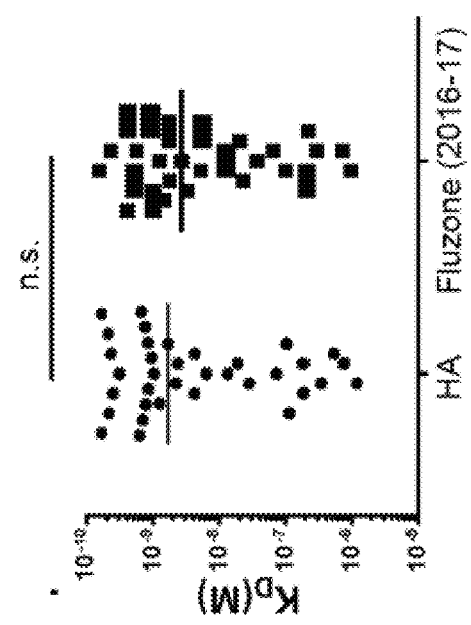

Infection-Induced Anti-NA Antibodies Bind Epitopes that are not Preserved in Current Influenza Vaccines Experiments were conducted during development of embodiments herein to determine whether the greater induction of NA-reactive plasmablasts during natural infection compared to vaccination is because the live, replicating virus displays epitopes not present in the inactivated vaccines. Memory to conserved epitopes appears to play a role in the observed bias, as serological studies have shown an induction of NA-reactive antibodies to past strains (Rajendran et al., 2017; herein incorporated by reference in its entirety). Both HA and NA antibodies were encoded from highly mutated variable genes, supporting a memory cell recall origin (FIG. 8). Furthermore, primary exposure to the 2009 pandemic influenza virus strain induced NA-reactive plasmablasts at detectable frequencies in only two of the five infected patients that we characterized (top row of FIG. 1D). Conversely, exposure to that strain seven years later in 2016 or to H3N2 strains that have circulated since 1968 readily induced NA-reactive plasmablasts (FIGS. 1A and 1D). To determine if infection or exposure to whole virus particles could account for the increased NA targeting, mice were infected with intact virions as opposed to split/subunit vaccine. For this, mice were infected intranasally with a sublethal dose of live 2009 pandemic H1N1 virus (A/Netherlands/602/2009) or immunized intranasally with intact virions of inactivated H3N2 (A/Switzerland/9715293/2013) influenza virus, followed by an intranasal boost with the respective virus strains 30 days later. ELISPOT assays on whole splenocytes eight days after secondary infection or immunization was used to measure the proportions of HA- and NA-reactive IgG-secreting cells that were activated. Similar to what was observed in infected humans, the frequency of NA-reactive cells was common after exposure to whole virions for both the H1N1 and H3N2 strains (FIGS. 2A and 2B). This observation was not dependent on viral replication as the H3N2 influenza strain was inactivated. Notably, as in human infections with an H3N2 virus, more plasmablasts were specific to N2 than to H3 (FIG. 2B). Together these experiments suggest that NA epitopes present on whole virions are not efficiently targeted by current influenza vaccines. To address this possibility directly, the NA- and HA-reactive mAbs generated from infection-induced plasmablasts were tested for binding to inactivated influenza virus vaccines. This analysis was done on vaccines not expired and with matching influenza virus strains to those causing infection. While HA-reactive mAbs bound rHA protein with equal affinity to the vaccine, the NA-reactive mAbs had only negligible binding to the FLUARIX (FIGS. 2C and 2D) or FLUZONE (FIGS. 2E and 2F) vaccines. The FLUBLOK recombinant protein vaccine has no NA component at all and so also would not induce NA-reactive antibodies. Experiments conducted during development of embodiments herein demonstrate that current influenza virus vaccines have insufficient NA content or NA protein structural integrity to induce NA-reactive antibody responses efficiently.

Human NA-Reactive mAbs are More Broadly Reactive than HA-Reactive mAbs

Figure 3:
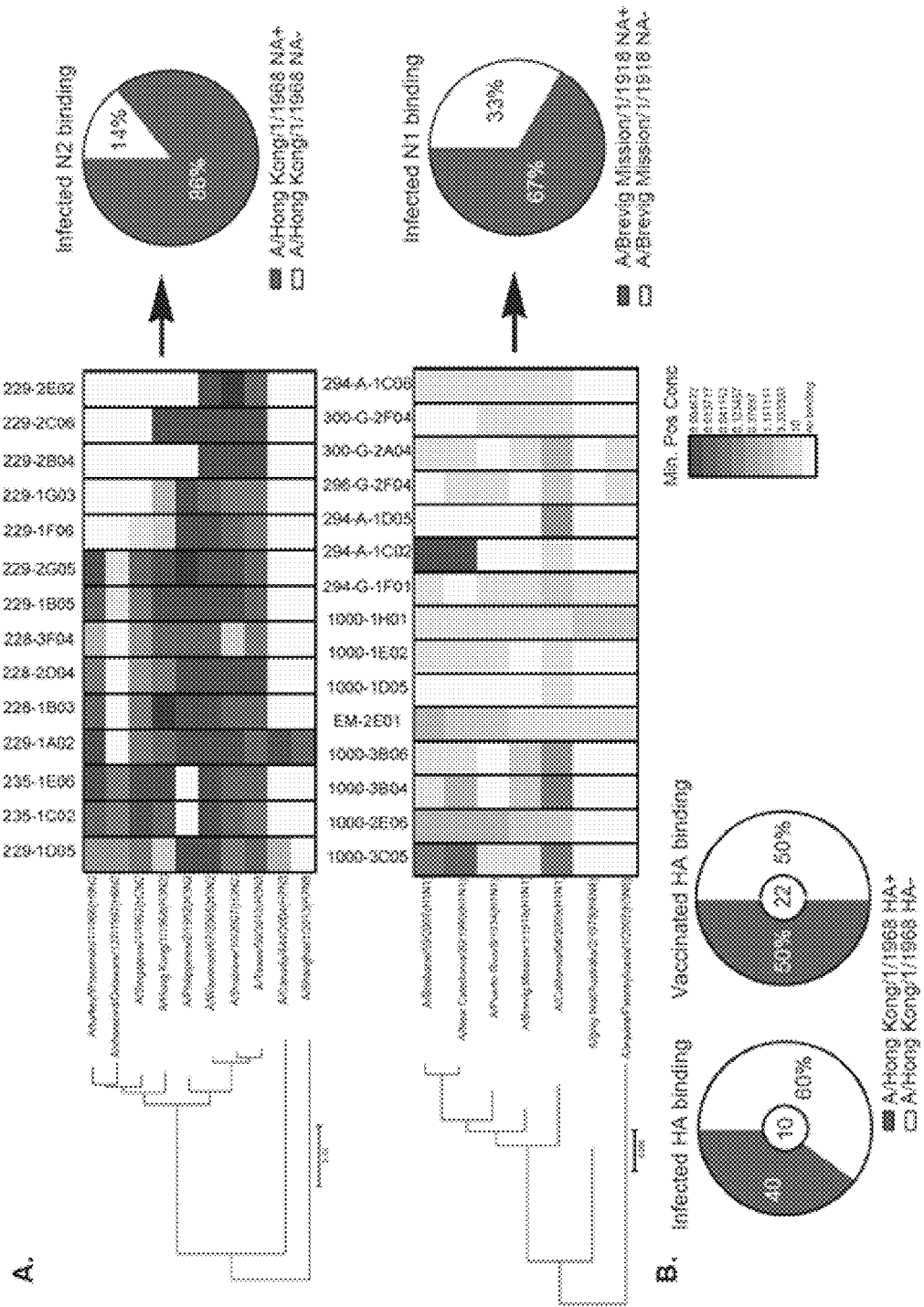
FIG. 3. NA-reactive mAbs are broadly cross-reactive. (Panel A) Binding of NA-reactive mAbs to rNA proteins was measured by ELISA. (Panel A) Representative minimum positive concentrations (µg/ml) from three independent experiments are plotted as a heatmap. The different NAs were clustered by amino acid sequence phylogeny. The top panel shows N2-reactive mAbs binding to a panel of NA proteins. The bottom panel shows N1-reactive mAbs binding to a panel of NA proteins. Pie charts represent the frequency of NA-reactive mAbs binding to historic strains (A/Hong Kong/1/1968 rN2 and A/Brevig Mission/1/1918 rN1). (Panel B) Binding of 32 HA reactive mAbs isolated from infected or vaccinated subjects to historical past H3N2 strain (A/Hong Kong/1/1968) rH3 were measured by ELISA. Pie charts represent the comparative frequency of HA-reactive mAbs against A/Hong Kong/1/1968 rH3 protein between the infected and vaccinated individuals.

To determine the breadth of binding of the NA-reactive mAbs induced by infection, ELISA was used to test binding against a diverse panel of rNA proteins (FIG. 3A). All of the N2-reactive mAbs were cross-reacted to all contemporary H3N2 influenza strains, and also a surprising 86% (12 of 14) reacted to the first pandemic H3N2 virus strain known to infect humans (A/Hong Kong/1/1968). Also, 71% (10 of 14) of the antibodies reacted to the H2N2 influenza strain from 1957 that had circulated in humans for the eleven years before the H3N2 strain arose. By comparison, only 40% of infection-induced H3-reactive mAbs were cross-reactive to this 1968 H3N2 strain (FIG. 3B). Similarly, only half of H3-reactive mAbs induced by vaccination in recent years bound to the 1968 H3N2 strain (FIG. 3B). Moreover, 64% (9 of 14) of the N2-reactive mAbs induced by infection were able to bind to avian N2 proteins, including two mAbs with cross-reactivity to heterosubtypic subtypes (N3 and N9) (FIG. 3A). The 2009 pandemic H1N1 influenza strain induced antibodies to HA that were particularly cross-reactive (Li et al., 2012; Wrammert et al., 2011; herein incorporated by reference in their entireties). Analysis conducted during development of embodiments herein demonstrates that this is also true for N1-reactive mAbs to this strain; 67% of mAbs cross-reacted to the 1918 pandemic H1N1 strain, 33% reacted to various human H1N1 strains spanning the entire century, plus 20% bound to heterosubtypic strains (FIG. 3A). Additionally, escape mutants were generated to select N2-reactive mAbs that demonstrated broad NI activity. However, incubating H3N2 (A/Switzerland/9715293/2013) with mAb concentrations up to 250 µg did not generate escape mutants after many passages, even though escape mutants arose from highly conserved HA-stalk mAbs (Anderson et al., 2017; herein incorporated by reference in its entirety). This analysis indicates that the epitopes on NA are highly durable and unlikely to mediate escape by antigenic drift. On the whole, the NA reactive mAbs induced during influenza virus infections are significantly more broadly reactive than antibodies against HA.

NA-Reactive mAbs Show Broad Enzymatic Inhibition Activity In Vitro

Figure 4A:
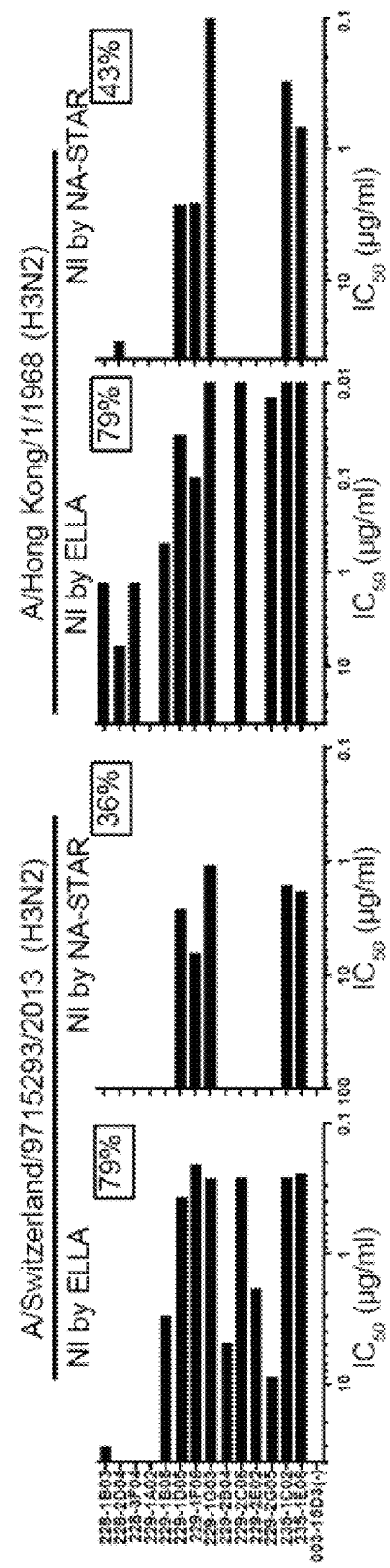
FIGS. 4A-D. NA-reactive mAbs exhibit broadly cross-reactive NA-inhibition and neutralization activity in vitro (A) N2-reactive mAbs were tested for inhibiting NA enzymatic activity via ELLA assays and NA-STAR assays against A/Switzerland/9715293/2013 (H3N2) and A/Hong Kong/1/1968 (H3N2) viruses. (B) N1-reactive mAbs were tested for inhibiting NA enzymatic activity in ELLA assays and NA-STAR assays against A/California/7/2009 (H1N1) virus and A/Brevig Mission/1/1918 (H1N1) rNA protein. (C) NA-reactive mAbs were tested for neutralization by microneutralization (MN) assay using A/Switzerland/9715293/2013 (H3N2) and A/California/7/2009 (H1N1) viruses. Data are represented as half-maximum inhibitory concentration (IC50) (µg/ml). (D) Purified N2 polyclonal antibodies from infected subjects were tested by MN assay against A/Hong Kong/4801/2014 (H3N2) virus. Influenza-non-reactive human mAb 003-15D3 was used as a negative control in the experiments. Data are represented as IC50 (µg/ml). Data are representative of three independent experiments.
Figure 4B:
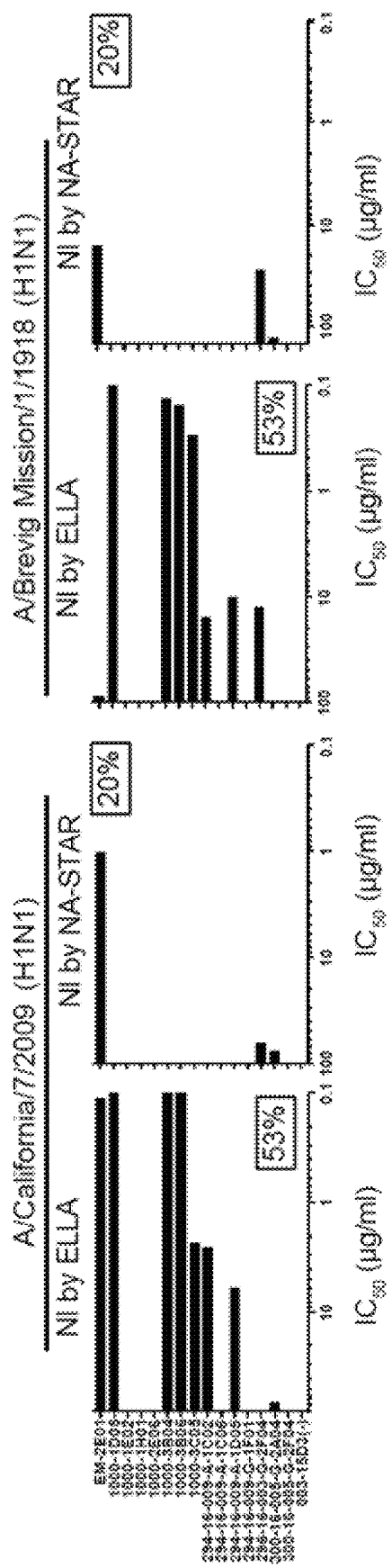

The enzymatic function of NA is to cleave the terminal sialic acid residues allowing viral egress from infected cells. To better access the protective capacity of the NA-reactive mAbs, inhibition of sialic acid cleavage was evaluated using ELLA and NA-STAR assays. ELLA uses the glycoprotein fetuin as a substrate, detecting mAb-mediated inhibition of the sialidase function of NA by any mechanism. These mechanisms include antibody binding near the enzymatic site or through sterically preventing interactions between NA and sialic acid residues on fetuin when bound more distally from the enzymatic site. Conversely, the NA-Star assay uses a small, soluble chemiluminescent substrate, and so more explicitly distinguishes antibodies that directly inhibit the enzymatic activity of NA by binding near the enzymatic site. Using ELLA, 79% (11 of 14) of the N2-reactive mAbs inhibited NA activity against an H3N2 virus, of which about half (5 of 14) were also positive in the NA-STAR assay, demonstrating activity through blockage of the enzymatic domain directly. By either assay, all of these mAbs inhibited the first pandemic H3N2 strain A/Hong Kong/1/1968 (FIG. 4A). Therefore, these mAbs have broad NI activity spanning five decades of H3N2 virus evolution. For mAbs reactive to the 2009 pandemic H1N1 strain, 53% (8 of 15) had NI activity by any means as detected by ELLA, and 20% blocked the enzymatic domain, showing inhibition via the NA-STAR assay. As with the N2-reactive mAbs, N1-reactive mAbs had broad activity against the 1918 pandemic strain A/Brevig Mission/1/1918 (FIG. 4B). These studies demonstrate that the majority of human antibodies against NA inhibit the enzymatic activity of this protein on highly divergent influenza strains.

Figures 4C, 4D:
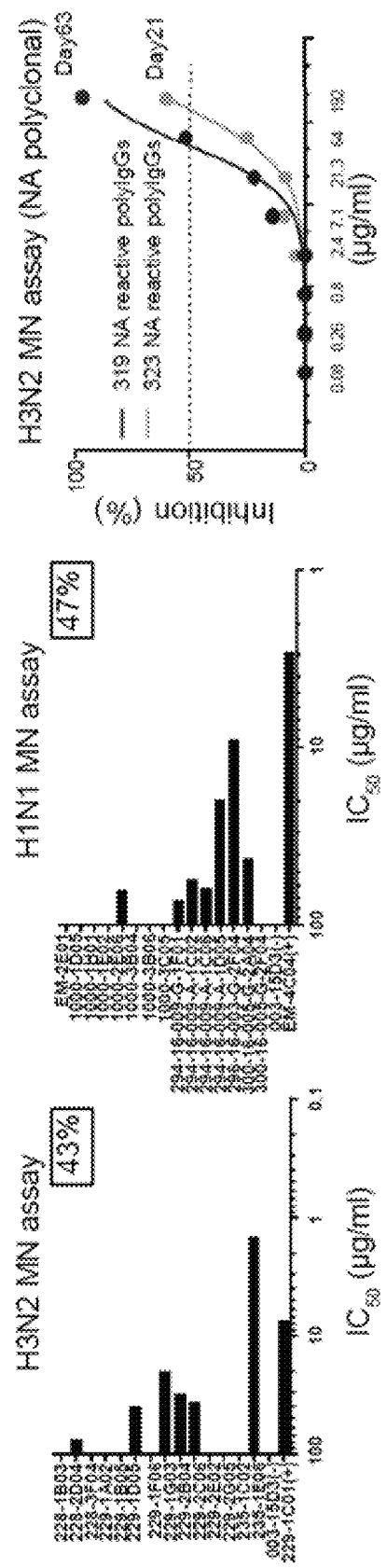

NA-Reactive Human Monoclonal and Long-Term Polyclonal Antibodies have High Neutralization Activity In Vitro Microneutralization (MN) measures the inhibition of influenza virus replication in vitro, providing another correlate of protection. In total, 45% of the NA reactive mAbs were able to neutralize viruses related to the infecting strain, including; 43% (6 of 14) of the N2-reactive mAbs and 47% (7 of 15) of the N1-reactive mAbs (FIG. 4C). To ensure that the anti-NA antibody response was contributing to long-term serum immunity, NA-reactive polyclonal antibodies were isolated by affinity purification from two of the patients and tested them by using MN assays (Lee et al., 2016; herein incorporated by reference in its entirety). One serum sample was collected at the predicted peak of the immune response (day 21 post-infection), and the other was obtained well after the patient was convalescent at two months (day 63 post-infection). The isolated NA-reactive polyclonal antibodies also readily protected MDCK cells from infection in vitro (FIG. 4D). These data show that NA-reactive antibodies commonly exhibit neutralization activity, inhibiting virus replication, and contribute to long-term serum immunity.

Identification of NA Residues Crucial for mAb Binding

Figure 5A:
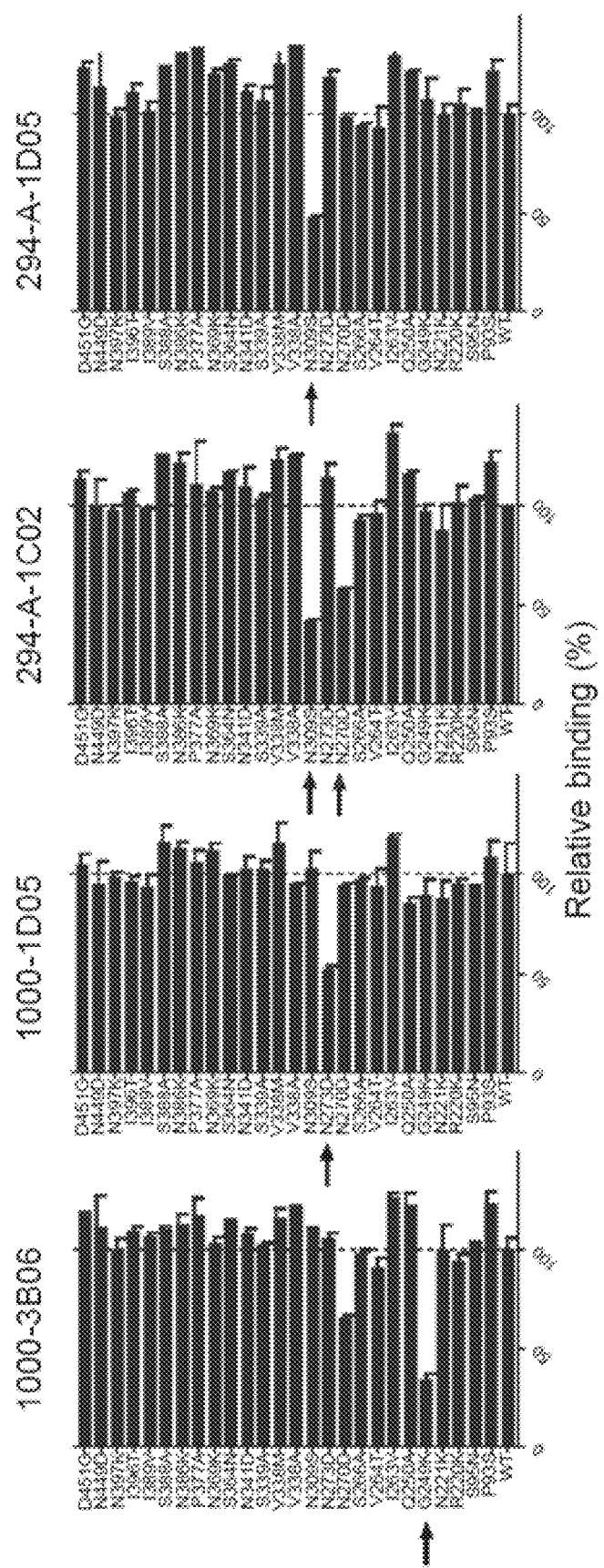
FIGS. 5A-D. Identification of critical epitopes targeted by NA-reactive mAbs (A) Binding of four N1-reactive mAbs (1000-3B06, 1000-1D05, 294-A-1C02 and 294-A-1D05) to A/California/7/2009 (H1N1) NA mutant proteins transiently expressed on the surface of 293T cells. Hyper-immune mouse serum against A/California/7/2009 (H1N1)-X179A virus was used as a positive control and for examining the expression of NA. Binding to A/California/7/2009 wide type NA is shown in the last bar labeled "WT". Data are represented as mean±SD. Data are representative of two independent experiments performed in duplicate. (B) Modeling of N1 was done using PyMOL to show the 4 critical amino acids involved in the binding of the N1-reactive mAbs (PDB: 3TI6) (Vavricka et al., 2011). (C) Binding of three N2-reactive mAbs (229-1D05, 235-1C02 and 235-1E06) to 12 A/Minnesota/11/2010 (H6N2-PR8 backbone) NA mutant viruses. Data are represented as mean±SD. Data are representative of two independent experiments performed in duplicate. (D) Modeling of N2 protein was done using PyMOL to show the three critical amino acid involved in the binding of the N2-reactive mAbs (PDB:4K1J) (Wu et al., 2013).
Figure 5B:
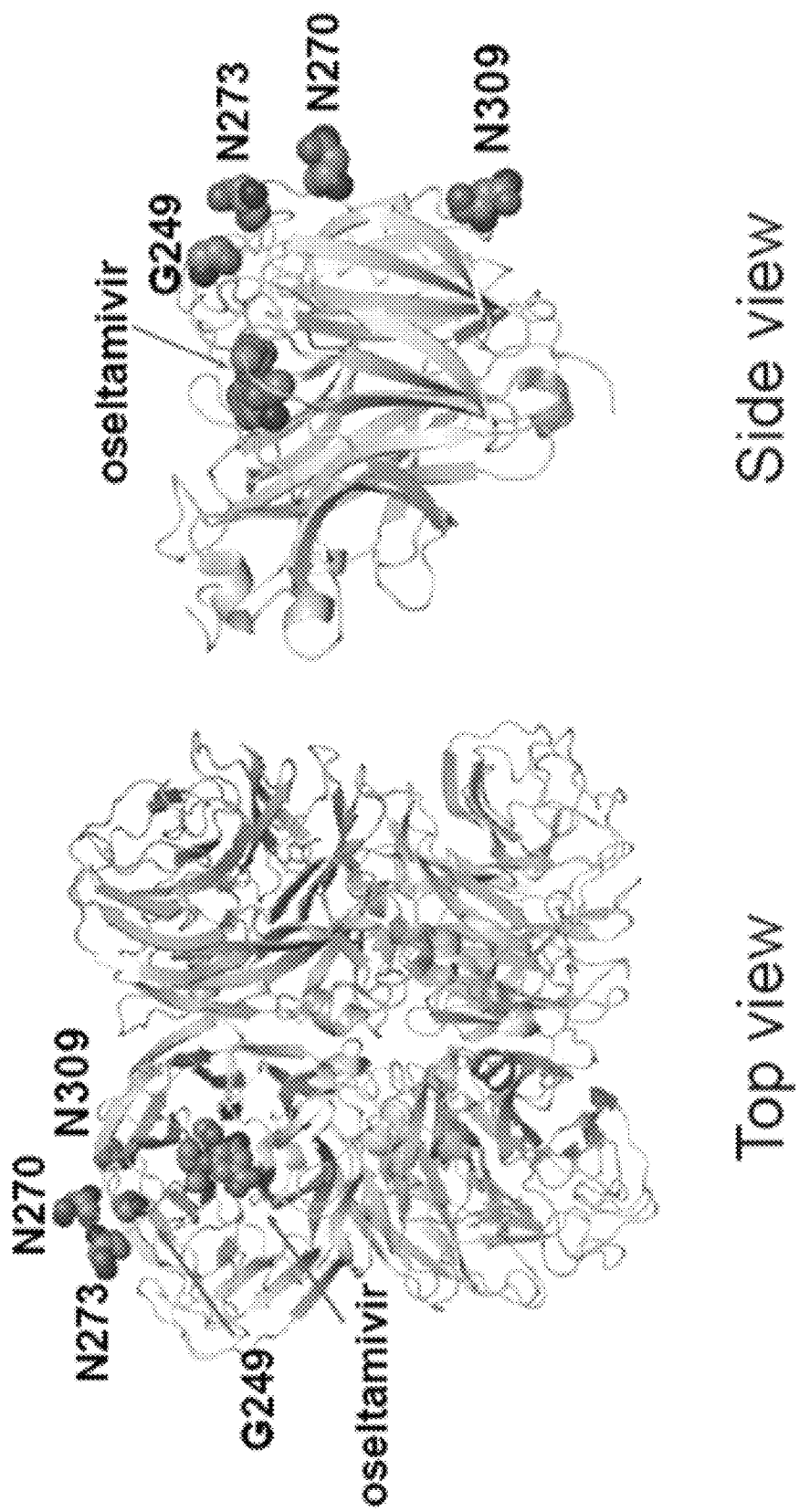
Figure 5C:
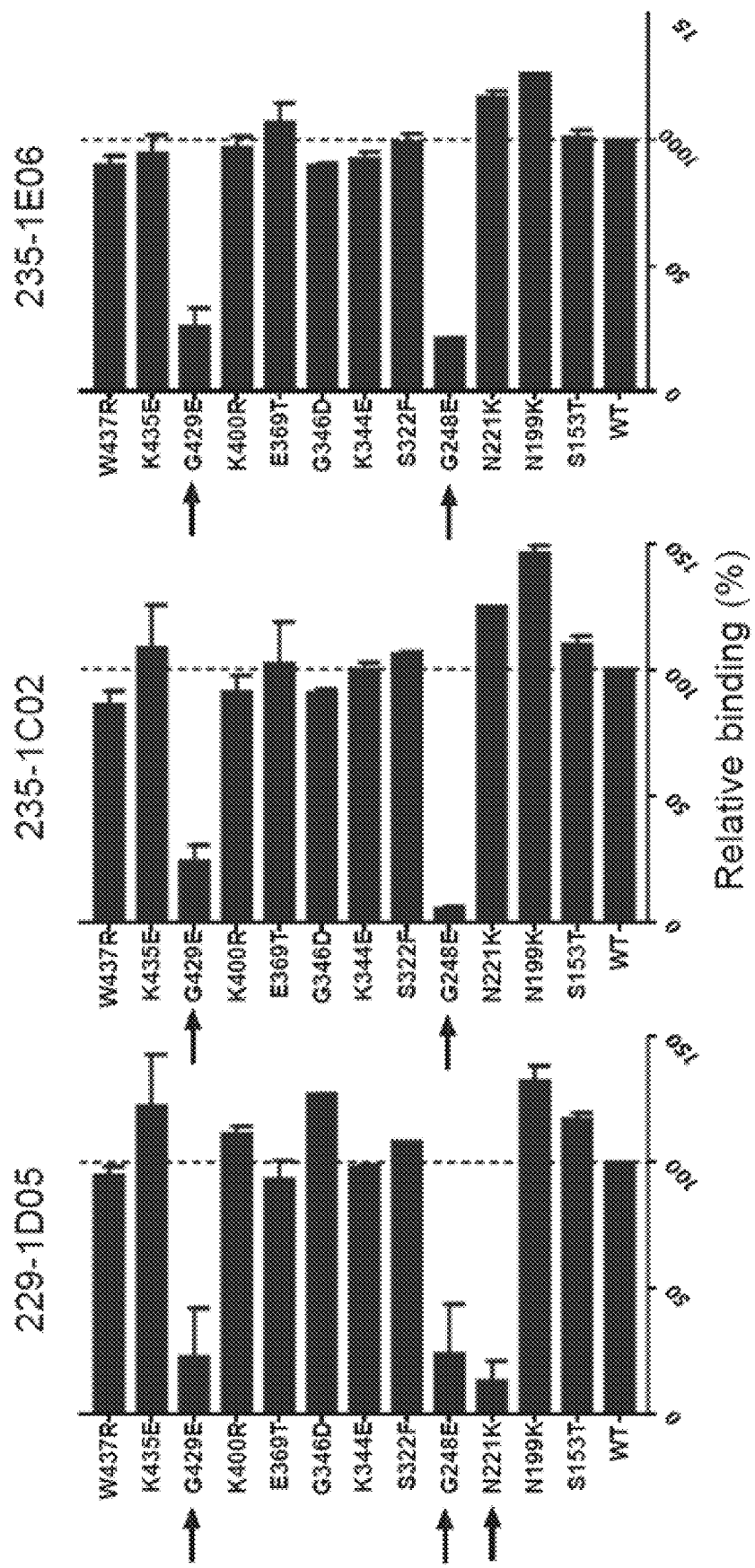
Figure 5D:
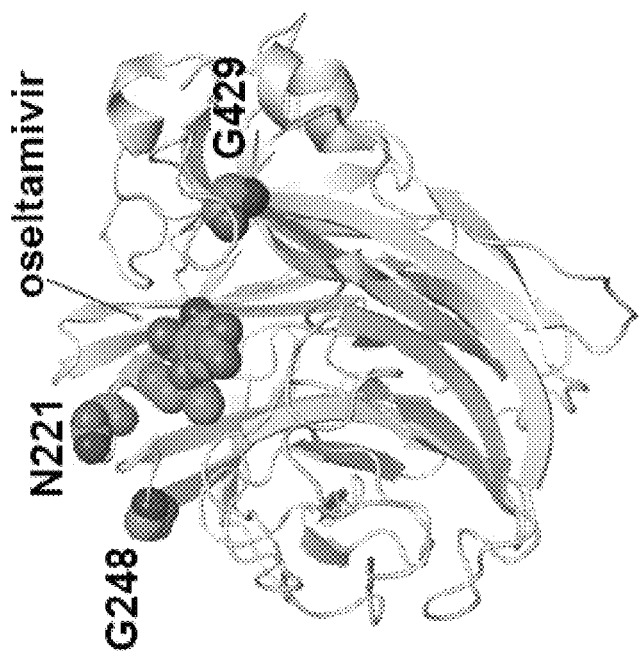
Figure 5D:
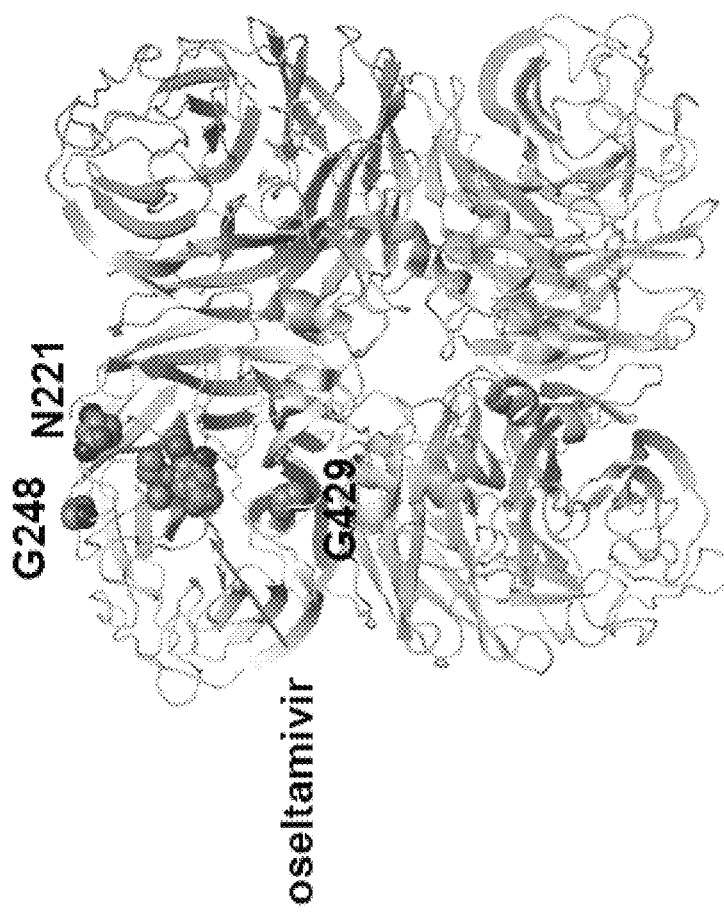
Figure 6A:
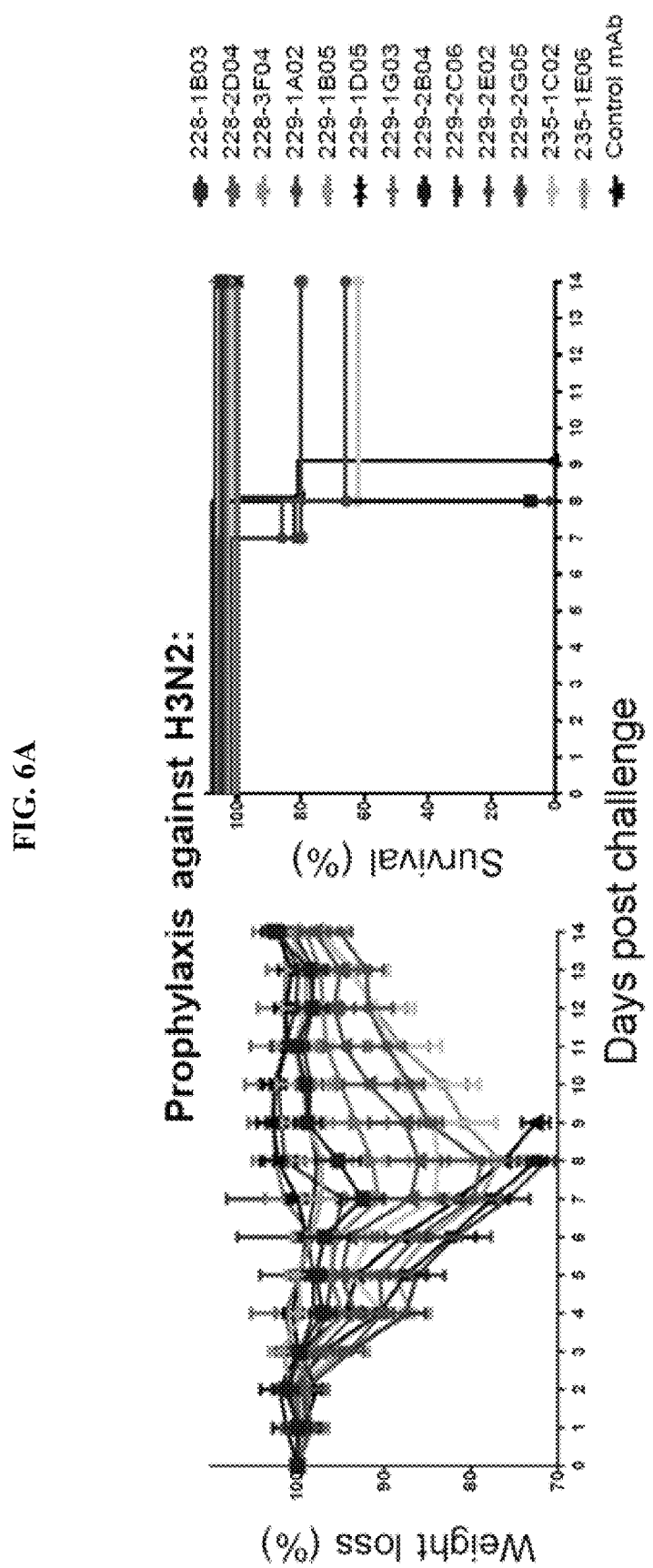
FIGS. 6A-C. NA-reactive mAbs are protective in a prophylactic setting in vivo (A-C) Six week-olds female BALB/c mice (5 per experimental condition) were injected intraperitoneally (i.p.) with 5 mg/kg of each NA-reactive mAb individually or with an irrelevant negative control human mAb 2 h prior to challenge with a lethal dose (10 LD50) of virus. The percentage of initial body weight and survival were plotted for each antibody and compared to untreated mice. (A) N2-reactive mAbs were injected to mice and then infected with 10 LD50 of A/Philippines/2/1982 (H3N2-X-79) virus. Percent of initial weight and survival rate are shown. (B) N1-reactive mAbs were injected to mice and then infected with 10 LD50 of A/Netherlands/602/2009 virus (pandemic H1N1). Percent of initial weight and survival rate are shown. (C) N1-reactive mAbs were injected to mice and then infected with 10 LD50 of A/Vietnam/1203/2004 (H5N1-PR8 reassortant) avian influenza virus. Percent of initial weight and survival are shown. Data are represented as mean±SD. Influenza-non-reactive human mAb 003-15D3 was used as a negative control in all experiments.
Figure 6B:
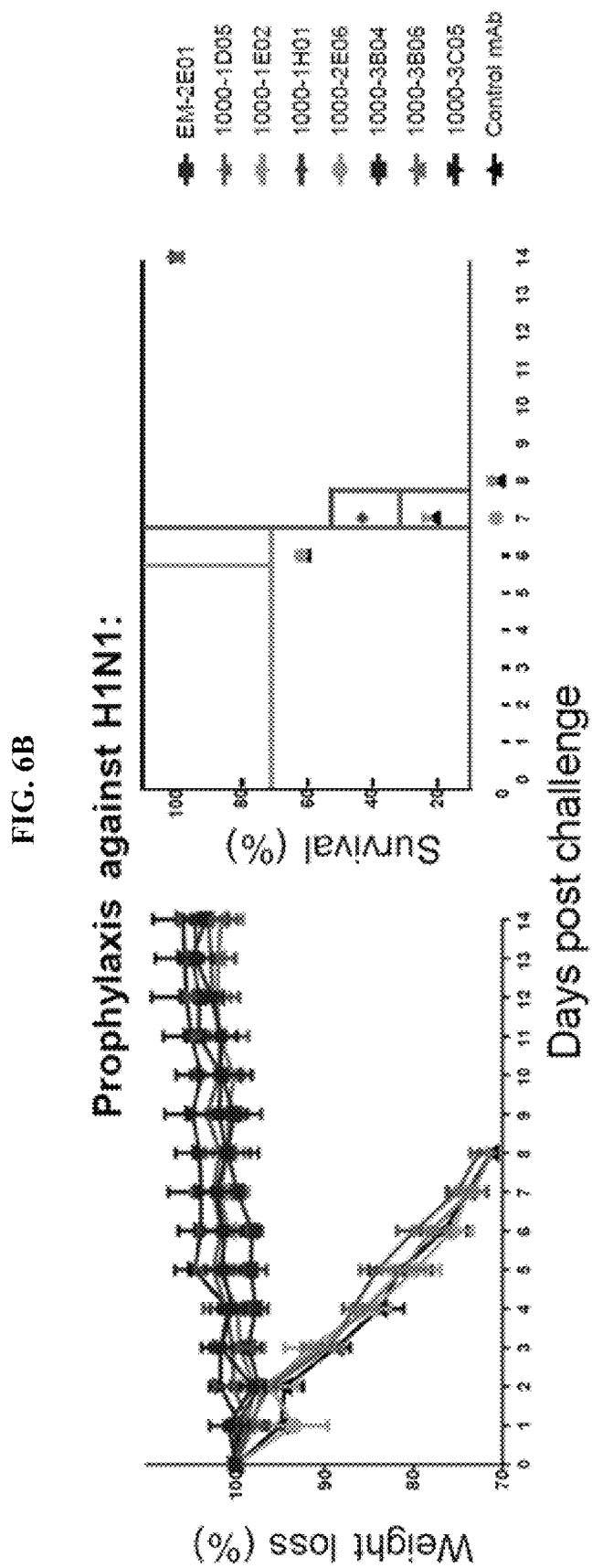
Figure 6C:
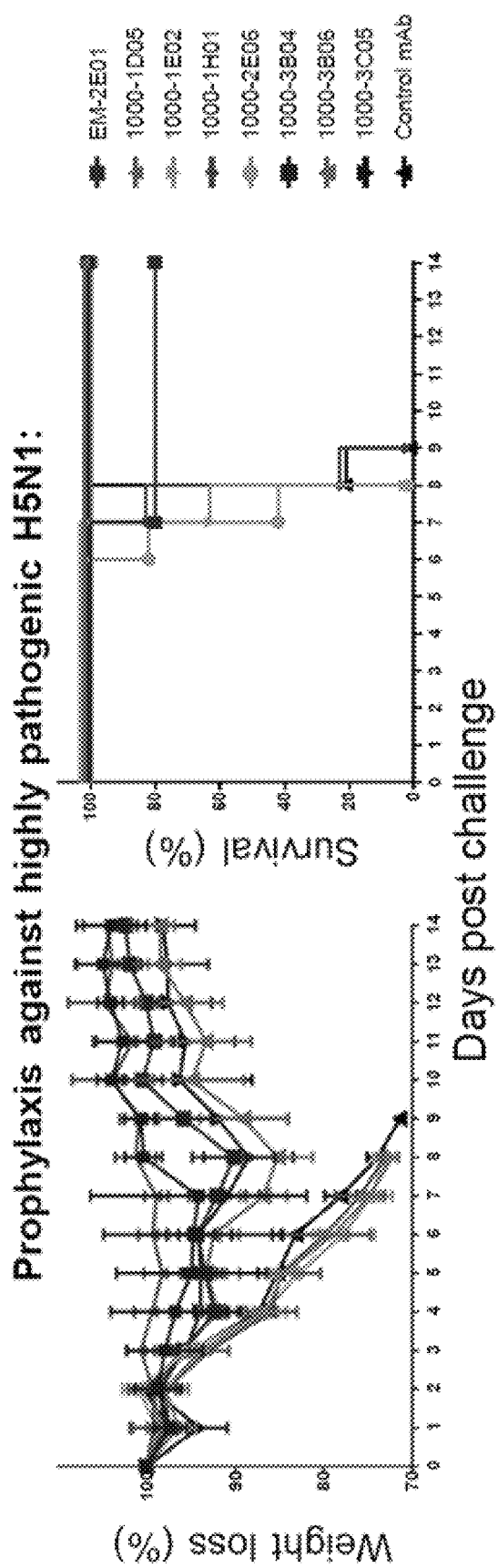

To map the epitopes recognized by the N1-reactive mAbs, 26 single amino acid mutant NA proteins from the 2009 pandemic influenza strain were expressed in HEK293 cells (Wan et al., 2015; herein incorporated by reference in its entirety). Cell-based ELISAs were carried out to test the binding of the N1-reactive mAbs to the mutant proteins. A G249K mutation significantly affected the binding of 1000-3B06 (70% decrease compared to the wild-type N1). The N273D mutation reduced the binding of 1000-1D05 compared to the wild-type N1 protein. Furthermore, the N309S mutation affected both 294-A-1C02 and 294-A-1D05 binding (FIG. 5A) Amino acids N273 and N309 are 99.7% (6835 of 6855 H1 influenza strains) conserved in H1N1 viruses isolated from 1918 until now in the United States. The G249 site is also conserved in H1N1 viruses (90.3%, 6196 of 6855 H1 influenza strains). These residues are all located on the NA head (FIG. 5B). To map the epitope(s) targeted by the N2-reactive mAbs, ELISA was used to test the binding affinity of N2-reactive mAbs to 12 single amino acid mutants of N2 expressed on an A/Minnesota/11/2010 (H6N2-PR8 backbone) purified virus. Three amino acids (N221, G248, and G429) on the NA enzymatic conserved domain are critical for the binding of 229-1D05, 235-1C02 and 235-1E06 (FIGS. 5C and 5D). Consistently, all three of these mAbs were also positive in the NA-STAR assay (FIG. 4A). These results show that NA-reactive mAbs are readily induced against highly conserved epitopes on NA and so are excellent targets for vaccines as well as making the mAbs attractive potential therapeutics.

NA-Reactive mAbs Protect Mice Against Divergent Influenza Viruses

The broad cross-reactivity, as well as widespread in vitro NI activity of NA-reactive mAbs, indicates that they are broadly protective in vivo. The prophylactic protection against challenge was measured with divergent strains in vivo. Half-maximal lethal dosages ($LD_{50}$) of the influenza virus were determined. Mice received 5 mg/kg of NA-reactive mAb or the same dose of a non-binding control mAb by intraperitoneal injection (i.p.). Two hours later, the mice were lethally challenged with 10 LD50 of influenza virus by intranasal inoculation. Recent H3N2 isolates do not replicate well in the mouse model but historical strains like A/Philippines/2/1982 (H3N2, X-79) infect mice readily. This virus is phylogenetically distant from recent influenza virus strains, including those that cause the human infections from which the mAbs are derived. Thus, this virus also provides an opportunity to measure the breadth of protection for the N2-reactive mAbs in vivo. A selection of N2-reactive mAbs representing all overlapping epitopes were tested. 84% (11 of 13) of the N2-reactive mAbs showed partial or full protection in the prophylactic challenge experiment against this 35-year-old H3N2 influenza strain (FIG. 6A). The protection conferred was consistent with the breadth of binding and NI activity of these mAbs. Moreover, non-neutralizing NA-reactive mAbs also provided in vivo prophylactic protection. These data show that neutralizing and non-neutralizing N2-reactive mAbs provide broad prophylactic protection against H3N2 influenza strains in vivo.

The larger panel of group 1 influenza strains available for murine challenge studies allowed a more in-depth analysis of the breadth of protection of NA-reactive mAbs. First, mice treated with N1-reactive mAbs were challenged with a 2009 pandemic H1N1 isolate (A/Netherlands/602/2009). Five out of eight of the mAbs from the 2009-2010 cohort completely protected mice against weight loss and mortality after challenge, whereas mice treated with control mAb lost weight rapidly and were euthanized by day eight post-infection (FIG. 6B). Four out of five of the mAbs that prophylactically protected against H1N1 infection (4 of 8 in total) also provided 100% protection from a highly divergent avian influenza virus strain (A/Vietnam/1203/2004, H5N1) (FIG. 6C). Thus, half of all mAbs induced against N1 in individuals infected with the 2009 pandemic H1N1 strain provided broad protection against an H5N1 strain. This frequency was far exceeding the 10% of HA-reactive mAbs that arose against this H1N1 strain that even bound to H5 (Li et al., 2012; Wrammert et al., 2011; herein incorporated by reference in their entireties). Together, these results indicate that when induced against common infectious influenza virus strains, NA-reactive mAbs are outstanding mediators of broadly protective immunity, even to divergent avian influenza virus strains with pandemic potential.

NA-Reactive mAbs are Excellent Alternatives for Influenza Treatment or Prophylaxis NA inhibitors such as oseltamivir have become the standard of care for treating influenza virus infections as they have proven efficacy for improving the outcome of disease (Genentech, 2016; herein incorporated by reference in its entirety). However, these drugs suffer from dramatic loss of effectiveness if not administered within the first 48 hours of infection. Furthermore, the evolution of resistant influenza strains is now common, severely limiting the usefulness of these drugs. NA-reactive mAbs may be improved alternatives as therapeutic NA-inhibitors, or even more efficacious when efficiently elicited by vaccination. As the NA—inhibition antibodies identified had activity against a wide spectrum of influenza virus strains, we tested the activity of these mAbs compared to oseltamivir. Using bio-layer interferometry, an assay was devised to competitively measure the binding of oseltamivir versus NA-reactive mAbs to the NA protein. Binding of three of the enzymatic domain-targeting mAbs (NA-STAR assay positive, 229-1D05, 229-1F06, and 229-1G03) is inhibited by prior saturation of NA of an oseltamivir-sensitive strain with oseltamivir (FIGS. 7A and 9). This inhibition demonstrates that the binding footprint of the mAbs overlaps at least to some degree with the binding pocket occupied by oseltamivir. Oseltamivir acts by blocking the enzymatic domain, allowing its activity against a particular influenza virus strain to be assessed by the NA-STAR assay. While oseltamivir had virtually no NI activity on a typical oseltamivir-resistant strain (A/Texas/12/2007 E119V), all five of the enzymatic domain-binding mAbs isolated in this study, which is 36% of the N2-reactive mAbs isolated, inhibited the NA activity of this resistant strain. For 229-1G03 and 235-1E06, the $IC_{50}$ is nearly identical against the sensitive and resistant strains (FIG. 7B).

Figure 7A:
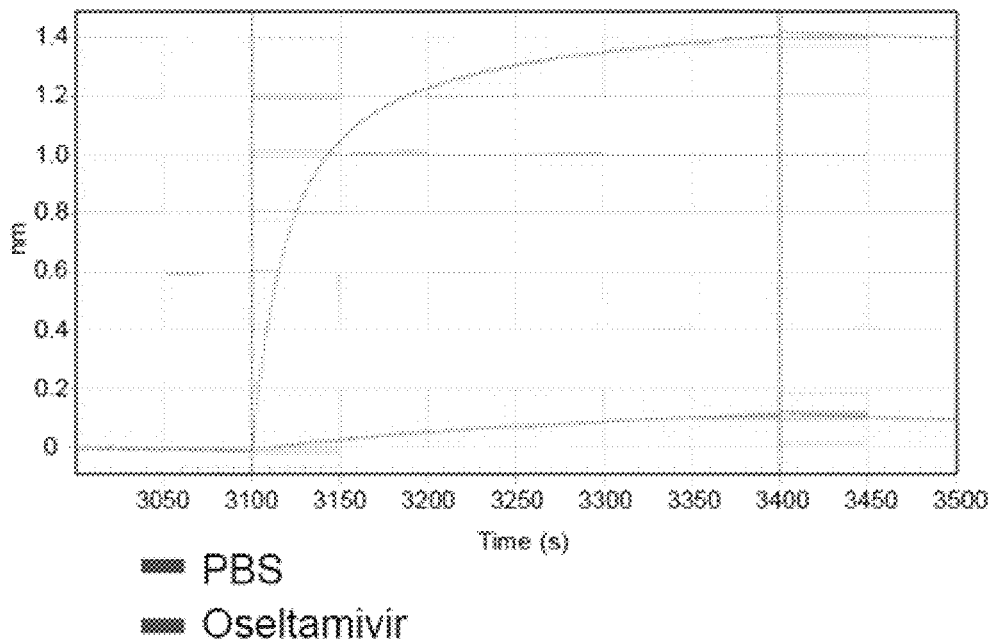
FIGS. 7A-D. NA-reactive mAbs are protective in a therapeutic setting in vivo (A) Binding competition between the N2-reactive mAb 229-1D05 and oseltamivir to A/Texas/50/2012 rNA was measured by bio-layer interferometry. (B) N2-reactive mAbs were tested for inhibiting NA enzymatic activity via NA-STAR assay against A/Washington/01/2007 (oseltamivir-sensitive strain) and A/Texas/12/2007 E119V (oseltamivir-resistant strain) H3N2 viruses. (C-D) Six week-olds female BALB/c mice (5 per experimental condition) were infected with a lethal dose (10 LD50) of virus and then administered i.p. with 10 mg/kg of NA-reactive mAbs or an irrelevant negative control human mAb 48 h after infection. The percentage of initial body weight or survival was plotted for each NA-reactive mAb and compared with untreated mice. (C) N1-reactive mAbs were injected to mice infected with 10LD50 of A/Netherlands/602/2009 virus (pandemic H1N1). Percent of initial weight and survival are shown. (D) N2-reactive mAbs were administered to mice infected with A/Philippines/2/1982 (H3N2-X-79) virus. Percent of initial weight and survival rates are shown. Data are represented as mean±SD. Influenza-non-reactive human mAb 003-15D3 was used as a negative control in all challenge experiments.
Figure 7B:
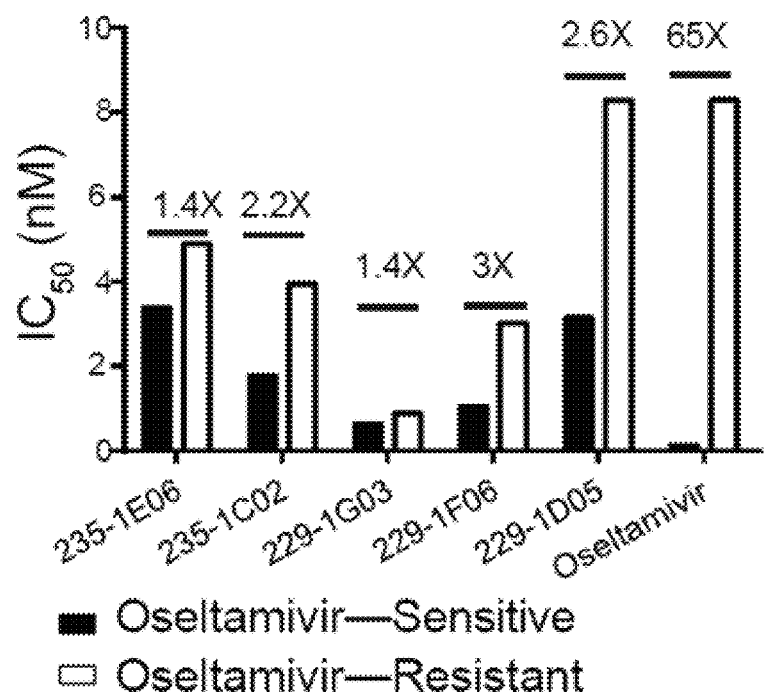
Figure 7C:
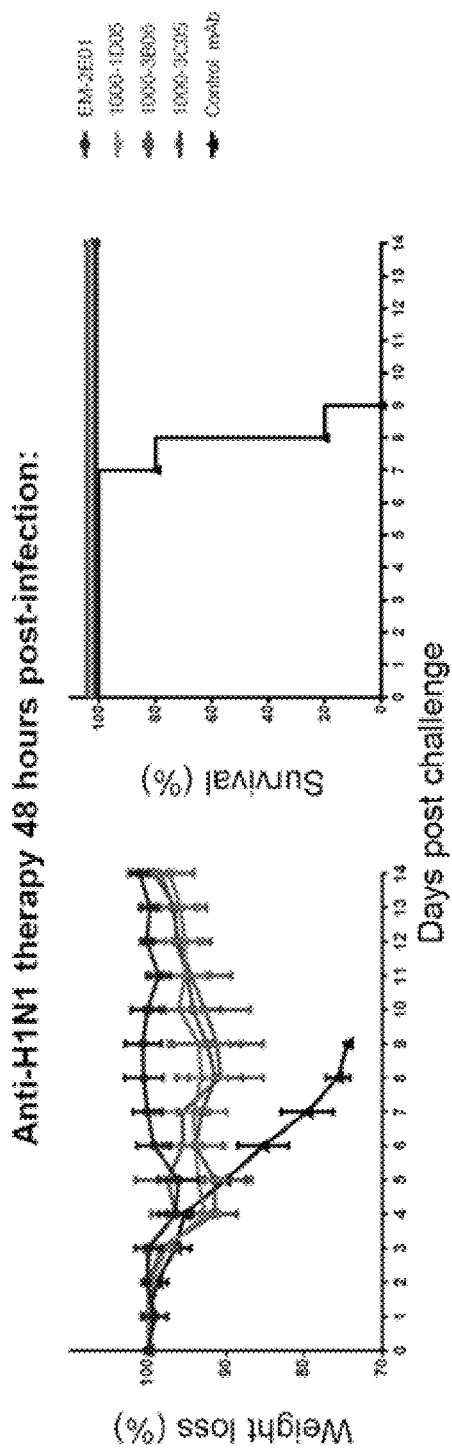
Figure 7D:
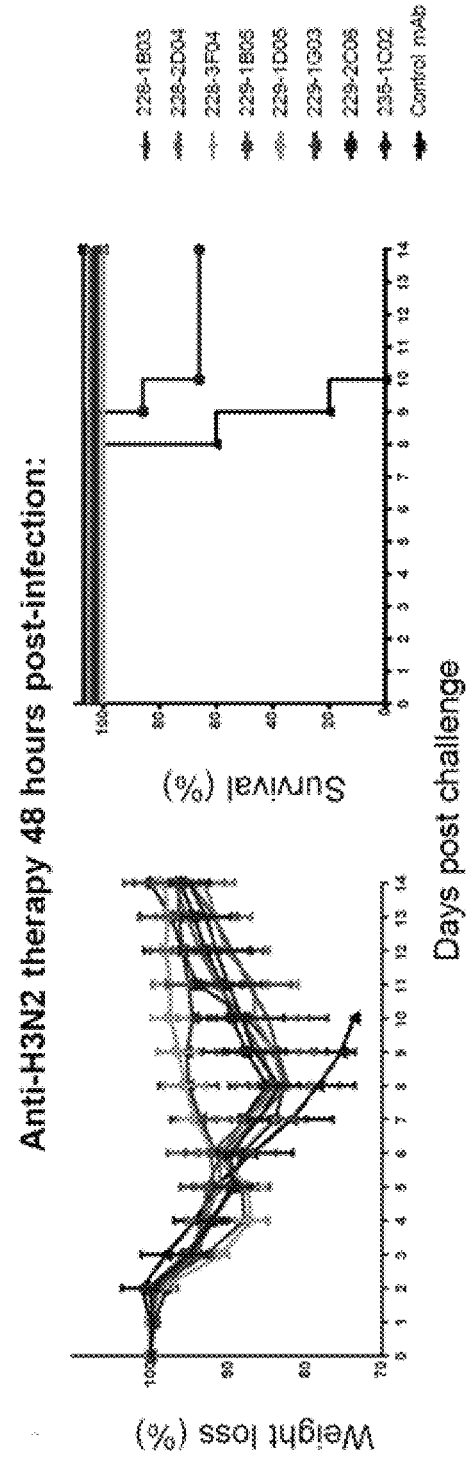

Additionally, the therapeutic efficacy of the NA-reactive mAbs that were protective as prophylactics were also analyzed directly. Mice that were lethally infected with 10 $LD_{50}$ of influenza virus were treated with 10 mg/kg of NA-reactive mAbs 48 hours post-infection. All four of the N1-reactive mAbs fully rescued infected mice from severe weight loss and mortality after 2009 pandemic H1N1 influenza virus challenge (FIG. 7C). Similarly, 88% (7 of 8) of the N2-reactive mAbs proffered full recovery to the mice challenged with an H3N2 virus (FIG. 7D). In sharp contrast, all mice in the control mAb group had to be euthanized around day nine post-infection because of severe weight loss. These results show that the NA-reactive mAbs are useful therapeutically, even after 48 hours of influenza virus infection, indicating they are alternatives to NA inhibitors such as oseltamivir. With improved vaccine formulations to induce NA antibodies the same benefits as NA-inhibiting drugs are prophylactically elicited without the need for early administration. Further, unlike NA-inhibiting medications, which lose effectiveness due to the emergence of resistant strains, administration of booster vaccines would control viral resistance.

All publications and patents provided herein are incorporated by reference in their entireties. Various modifications and variations of the described compositions and methods of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention that are obvious to those skilled in the relevant fields are intended to be within the scope of the present invention.

Sequences

The following antibody chain and CDR sequences are referenced throughout the specification and claims by their corresponding SEQ ID NOS. and/or names.

---

228-14-035-2D04

Heavy:
(SEQ ID NO: 1)
GAGGTGCAGCTGGTGGAGTCTGGGGGAGGCTTGGTTAAGCCTGGACAATCGCTT
AGACTCTCCTGTGCAGCCTCTGGATTCACTTTCACTAATGCCTGGATGAGTTGGG
TCCGCCAGGCTCCAGGGAAGGGGCTGGAGTGGGTTGGCCGTATCAAAACCAAAA
CTGAAGGCGAGACAGTAGACTACGCTGCACCCGTGAAAGGCAGAATCACCATCT
CAAGAGATGACTCAAAGAACATGGTGTATCTGCAATTGAAGAGCCTGAAAATCG
AGGACGCAGCCGTTTACTACTGTACCACAGGTCTTACACGTTCGAGTCTCGGCGG
CTTCGTTGACTACTGGGGCCCGGGAACCCTGGTCACCGTCTCCTCAGC (SEQ ID NO: 2)
EVQLVESGGGLVKPGQSLRLSCAASGFTFTNAWMSWVRQAPGKGLEWVGRIKTKTEGETV
DYAAPVKGRITISRDDSKNMVYLQLKSLKIEDAAVYYCTTGLTRSSLGGFVDYWGPGTLV
TVSS

CDRH1:
(SEQ ID NO: 3)
AATGCCTGGATGAGT (SEQ ID NO: 4)
NAWMS

CDRH2:
(SEQ ID NO: 5)
CGTATCAAAACCAAAACTGAAGGCGAGACAGTAGACTACGCTGCACCCGTGAAA
GGC (SEQ ID NO: 6)
RIKTKTEGETVDYAAPVKG

CDRH3:
(SEQ ID NO: 7)
ACCACAGGTCTTACACGTTCGAGTCTCGGCGGCTTCGTTGACTAC (SEQ ID NO: 8)
TTGLTRSSLGGFVDY

Kappa:
(SEQ ID NO: 9)
GACATCGTGATGACCCAGTCTCCGGACTCCCTGACTGTGTCTCTGGGCGAGAGGG
CCACCATCAACTGCAGGTCCAGCCAGACTGTTTTGTCCAGCTCCAACAATGAGAA
CTTCTTAGCTTGGTACCAGCAGAAATCAGGACAGCCTCCTAACCTGCTCATTTAC
TGGGCATCTACCCGGGCATCCGGGGTCCCTGACCGATTCAGTGGCAGCGGGTCTG
GGACAGATTTCACTCTCACTATCAGCAGCCTGCAGACTGAAGATGTGGCAGTTTA
TTACTGTCTCCAATATCTTACTACTCCTCGGACGTTCGGCCAAGGGACCAAGGTG
GAAATCAAAC (SEQ ID NO: 10)
DIVMTQSPDSLTVSLGERATINCRSSQTVLSSSNNENFLAWYQQKSGQPPNLLIYWAS
TRASGVPDRFSGSGSGTDFTLTISSLQTEDVAVYYCLQYLTTPRTFGQGTKVEIK -continued

CDRK1:
(SEQ ID NO: 11)
AGGTCCAGCCAGACTGTTTTGTCCAGCTCCAACAATGAGAACTTCTTAGCT (SEQ ID NO: 12)
RSSQTVLSSSNNENFLA

CDRK2:
(SEQ ID NO: 13)
TGGGCATCTACCCGGGCATCC (SEQ ID NO: 14)
WASTRAS

CDRK3:
(SEQ ID NO: 15)
CTCCAATATCTTACTACTCCTCGGACG (SEQ ID NO: 16)
LQYLTTPRT

---

229-14-036-1D05

---

Heavy:
(SEQ ID NO: 17)
GTGCAGCTGGTGGAGTCTGGGGGAGGCTTGGTCAAGCCTGGAGGGTCCCTGAGA
CTCTCCTGTGCAGCCTCTGGATTCACCTTCAGTGACTACTACATGAGCTGGATCC
GCCAGGCTCCAGGGAAGGGGCTGGAGTGGATTTCATACATTAGTAGTAGTAGTA
CTTACACAGACTACGCAGACTCTGTGAAGGGCCGATTCACCGTCTCCAGAGACA
ACGCCAAGAACTCATTGTATCTACAAATGAACAACCTGAGAGCCGAGGCACGG
CCGTGTATTACTGTGCGACCGTGGCCGACACCGCGTATAGCAGAGGCAGGCCAC
AAAATTACCCACTTTGACAACTGGGGCCAGGGAACCCTGGTCACCGTCTCCTCAGC (SEQ ID NO: 18)
VQLVESGGGLVKPGGSLRLSCAASGFTFSDYYMSWIRQAPGKGLEWISYISSSSTYTD
YADSVKGRFTVSRDNAKNSLYLQMNNLRAEDTAVYYCATVADTAYSRGRPQITHF
DNWGQGTLVTVSS

CDRH1:
(SEQ ID NO: 19)
GACTACTACATGAGC (SEQ ID NO: 20)
DYYMS

CDRH2:
(SEQ ID NO: 21)
TACATTAGTAGTAGTAGTACTTACACAGACTACGCAGACTCTGTGAAGGGC (SEQ ID NO: 22)
YISSSSTYTDYADSVKG

CDRH3:
(SEQ ID NO: 23)
GCGACCGTGGCCGACACCGCGTATAGCAGAGGCAGGCCACAAATTACCCACTTT
GACAAC (SEQ ID NO: 24)
ATVADTAYSRGRPQITHFDN

Lambda:
(SEQ ID NO: 25)
TCCTATGAGCTGACTCAGCCACCCTCAATGTCCGTGTCCCCAGGACAGACAGCCA
CCATCACCTGTTTTGGAGATAAATTGGGGGAAAAGTATGCTTACTGGTATCAGCA
GAAGCCTGGCCAGTCCCCTCTACTGGTCATCTATCAAGATACCAAGCGGCCCTCA
GGGATCCCTGAGCGGTTCTCTGGCTCCAACTCTGGGAACACAGCCACTCTGACCA
TCAGCGGGACCCAGGCTATGGATGAGGCTGACTATTACTGTCAGACGTGGGACA
GCACCCTTGTGTTTTTCGGCGGAGGGACCAAGCTGACCGTCCTAG (SEQ ID NO: 26)
SYELTQPPSMSVSPGQTATITCFGDKLGEKYAYWYQQKPGQSPLLVIYQDTKRPSGIP
ERFSGSNSGNTATLTISGTQAMDEADYYCQTWDSTLVFFGGGTKLTVL

CDRL1:
(SEQ ID NO: 27)
TTTGGAGATAAATTGGGGGAAAAGTATGCTTAC (SEQ ID NO: 28)
FGDKLGEKYAY

CDRL2:
(SEQ ID NO: 29)
CAAGATACCAAGCGGCCCTCA (SEQ ID NO: 30)
QDTKRPS

CDRL3:
(SEQ ID NO: 31)
CAGACGTGGGACAGCACCCTTGTGTTT (SEQ ID NO: 32)
QTWDSTLVF

---
229-14-036-1G03
---

Heavy:
(SEQ ID NO: 33)
GTGCAGCTGGTGGAGTCTGGGGGAGGCGTGGTCCAGCCTGGGGGGTCCCTAAGA
CTCTCCTGTGCAGTGTCTGGACTCACCATCAATGACCTTGTCATCCACTGGGTCC
GCCAGCCTCCAGACAAGGGGCTGGAGTGGGTGGCAGTTATGGGGTATGATGGCG
GAAACAAAGACTATGCAGAATCCGTGAAGGGCCGATTCAGCATCTCCGGGGACA
ATCCCCAGAACACACTGTATCTGCAGATAAACAGCCTGAGAGTCGAGGACACGG
CTGTATATTACTGTGCGAGAGCATCATACTTCGGGGAGTTAAGAGACGAGTACTA
CTCCTTCGCCATGGACGTCTGGGGCCAAGGGACCACGGTCACCGTCTCCTCAG (SEQ ID NO: 34)
VQLVESGGVVQPGGSLRLSCAVSGLTINDLVIHWVRQPPDKGLEWVAVMGYDGGNKDYA
ESVKGRFSISGDNPQNTLYLQINSLRVEDTAVYYCARASYFGELRDEYYSFAMDVWGQGT
TVTVSS

CDRH1:
(SEQ ID NO: 35)
GACCTTGTCATCCAC (SEQ ID NO: 36)
DLVIH

CDRH2:
(SEQ ID NO: 37)
GTTATGGGGTATGATGGCGGAAACAAAGACTATGCAGAATCCGTGAAGGGC (SEQ ID NO: 38)
VMGYDGGNKDYAESVKG

CDRH3:
(SEQ ID NO: 39)
GCGAGAGCATCATACTTCGGGGAGTTAAGAGACGAGTACTACTCCTTCGCCATG
GACGTC (SEQ ID NO: 40)
ARASYFGELRDEYYSFAMDV

Kappa:
(SEQ ID NO: 41)
GAAATTGTGTTGACGCAGTCTCCAGGCACCCTGTCTTTGTCTCCAGGGGAAAGAG
GCACCCTCTCCTGCAGGGCCAGTCAGAGTGTTAGTAGGAGTTACTTAGCCTGGTA
CCAGCAGAAACCTGGCCAGGCTCCCAGGCTCCTCATCTATGGTGCATCCAGCAG
GGCCACTGGCATCCCAGACAGGTTCAGTGGCAGTGGGTCTGGGACAGACTTCAC
TCTCACCATCAGCAGACTGGAGCCTGAAGATTTTGCACTGTATTACTGTCAGCTG
TATGGTACCTCACCTCCGTACACTTTTGGCCAGGGGACCAAGGTGGAAATCAAAC (SEQ ID NO: 42)
EIVLTQSPGTLSLSPGERGTLSCRASQSVSRSYLAWYQQKPGQAPRLLIYGASSRATGIP
DRFSGSGSGTDFTLTISRLEPEDFALYYCQLYGTSPPYTFGQGTKVEIK

CDRK1:

(SEQ ID NO: 43)
AGGGCCAGTCAGAGTGTTAGTAGGAGTTACTTAGCC (SEQ ID NO: 44)
RASQSVSRSYLA

CDRK2:

(SEQ ID NO: 45)
GGTGCATCCAGCAGGGCCACT (SEQ ID NO: 46)
GASSRAT

CDRK3:

(SEQ ID NO: 47)
CAGCTGTATGGTACCTCACCTCCGTACACT (SEQ ID NO: 48)
QLYGTSPPYT

---
229-14-036-2B04
---

Heavy:

(SEQ ID NO: 49)
GAGGTGCAGCTGGTGGAGTCTGGGGGAGGCTTGGTAAAGCCTGGGGGGTCCCTT
AGACTCTCCTGTGCAGCCTCTGGATTCACTGTCAGTAATGCCTGGATGAGCTGGG
TCCGCCAGGCTCCAGGAAAGGGGCTGGAGTGGGTTGGTCGTATTAAGAAAGAAA
GTGAGGGTGGGACAATAGACTACGGTGCACCCGTGAAAGGCAGATTCACCATCT
CAAGAGATGAATCAAAAAACATATTGTATCTGCACATGAAGAGCCTGATAACCG
ATGACACAGCCGTGTACTACTGTACCATCCCGAATCCTCAAATTGTGGTGGTGAC
TACTACTCCACATTCCCATTGGGGCCAGGGAACCCTGGTCACCGTCTCCTCAGC (SEQ ID NO: 50)
EVQLVESGGGLVKPGGSLRLSCAASGFTVSNAWMSWVRQAPGKGLEWVGRIKKESEGGTI
DYGAPVKGRFTISRDESKNILYLHMKSLITDDTAVYYCTIPNPQIVVVTTTPHSHWGQGT
LVTVSS

CDRH1:

(SEQ ID NO: 51)
AATGCCTGGATGAGC (SEQ ID NO: 52)
NAWMS

CDRH2:

(SEQ ID NO: 53)
CGTATTAAGAAAGAAAGTGAGGGTGGGACAATAGACTACGGTGCACCCGTGAAA
GGC (SEQ ID NO: 54)
RIKKESEGGTIDYGAPVKG

CDRH3:

(SEQ ID NO: 55)
ACCATCCCGAATCCTCAAATTGTGGTGGTGACTACTACTCCACATTCCCAT (SEQ ID NO: 56)
TIPNPQIVVVTTTPHSH

Lambda:

(SEQ ID NO: 57)
TCCTATGAGCTGACTCAGCCACCCTCAGTGTCAGTGGCCCCAGGAAAGACGGCC
AGGATTACCTGTGGGGGAAACAACATTGGAAGTAAAAATGTGCACTGGTACCAG
CAGAAGCCAGGCCAGGCCCCTGTGTTGGTCATCTATTATGATAGTGACCGGCCCT
CAGCCGATCCCTGAGCGATTCTCTGGCTCCAACTCTGGGAACACGGCCACCCTGAC
CATCAGCAGGGTCGAGGCCGGGGATGAGGCCGACTATTACTGTCAGGTGTGGGA
TAGTAGTAGTGATCATTGGGTG----TTCGGCGGAGGGACCAAGCTGGCCGTCCTAG (SEQ ID NO: 58)
SYELTQPPSVSVAPGKTARITCGGNNIGSKNVHWYQQKPGQAPVLVIYYDSDRPSAIPER
FSGSNSGNTATLTISRVEAGDEADYYCQVWDSSSDHWVFGGGTKLAVL

CDRL1:

(SEQ ID NO: 59)
GGGGGAAACAACATTGGAAGTAAAAATGTGCAC (SEQ ID NO: 60)
GGNNIGSKNVH

CDRL2:

(SEQ ID NO: 61)
TATGATAGTGACCGGCCCTCA (SEQ ID NO: 62)
YDSDRPS

CDRL3:

(SEQ ID NO: 63)
CAGGTGTGGGATAGTAGTAGTGATCATTGGGTG (SEQ ID NO: 64)
QVWDSSSDHWV

---

229-14-036-2C06

---

Heavy:

(SEQ ID NO: 65)
GAGGTGCAGCTGTTGGAGTCTGGGGGAGGCTCGGTACAGCCTGGGGGGTCCCTG
AGACTCTCCTGTGAAGCCTCTGGATTCACCTTTAAAAACTTCGCCATGACCTGGG
TCCGCCTGTCTCCAGGGAAGGGACTGGAGTGGGTCTCATCCATAAGCGGAGACG
GTGGAAGGACCTACTACTCAGAATCTGCTAAGGGACGGTTAATCATCTCCAGAG
ACAATGCCAACAACAGGCTGTTTCTACAAATGTACAGCCTGAGAGCCGACGACA
CGGCCATATATTTCTGTGCGAAAGATCGGGTGTCGCTGTGGTTCGGGGAGAACA
GGGGCTGGTTCGACTCCTGGGGCCAGGGAACCCTGGTCACCGTCTCCTCAGC (SEQ ID NO: 66)
EVQLLESGGGSVQPGGSLRLSCEASGFTFKNFAMTWVRLSPGKGLEWVSSISGDGGRTYY
SESAKGRLIISRDNANNRLFLQMYSLRADDTAIYFCAKDRVSLWFGENRGWFDSWGQGTL
VTVSS

CDRH1:

(SEQ ID NO: 67)
AACTTCGCCATGACC (SEQ ID NO: 68)
NFAMT

CDRH2:

(SEQ ID NO: 69)
TCCATAAGCGGAGACGGTGGAAGGACCTACTACTCAGAATCTGCTAAGGGA (SEQ ID NO: 70)
SISGDGGRTYYSESAKG

CDRH3:

(SEQ ID NO: 71)
GCGAAAGATCGGGTGTCGCTGTGGTTCGGGGAGAACAGGGGCTGGTTCGACTCC (SEQ ID NO: 72)
AKDRVSLWFGENRGWFDS

Lambda:

(SEQ ID NO: 73)
AATTTTATGCTGACTCAGCCCCACTCTGTGTCGGAGTCTCCGGGGAAGACGGTGA
CCATCTCCTGCACCGGCAGCAGTGGCAACATCGCCCGCTTCTCTGTGCAGTGGTA
TCAGCAACGCCCGGGCAGTGGCCCTATCACTGTGATCTATGAGAATAGTCAAAG
ACCCTCTGGGGTCCCTGATCGGTTCTCTGGCTCCATCGACACCTCCTCCAATTCTG
CCTCCCTCACCATCTCTGGACTGAAGATTGAAGACGAGGGAGACTACTACTGTCA
GTCTTATGATCTCAACAATTATTGGGTGTTCGGCGGAGGGACCAAACTGACCGTC
CTA (SEQ ID NO: 74)
NFMLTQPHSVSESPGKTVTISCTGSSGNIARFSVQWYQQRPGSGPITVIYENSQRPSGVP
DRFSGSIDTSSNSASLTISGLKIEDEGDYYCQSYDLNNYWVFGGGTKLTVL

CDRL1:

(SEQ ID NO: 75)
ACCGGCAGCAGTGGCAACATCGCCCGCTTCTCTGTGCAG (SEQ ID NO: 76)
TGSSGNIARFSVQ

CDRL2:

(SEQ ID NO: 77)
GAGAATAGTCAAAGACCCTCT (SEQ ID NO: 78)
ENSQRPS

CDRL3:

(SEQ ID NO: 79)
CAGTCTTATGATCTCAACAATTATTGGGTG (SEQ ID NO: 80)
QSYDLNNYWV

---

235-15-042-1E06

---

Heavy:

(SEQ ID NO: 81)
GAGGTGCAGCTGGTGGAGTCTGGGGGAGGCTTGGTGCAGCCTGGGGGGTCCCTA
AGACTCTCCTGTGCAGCCTCTGGATTCATCTTCAGAAGTTATGAAATGAACTGGG
TCCGCCAGGCTCCAGGGAAGGGCCTGGAGTGGATTTCATACATTAGTAGTAGTG
GTTCAACCATGTTCTACGCAGACTCTGTGAAGGGCCGATTCACCGTCTCCAGAGG
CAATGGCGAGAACTCACTGTATCTGCAAATGGACAGCCTGAGAGCCGAGGACAC
GGCTGTTTATTACTGTGCGAGAAATGGCCCAAAAGAAGGCAGCAGTTGGGACGA
CTGGTTCGACCCCTGGGGCCAGGGAACTCTGGTCACCGTCTCCTCAGC (SEQ ID NO: 82)
EVQLVESGGGLVQPGGSLRLSCAASGFIFRSYEMNWVRQAPGKGLEWISYISSSGSTMFY
ADSVKGRFTVSRGNGENSLYLQMDSLRAEDTAVYYCARNGPKEGSSWDDWFDPWGQGTLV
TVSS

CDRH1:

(SEQ ID NO: 83)
AGTTATGAAATGAAC (SEQ ID NO: 84)
SYEMN

CDRH2:

(SEQ ID NO: 85)
TACATTAGTAGTAGTGGTTCAACCATGTTCTACGCAGACTCTGTGAAGGGC (SEQ ID NO: 86)
YISSSGSTMFYADSVKG

CDRH3:

(SEQ ID NO: 87)
GCGAGAAATGGCCCAAAAGAAGGCAGCAGTTGGGACGACTGGTTCGACCCC (SEQ ID NO: 88)
ARNGPKEGSSWDDWFDP

Lambda:

(SEQ ID NO: 89)
TCCTATGAGCTGACTCAGGACCCTGCTGTGTCTGTGGCCTTGGGACAGACAATCA
GGATCACATGCCAAGGAGACACCCTCAGAAGCTATTCTGCAAGTTGGTACCAGC
AGAAGCCAGGACAGGCCCCTCTAGTTGTCATCTTTGGTGATAACAATAGGCCCTC
AGGGATCCCAGACCGATTCTCTGGCTCCAGGTTAGGAGACACAGCTTCCTTGACC
ATCACTGGGGCTCAGGCGGAAGATGAGGCTGACTATTACTGTAGTTCCCGGGAC
AGCAATAACAACCCCCTATATGTCTTCGGAACTGGGACCAAGGTCACCGTCC (SEQ ID NO: 90)
SYELTQDPAVSVALGQTIRITCQGDTLRSYSASWYQQKPGQAPLVVIFGDNNRPSGIPDR
FSGSRLGDTASLTITGAQAEDEADYYCSSRDSNNNPLYVFGTGTKVTV

CDRL1:

(SEQ ID NO: 91)
CAAGGAGACACCCTCAGAAGCTATTCTGCAAGT (SEQ ID NO: 92)
QGDTLRSYSAS

CDRL2:

GGTGATAACAATAGGCCCTCA (SEQ ID NO: 93)

GDNNRPS (SEQ ID NO: 94)

CDRL3:

AGTTCCCGGGACAGCAATAACAACCCCCTATATGTC (SEQ ID NO: 95)

SSRDSNNNPLYV (SEQ ID NO: 96)

---

1000-2E06

Heavy:

(SEQ ID NO: 97)
GTGCAGCTGGTGCAGTCTGGGCCTGAGGTGAAGAAGTCTGGGGCCTCAGTGAAG
ATTTCCTGCAAGGCTTCTGGATACACCTTCAGTAACTATGCTGTACATTGGGTGC
GCCAGGCCCCCGGACAAAGGCCTGAGTGGATGGGGTGGAGCAACGCTGGCAGTG
GTGCCACAAAATATTCACAGAATTTCCAGGGCAGACTCACCATTGTCAGGGACA
CATCCGCGAACACAGTCTTCATGGAGCTGAGCAGCCTGACATCTGAGGACACGG
CTGTATATTACTGTGCGAGACCAGTGAGAAACGGCATAGCACCTAGTGCTATCG
AATACTGGGGCCAGGGAACCCTGGTCACCGTCTCCTCAGC (SEQ ID NO: 98)
VQLVQSGPEVKKSGASVKISCKASGYTFSNYAVHWVRQAPGQRPEWMGWSNAGSG
ATKYSQNFQGRLTIVRDTSANTVFMELSSLTSEDTAVYYCARPVRNGIAPSAIEYWG
QGTLVTVSS

CDRH1:

AACTATGCTGTACAT (SEQ ID NO: 99)

NYAVH (SEQ ID NO: 100)

CDRH2:

TGGAGCAACGCTGGCAGTGGTGCCACAAAATATTCACAGAATTTCCAGGGC (SEQ ID NO: 101)

WSNAGSGATKYSQNFQG (SEQ ID NO: 102)

CDRH3:

GCGAGACCAGTGAGAAACGGCATAGCACCTAGTGCTATCGAATAC (SEQ ID NO: 103)

ARPVRNGIAPSAIEY (SEQ ID NO: 104)

Kappa:

(SEQ ID NO: 105)
GACATCGTGATGACCCAGTCTCCAGACTCCCTGGCTGTGTCTCTGGGCGAGAGGG
CCACCATCAACTGCAAGTCCAGCCAGAGTGTTTTTTACAGGTCCACCAATAAGAA
CTACTTAGCTTGGTACCAGCAGAAACCAGGACAGCCTCCTAAGTTGCTCATTCAC
TGGGCATCTACCCGGGAATCCGGGGTCCCTGACCGATTCAGTGGCAGCGGGTCT
GGGACAGATTTCACTCTCACCATCAGCAGCCTGCAGGCTGAAGATGTGGCAGTTT
ATTACTGTCAGCAATATTATAATACGATCACTTTCGGCCCTGGGACCAAAGTGGA
TATCAAAC (SEQ ID NO: 106)
DIVMTQSPDSLAVSLGERATINCKSSQSVFYRSTNKNYLAWYQQKPGQPPKLLIHWASTR
ESGVPDRFSGSGSGTDFTLTISSLQAEDVAVYYCQQYYNTITFGPGTKVDIK

CDRK1:

AAGTCCAGCCAGAGTGTTTTTTACAGGTCCACCAATAAGAACTACTTAGCT (SEQ ID NO: 107)

KSSQSVFYRSTNKNYLA (SEQ ID NO: 108)

-continued

CDRK2:
(SEQ ID NO: 109)
TGGGCATCTACCCGGGAATCC (SEQ ID NO: 110)
WASTRES

CDRK3:
(SEQ ID NO: 111)
CAGCAATATTATAATACGATCACT (SEQ ID NO: 112)
QQYYNTIT

---
294-16-009-A-1C02
---

Heavy:
(SEQ ID NO: 113)
CAGGTGCAGCTGCAGGAGTCGGGCCCAGGACTGGTGAAGCCTTCGGAGACCCTG
TCCCTCACCTGCACTGTCTCTGGTGGCTCCCTCAGTTGTGGTACTTACTACTGGGG
CTGGATCCGCCAGCCCCCAGGGAAGGATCTGGAGTGGCTTGGGAGTATCTATTGT
AGTGGAAACACCTACTACAACCCGTCCCTCAAGAGTCAAGTCACCATATCCGTG
GACACGTCCAAGAAAGAGTTCTCCCTGAAGCTGAGCTCTGTGACCGCCGCAGAC
ACGGCTGTGTATTACTGTGCGAGACATGCAGGACATCTTGCGCCTTTTGGAGTGG
ACCTAACTGATGGTTTTGATATCTGGGGCCGAGGGACAATGGTCACCGTCTCTTC
AGC (SEQ ID NO: 114)
QVQLQESGPGLVKPSETLSLTCTVSGGSLSCGTYYWGWIRQPPGKDLEWLGSIYCSGNTY
YNPSLKSQVTISVDTSKKEFSLKLSSVTAADTAVYYCARHAGHLAPFGVDLTDGFDIWGR
GTMVTVSS

CDRH1:
(SEQ ID NO: 115)
TGTGGTACTTACTACTGGGGC (SEQ ID NO: 116)
CGTYYWG

CDRH2:
(SEQ ID NO: 117)
AGTATCTATTGTAGTGGAAACACCTACTACAACCCGTCCCTCAAGAGT (SEQ ID NO: 118)
SIYCSGNTYYNPSLKS

CDRH3:
(SEQ ID NO: 119)
GCGAGACATGCAGGACATCTTGCGCCTTTTGGAGTGGACCTAACTGATGGTTTTG
ATATC (SEQ ID NO: 120)
ARHAGHLAPFGVDLTDGFDI

Lambda:
(SEQ ID NO: 121)
CAGTCTGTGCTGACGCAGCCGCCCTCAGTGTCCGGGGCCCCAGGACAGAGGGTC
ACCATCTCCTGCACTGGGAGTAGTTCCAACATTGGGGCAGGTTATGATGTACACT
GGTATCAGAAGCTTCCAGCAACAGCCCCCAAACTCCTCATCTATGGTAACAACA
ATCGACCCTCAGGGGTCCCTGACCGATTCTCTGGCTCCAAGTCTGGCACCTCAGC
CTCCCTGGCCATCACTGGGCTCCAGGCTGAGGATGAGGCTGATTATTACTGCCAG
TCCTATGACAACAGCCTGAGTGGTTTTGTGGTATTCGGCGGAGGGACCAAGCTGA
CCGTC (SEQ ID NO: 122)
QSVLTQPPSVSGAPGQRVTISCTGSSSNIGAGYDVHWYQKLPATAPKLLIYGNNNRPSGV
PDRFSGSKSGTSASLAITGLQAEDEADYYCQSYDNSLSGFVVFGGGTKLTV

CDRL1:
(SEQ ID NO: 123)
ACTGGGAGTAGTTCCAACATTGGGGCAGGTTATGATGTACAC (SEQ ID NO: 124)
TGSSSNIGAGYDVH

CDRL2:

(SEQ ID NO: 125)
GGTAACAACAATCGACCCTCA (SEQ ID NO: 126)
GNNNRPS

CDRL3:

(SEQ ID NO: 127)
CAGTCCTATGACAACAGCCTGAGTGGTTTTGTGGTA (SEQ ID NO: 128)
QSYDNSLSGFVV

294-16-009-A-1C06

Heavy:

(SEQ ID NO: 129)
GAGGTGCAGCTGGTGGAGTCTGGGGGAGGCCTGGTCAGGCCGGGGGGGTCCCTG
AGACTCTCCTGTGCAGCCTCTGGATTCACCTTCCCTGGCTATAGCATGAGCTGGA
TCCGCCAGGCTCCAGGGAAGGGGCTGGAGTGGGTCTCATCCATTAATGGTAATA
GTAATTCCATATACTACGGAGACTCAGTGAAGGGCCGGTTCACCATCGCCAGAG
ACAACGCCAAGAACTTACTATATCTGCAAATGAACAGCCTGAGGGCCGACGACA
CGGCTATTTATTACTGTGCGAGAGGCGGCGTAGCACTGGCTCAGGCTGACTACTG
GGGCCAGGGAGCCCTGGTCACCGTCTCCTCAGC (SEQ ID NO: 130)
EVQLVESGGGLVRPGGSLRLSCAASGFTFPGYSMSWIRQAPGKGLEWVSSINGNSNSIYY
GDSVKGRFTIARDNAKNLLYLQMNSLRADDTAIYYCARGGVALAQADYWGQGALVTVSS

CDRH1:

(SEQ ID NO: 131)
GGCTATAGCATGAGC (SEQ ID NO: 132)
GYSMS

CDRH2:

(SEQ ID NO: 133)
TCCATTAATGGTAATAGTAATTCCATATACTACGGAGACTCAGTGAAGGGC (SEQ ID NO: 134)
SINGNSNSIYYGDSVKG

CDRH3:

(SEQ ID NO: 135)
GCGAGAGGCGGCGTAGCACTGGCTCAGGCTGACTAC (SEQ ID NO: 136)
ARGGVALAQADY

Kappa:

(SEQ ID NO: 137)
GACATCCAGATGACCCAGTCTCCATCCTCCCTGTCTGCATCTGTGGGAGACAGAG
TCACCATCACTTGCCGGGCAAGTCAGAGCATTACCACCTTGTTAAATTGGTATCA
GCAGAAACCAGGGAAAGCCCCTAAACTCCTGATCGCTGCTGCATCCAGTTTGCA
AAGGGGGGTCCCATCGAGGTTCAGTGGCAGTGGATCTGGGACAGATTTCACTCT
CACCATCATGAGTCTGCAACCTGAAGATGTTGCGACTTACTACTGTCACCAGACT
TACAAAACCTTGTGGACGTTCGGCCAGGGGACCAAGGTGGAAATCAAAC (SEQ ID NO: 138)
DIQMTQSPSSLSASVGDRVTITCRASQSITTLLNWYQQKPGKAPKLLIAAASSLQRGVPS
RFSGSGSGTDFTLTIMSLQPEDVATYYCHQTYKTLWTFGQGTKVEIK

CDRK1:

(SEQ ID NO: 139)
CGGGCAAGTCAGAGCATTACCACCTTGTTAAAT (SEQ ID NO: 140)
RASQSITTLLN

CDRK2:

(SEQ ID NO: 141)
GCTGCATCCAGTTTGCAAAGG (SEQ ID NO: 142)
AASSLQR

-continued

| CDRK3: | |
|---|---|
| | (SEQ ID NO: 143) |
| CACCAGACTTACAAAACCTTGTGGACG | |
| | (SEQ ID NO: 144) |
| HQTYKTLWT | |

294-16-009-A-1D05

Heavy:
(SEQ ID NO: 145)
CAGGTGCAGCTGCAGGAGTCCGACTCAGGACTGGTCAGGCCCTCACAGACCCTG
TCACTCACCTGCGCTGTCTCTGGTGACTCCATCACCACTAGCACTTACTCCTGGA
ATTGGATCCGGCAGACACCAGGGAAGGGCCTGGAGTGGATTGGATATATCTATC
CTGCTGGGAGTCCCATCTACAATCCGTCCCTGAAGGGTCGAGTCACTATATCAAT
AGACAAGTCCAAAAACCAGTTCTCCCTGAACTTGAGCTCTGTGACCGCCGCGGA
CACGGCCATGTATTACTGTGCCACCCGGTCTAGACCGACAATTGGTATTGGTGCT
TACGATGTCTGGGGCCAAGGGACAATGGTCACCGTCTCTTCAGC (SEQ ID NO: 146)
QVQLQESDSGLVRPSQTLSLTCAVSGDSITTSTYSWNWIRQTPGKGLEWIGYIYPAGSPI
YNPSLKGRVTISIDKSKNQFSLNLSSVTAADTAMYYCATRSRPTIGIGAYDVWGQGTMVT
VSS

CDRH1:
(SEQ ID NO: 147)
ACTAGCACTTACTCCTGGAAT (SEQ ID NO: 148)
TSTYSWN

CDRH2:
(SEQ ID NO: 149)
TATATCTATCCTGCTGGGAGTCCCATCTACAATCCGTCCCTGAAGGGT (SEQ ID NO: 150)
YIYPAGSPIYNPSLKG

CDRH3:
(SEQ ID NO: 151)
GCCACCCGGTCTAGACCGACAATTGGTATTGGTGCTTACGATGTC (SEQ ID NO: 152)
ATRSRPTIGIGAYDV

Kappa:
(SEQ ID NO: 153)
GAAATAGTGATGACGCAGTCTCCAGCCGCCCTGTCTGTGTCTCTAGGGGGTAGAG
CCACCCTCTCCTGCAGGGCCACTGAGCGTGTTAACAGCGACTTAGCCTGGTACCA
GCAGAAACCTGGCCAGGCTCCCAGGCTCCTCATCTACGGTGCATCCACCAGGGC
CTCTAATGTCCCAGCCAGGTTCAGTGGCGGTGGGTCTGGAACAGACTTCATTCTC
ACCATCAGCAGCCTGCAGTCTGAAGATTTTGGAGTTTACTACTGTCAGCAGTATA
AGACCTGGCCTCGGACGTTCGGCCAAGGGACCAAGGTGGAAATCAAAC (SEQ ID NO: 154)
EIVMTQSPAALSVSLGGRATLSCRATERVNSDLAWYQQKPGQAPRLLIYGASTRASNVPA
RFSGGGSGTDFILTISSLQSEDFGVYYCQQYKTWPRTFGQGTKVEIK

CDRK1:
(SEQ ID NO: 155)
AGGGCCACTGAGCGTGTTAACAGCGACTTAGCC (SEQ ID NO: 156)
RATERVNSDLA

CDRK2:
(SEQ ID NO: 157)
GGTGCATCCACCAGGGCCTCT (SEQ ID NO: 158)
GASTRAS

CDRK3:
(SEQ ID NO: 159)
CAGCAGTATAAGACCTGGCCTCGGACG (SEQ ID NO: 160)
QQYKTWPRT

-continued

| 294-16-009-G-1F01 |
|---|

Heavy:
(SEQ ID NO: 161)
GAGGTGCAGCTGGTGGAGTCTGGGGGAGGCTTGGTCCAGCCTGGGGGGTCCCTG
AGACTCTCCTGTGCAGTCTCTGGATTCACCTTTACGAGCTATTGGATGAGCTGGG
TCCGCCAGACTCCAGGGAAGGGCTGGAGTGGGTGGCCAACATAAAGGAAGAT
GGAAGTCAGAAATACCATGTGGACTCTGTGAAGGGCCGATTCACCATCTCCAGA
GACAACGCCAAGAACTCACTATTTCTGCAAATGAACAGCCTGAGAGCCGAGGAC
ACGGCCGTGTATTACTGTGCGAGAGCTCATGAGTCGTTCTATTTCTCTGGTAGTA
CTACTTTTTACGCCGGACCGGGGGCTTTTGATATCTGGGGCCAAGGGACAATGGT
CACCGTCTCTTCAGC (SEQ ID NO: 162)
EVQLVESGGGLVQPGGSLRLSCAVSGFTFTSYWMSWVRQTPGKGLEWVANIKEDGSQKYH
VDSVKGRFTISRDNAKNSLFLQMNSLRAEDTAVYYCARAHESFYFSGSTTFYAGPGAFDI
WGQGTMVTVSS

CDRH1:
(SEQ ID NO: 163)
AGCTATTGGATGAGC (SEQ ID NO: 164)
SYWMS

CDRH2:
(SEQ ID NO: 165)
AACATAAAGGAAGATGGAAGTCAGAAATACCATGTGGACTCTGTGAAGGGC (SEQ ID NO: 166)
NIKEDGSQKYHVDSVKG

CDRH3:
(SEQ ID NO: 167)
GCGAGAGCTCATGAGTCGTTCTATTTCTCTGGTAGTACTACTTTTTACGCCGGACC
GGGGGCTTTTGATATC (SEQ ID NO: 168)
ARAHESFYFSGSTTFYAGPGAFDI

Lambda:
(SEQ ID NO: 169)
CAGTCTGCCCTGACTCAGCCTGCCTCCGTGTCTGGGTCTCCTGGACAGTCGATCA
CCATCTCCTGCACTGGAACCAGCAGTGATATTGGGAGTTATAAACTTGTCTCCTG
GTACCAACAGCACCCAGGCAAAGCCCCCCAACTCTTGATTTATGACGTCAGTAA
GCGGCCCTCAGGGGTTTCTAATCGCTTCTCTGGCTCCAAGTCTGGCAACACGGCC
TCCCTGACAATCTCTGGGCTCCAGGCTGAGGACGAGGCTGATTATTACTGCTGCT
CATATGCAGGTAGTAGCATTGTGCTTTTCGGCGGAGGGACCAAGCTGACCGTCCT
AG (SEQ ID NO: 170)
QSALTQPASVSGSPGQSITISCTGTSSDIGSYKLVSWYQQHPGKAPLLIYDVSKRPSGV
SNRFSGSKSGNTASLTISGLQAEDEADYYCCSYAGSSIVLFGGGTKLTVL

CDRL1:
(SEQ ID NO: 171)
ACTGGAACCAGCAGTGATATTGGGAGTTATAAACTTGTCTCC (SEQ ID NO: 172)
TGTSSDIGSYKLVS

CDRL2:
(SEQ ID NO: 173)
GACGTCAGTAAGCGGCCCTCA (SEQ ID NO: 174)
DVSKRPS

CDRL3:
(SEQ ID NO: 175)
TGCTCATATGCAGGTAGTAGCATTGTGCTT (SEQ ID NO: 176)
CSYAGSSIVL

-continued

| 296-16-003-G-2F04 |
|---|

Heavy:
(SEQ ID NO: 177)
GAGGTGCAGCTGGTGGAGTCTGGGGGAGGCCTGGTCAAGCCTGGGGGGTCCCTG
AGACTCTCCTGTGCAGCCTCTGGATTCACCTTCAGTACTTGTACCATGAACTGGG
TCCGCCAGGTTCCAGGGAAGGGGCTGGAGTGGGTCTCATCCATTAGTAGTACTA
GTACTTCCATATACTACGCAGACTCAGTGAAGGGCCGATTCACCATCTCCAGAGA
CAACGCCAACAACTCACTGTATCTGCAAATGAACAGCCTGAGAGCCGAGGACAC
GGCTGTATATTACTGTGCCGGGATAATTGGAAGTACGGCGGACTACTACTACATC
GACGTCTGGGGCAAAGGGACCACGGTCACCGTCTCCTCAG (SEQ ID NO: 178)
EVQLVESGGGLVKPGGSLRLSCAASGFTFSTCTMNWVRQVPGKGLEWVSSISSTSTSIYY
ADSVKGRFTISRDNANNSLYLQMNSLRAEDTAVYYCAGIIGSTADYYYIDVWGKGTTVTV
SS

CDRH1:
(SEQ ID NO: 179)
ACTTGTACCATGAAC (SEQ ID NO: 180)
TCTMN

CDRH2:
(SEQ ID NO: 181)
TCCATTAGTAGTACTAGTACTTCCATATACTACGCAGACTCAGTGAAGGGC (SEQ ID NO: 182)
SISSTSTSIYYADSVKG

CDRH3:
(SEQ ID NO: 183)
GCCGGGATAATTGGAAGTACGGCGGACTACTACTACATCGACGTC (SEQ ID NO: 184)
AGIIGSTADYYYIDV

Kappa:
(SEQ ID NO: 185)
GACATCCAGATGACCCAGTCTCCATCCTTCCTGTCTGCATCTGTAGGAGACAGAG
TCACCATCACTTGCCGGGCCAGTCAGGGCATTAGCAGTTATTTAGCCTGGTATCA
GCAAAAACCAGGGAAAGCCCCTAAGCTCCTGATCTATGCTGCTTCCACTTTGCAA
AGTGGGGTCCCATCAAGGTTCAGCGGCAGTGGATCTGGGACAGAGTTCACTCTC
ACAATCAGCAGCCTGCAGCCTGAAGATTTTGCAACTTACTACTGTCACCAGCTTA
ATAGTTACCGCTACACTTTCGGCGGAGGGACCAAGGTGGAAATCAAAC (SEQ ID NO: 186)
DIQMTQSPSFLSASVGDRVTITCRASQGISSYLAWYQQKPGKAPKLLIYAASTLQSGVPS
RFSGSGSGTEFTLTISSLQPEDFATYYCHQLNSYRYTFGGGTKVEIK

CDRK1:
(SEQ ID NO: 187)
CGGGCCAGTCAGGGCATTAGCAGTTATTTAGCC (SEQ ID NO: 188)
RASQGISSYLA

CDRK2:
(SEQ ID NO: 189)
GCTGCTTCCACTTTGCAAAGT (SEQ ID NO: 190)
AASTLQS

CDRK3:
(SEQ ID NO: 191)
CACCAGCTTAATAGTTACCGCTACACT (SEQ ID NO: 192)
HQLNSYRYT

| 300-16-005-G-2A04 |
|---|

Heavy:
(SEQ ID NO: 193)
CAGGTGCAGCTGCAGGAGTCGGGCCCAGGATTGGTGAAGTCTTCACAGACCCTG
TCCCTCACCTGCACTGTCTCTGGTGCCTCCATCAGCAGTGATTATTACTTCTGGAC

```
CTGGATCCGGCAGCCCGCCGGGAAGGGACTGGAATGGATTGGGTACATCTATAC
CAGTGGGAGCAGTAGTTACAATCCCTCCCTCAGGAGTCGAGTCAGCATATCAGT
AGACACGTCCAAGAACCACTTCTCCCTGAAGCTGAGCTCTGTGACCGCCACAGA
CACGGCCGTGTATTACTGTGCGAGAGAAGTGGCACGGGATACCAGTGGTTATTA
CTACTACTTTGATTCCTGGGGCCAGGGAACCCTGGTCACCGTCTCCTCAGC
```

(SEQ ID NO: 194)
```
QVQLQESGPGLVKSSQTLSLTCTVSGASISSDYYFWTWIRQPAGKGLEWIGYIYTSGSSS
YNPSLRSRVSISVDTSKNHFSLKLSSVTATDTAVYYCAREVARDTSGYYYYFDSWGQGTL
VTVSS
```

CDRH1:

(SEQ ID NO: 195)
```
AGTGATTATTACTTCTGGACC
```

(SEQ ID NO: 196)
```
SDYYFWT
```

CDRH2:

(SEQ ID NO: 197)
```
TACATCTATACCAGTGGGAGCAGTAGTTACAATCCCTCCCTCAGGAGT
```

(SEQ ID NO: 198)
```
YIYTSGSSSYNPSLRS
```

CDRH3:

(SEQ ID NO: 199)
```
GCGAGAGAAGTGGCACGGGATACCAGTGGTTATTACTACTACTTTGATTCC
```

(SEQ ID NO: 200)
```
AREVARDTSGYYYYFDS
```

Lambda:

(SEQ ID NO: 201)
```
CAGTCTGTGCTGACGCAGCCGCCCTCAGTGTCTGGGGCCCCAGGGCAGAGGGTC
ACCATCTCCTGCACTGGGAGCAGCTCCAACATCGGGGCAGGTTATGAAGTACAC
TGGTACCAGCAGTTTCCAGGAACAGCCCCCAAACTCCTCATCTATGCTGACTACA
ATCGGCCCTCAGGGGTCCCTGACCGATTCTCTGGCTCCAGGTCTGGCACCTCAGC
CTCCCTGGCCATCACTGGACTCCAGGCTGAGGATGAGGCTGATTATTACTGCCAG
TCCTATGACAACACTTTGAAACTCTTCGGAACTGGGACCAAGGTCACCGTCCT
```

(SEQ ID NO: 202)
```
QSVLTQPPSVSGAPGQRVTISCTGSSSNIGAGYEVHWYQQFPGTAPKLLIYADYNRPSGV
PDRFSGSRSGTSASLAITGLQAEDEADYYCQSYDNTLKLFGTGTKVTV
```

CDRL1:

(SEQ ID NO: 203)
```
ACTGGGAGCAGCTCCAACATCGGGGCAGGTTATGAAGTACAC
```

(SEQ ID NO: 204)
```
TGSSSNIGAGYEVH
```

CDRL2:

(SEQ ID NO: 205)
```
GCTGACTACAATCGGCCCTCA
```

(SEQ ID NO: 206)
```
ADYNRPS
```

CDRL3:

(SEQ ID NO: 207)
```
CAGTCCTATGACAACACTTTGAAACTC
```

(SEQ ID NO: 208)
```
QSYDNTLKL
```

---
229_1D02
---

Heavy:

(SEQ ID NO: 209)
```
EVQLVESGGGLVKPGGSLRLACAASGFSLSNYSMTWVRQAPGKELEWVSSIGSSSN
YIEYAGSVKGRFTISRDNAKNSLYLQMNSLRVEDTAVYYCARDFGYEFDFWGQGSL
VTVSS
```

CDRH1:

(SEQ ID NO: 210)
```
AASGFSLSNYSMT
```

```
CDRH2:
                                         (SEQ ID NO: 211)
SIGSSSNYIE

CDRH3:
                                         (SEQ ID NO: 212)
ARDFGYEFDF

Kappa:
                                         (SEQ ID NO: 213)
DIVMTQSPLSLPVTPGEPASISCRSSQSLLYSNGYNYLDWYLQKPGQSPQLLIYLGSN
RASGVPDRFSGSGSGTDFTLKISRVEAEDVGVYYCMQGLQTPTFGQGTKVEIK CDRL1:
                                         (SEQ ID NO: 214)
RSSQSLLYSNGYNYLD

CDRL2:
                                         (SEQ ID NO: 215)
YLGSNRAS

CDRL3:
                                         (SEQ ID NO: 216)
MQGLQTPT
```

229_1F06

```
Heavy:
                                         (SEQ ID NO: 217)
VQLVESGGGVVQPGRSLRLSCTSSGFHFNDYFMHWVRQAPGNGLEWVAVMGHDG
SNKDFSDSMKGRATISGDNSQNTLYLQINSLRVEDSAVYYCARASYFGELRADHYSF
AMDVWGQGTMVTVSS

CDRH1:
                                         (SEQ ID NO: 218)
TSSGFHFNDYFMH

CDRH2:
                                         (SEQ ID NO: 219)
VMGHDGSNKD

CDRH3:
                                         (SEQ ID NO: 220)
ARASYFGELRADHYSFAMDV

Kappa:
                                         (SEQ ID NO: 221)
EIVLTQSPGILSLSPGERGTLSCRASQSVSRSDLAWYQQKPGQAPRLLIYGASSRATGI
PDRFSGSGSGTDFTLTITRLEPEDFAVYYCQQYGTSPPYTFGQGTKVEIK

CDRL1:
                                         (SEQ ID NO: 222)
RASQSVSRSDLA

CDRL2:
                                         (SEQ ID NO: 223)
YGASSRAT

CDRL3:
                                         (SEQ ID NO: 224)
QQYGTSPPYT
```

229_2D03

```
Heavy:
                                         (SEQ ID NO: 225)
EVQLVESGGGLVQPGGSLRLSCAVSGLTVSGNYMSWVRQAPGKGLEWVSVLYING
KTFYADSVKGRFIISRDNAKNTLSLQMNSLRAEDTAVYFCTTNWDFYYYFNNWGQG
TLVTVSS

CDRH1:
                                         (SEQ ID NO: 226)
AVSGLTVSGNYMS

CDRH2:
                                         (SEQ ID NO: 227)
VLYTNGKTF
```

-continued

CDRH3:
(SEQ ID NO: 228)
TTNWDFYYYFNN

Kappa:
(SEQ ID NO: 229)
DIQMTQSPSTLSASVGDRVTITCRASQGITTWLAWYQQKPGKAPRLLIYQASSLESGV
PLRFSGSGSGTEFTLTISSLQPDDFATYYCQQYNNYPYTFGQGTKVEIK

CDRL1:
(SEQ ID NO: 230)
RASQGITTWLA

CDRL2:
(SEQ ID NO: 231)
YQASSLES

CDRL3:
(SEQ ID NO: 232)
QQYNNYPYT

REFERENCES

The following references, some of which are referenced above, are herein incorporated by reference in their entireties.

www.fludb.org/brc/home.spg?decorator=influenza. Influenza Research Database.

Abed, Y., Hardy, I., Li, Y., and Boivin, G. (2002). Divergent evolution of hemagglutinin and neuraminidase genes in recent influenza A:H3N2 viruses isolated in Canada. J Med Virol 67, 589-595.

Air, G. M. (2012). Influenza neuraminidase. Influenza Other Respir Viruses 6, 245-256.

Anderson, C. S., Ortega, S., Chaves, F. A., Clark, A. M., Yang, H., Topham, D. J., and DeDiego, M. L. (2017). Natural and directed antigenic drift of the H1 influenza virus hemagglutinin stalk domain. Sci Rep 7, 14614.

Andrews, S. F., Huang, Y., Kaur, K., Popova, L. I., Ho, I. Y., Pauli, N. T., Henry Dunand, C. J., Taylor, W. M., Lim, S., Huang, M., et al. (2015) Immune history profoundly affects broadly protective B cell responses to influenza. Sci Transl Med 7, 316ra192.

Angeletti, D., and Yewdell, J. W. (2017). Is It Possible to Develop a "Universal" Influenza Virus Vaccine? Outflanking Antibody Immunodominance on the Road to Universal Influenza Vaccination. Cold Spring Harb Perspect Biol.

Benton, D. J., Martin, S. R., Wharton, S. A., and McCauley, J. W. (2015). Biophysical measurement of the balance of influenza a hemagglutinin and neuraminidase activities. J Biol Chem 290, 6516-6521.

Brett, I. C., and Johansson, B. E. (2006). Variation in the divalent cation requirements of influenza A virus N1 neuraminidases. J Biochem 139, 439-447.

Clements, M. L., Betts, R. F., Tierney, E. L., and Murphy, B. R. (1986). Serum and nasal wash antibodies associated with resistance to experimental challenge with influenza A wild-type virus. J Clin Microbiol 24, 157-160.

Dharan, N.J., Gubareva, L. V., Meyer, J. J., Okomo-Adhiambo, M., McClinton, R. C., Marshall, S. A., St George, K., Epperson, S., Brammer, L., Klimov, A. I., et al. (2009). Infections with oseltamivir-resistant influenza A(H1N1) virus in the United States. JAMA 301, 1034-1041.

DiLillo, D. J., Palese, P., Wilson, P. C., and Ravetch, J. V. (2016). Broadly neutralizing anti-influenza antibodies require Fc receptor engagement for in vivo protection. The Journal of clinical investigation 126, 605-610.

Doyle, T. M., Hashem, A. M., Li, C., Van Domselaar, G., Larocque, L., Wang, J., Smith, D., Cyr, T., Farnsworth, A., He, R., et al. (2013). Universal anti-neuraminidase antibody inhibiting all influenza A subtypes. Antiviral Res 100, 567-574.

Eichelberger, M. C., and Wan, H. (2015). Influenza neuraminidase as a vaccine antigen. Curr Top Microbiol Immunol 386, 275-299.

Flannery, B. (2017). Interim estimates of 2016-17 seasonal influenza vaccine effectiveness— United States, February 2017. MMWR Morbidity and Mortality Weekly Report 66.

Genentech (2016). TAMIFLU (R) (oseltamivir phosphate) prescribing. https://wwwgenecom/download/pdf/tamiflu_prescribingpdf.

Henry Dunand, Carole J., Leon, Paul E., Huang, M., Choi, A., Chromikova, V., Ho, Irvin Y., Tan, Gene S., Cruz, J., Hirsh, A., Zheng, N.-Y., et al. (2016). Both Neutralizing and Non-Neutralizing Human H7N9 Influenza Vaccine-Induced Monoclonal Antibodies Confer Protection. Cell Host & Microbe 19, 800-813.

Henry Dunand, C. J., Leon, P. E., Kaur, K., Tan, G. S., Zheng, N.Y., Andrews, S., Huang, M., Qu, X., Huang, Y., Salgado-Ferrer, M., et al. (2015). Preexisting human antibodies neutralize recently emerged H7N9 influenza strains. The Journal of clinical investigation 125, 1255-1268.

Johansson, B. E., and Cox, M. M. (2011). Influenza viral neuraminidase: the forgotten antigen. Expert Rev Vaccines 10, 1683-1695.

Johansson, B. E., Moran, T. M., and Kilbourne, E. D. (1987). Antigen-presenting B cells and helper T cells cooperatively mediate intravirionic antigenic competition between influenza A virus surface glycoproteins. Proc Natl Acad Sci USA 84, 6869-6873.

Karron, R. A., and Collins, P. L. (2013). Parainfluenza viruses. In Fields Virology: Sixth Edition (Wolters Kluwer Health Adis (ESP)).

Krammer, F., and Palese, P. (2015). Advances in the development of influenza virus vaccines. Nat Rev Drug Discov 14, 167-182.

Lee, J., Boutz, D. R., Chromikova, V., Joyce, M. G., Vollmers, C., Leung, K., Horton, A. P., DeKosky, B. J., Lee, C. H., Lavinder, J. J., et al. (2016). Molecular-level analysis of the serum antibody repertoire in young adults before and after seasonal influenza vaccination. Nat Med 22, 1456-1464.

Li, G. M., Chiu, C., Wrammert, J., McCausland, M., Andrews, S. F., Zheng, N.Y., Lee, J. H., Huang, M., Qu, X., Edupuganti, S., et al. (2012). Pandemic H1N1 influenza vaccine induces a recall response in humans that favors broadly cross-reactive memory B cells. Proc Natl Acad Sci USA 109, 9047-9052.

Margine, I., Hai, R., Albrecht, R. A., Obermoser, G., Harrod, A. C., Banchereau, J., Palucka, K., Garcia-Sastre, A., Palese, P., Treanor, J. J., et al. (2013a). H3N2 influenza virus infection induces broadly reactive hemagglutinin stalk antibodies in humans and mice. Journal of virology 87, 4728-4737.

Margine, I., Palese, P., and Krammer, F. (2013b). Expression of functional recombinant hemagglutinin and neuraminidase proteins from the novel H7N9 influenza virus using the baculovirus expression system. J Vis Exp, e51112.

Matrosovich, M. N., Matrosovich, T. Y., Gray, T., Roberts, N. A., and Klenk, H.-D. (2004). Neuraminidase is important for the initiation of influenza virus infection in human airway epithelium. Journal of virology 78, 12665-12667.

Memoli, M. J., Shaw, P. A., Han, A., Czajkowski, L., Reed, S., Athota, R., Bristol, T., Fargis, S., Risos, K., Powers, J. H., et al. (2016). Evaluation of Antihemagglutinin and Antineuraminidase Antibodies as Correlates of Protection in an Influenza A/H1N1 Virus Healthy Human Challenge Model. MBio 7, e00417-00416.

Monto, A. S., and Kendal, A. P. (1973). Effect of neuraminidase antibody on Hong Kong influenza. Lancet 1, 623-625.

Monto, A. S., Petrie, J. G., Cross, R. T., Johnson, E., Liu, M., Zhong, W., Levine, M., Katz, J. M., and Ohmit, S. E. (2015). Antibody to Influenza Virus Neuraminidase: An Independent Correlate of Protection. J Infect Dis 212, 1191-1199.

Murphy, B. R., Kasel, J. A., and Chanock, R. M. (1972). Association of serum anti-neuraminidase antibody with resistance to influenza in man N Engl J Med 286, 1329-1332.

Nachbagauer, R., Choi, A., Hirsh, A., Margine, I., Iida, S., Barrera, A., Ferres, M., Albrecht, R. A., Garcia-Sastre, A., Bouvier, N. M., et al. (2017). Defining the antibody cross-reactome directed against the influenza virus surface glycoproteins. Nat Immunol 18, 464-473.

Neu, K. E., Henry Dunand, C. J., and Wilson, P. C. (2016). Heads, stalks and everything else: how can antibodies eradicate influenza as a human disease? Curr Opin Immunol 42, 48-55.

Nguyen, H. T., Sheu, T. G., Mishin, V. P., Klimov, A. I., and Gubareva, L. V. (2010). Assessment of pandemic and seasonal influenza A (H1N1) virus susceptibility to neuraminidase inhibitors in three enzyme activity inhibition assays. Antimicrob Agents Chemother 54, 3671-3677.

Nichol, K. L. (2008). Efficacy and effectiveness of influenza vaccination. Vaccine 26 Suppl 4, D17-22.

Palese, P., and Compans, R. (1976). Inhibition of influenza virus replication in tissue culture by 2-deoxy-2, 3-dehydro-N-trifluoroacetylneuraminic acid (FANA): mechanism of action. Journal of General Virology 33, 159-163.

Rajendran, M., Nachbagauer, R., Ermler, M. E., Bunduc, P., Amanat, F., Izikson, R., Cox, M., Palese, P., Eichelberger, M., and Krammer, F. (2017). Analysis of Anti-Influenza Virus Neuraminidase Antibodies in Children, Adults, and the Elderly by ELISA and Enzyme Inhibition: Evidence for Original Antigenic Sin. mBio 8, e02281-02216.

Sandbulte, M. R., Westgeest, K. B., Gao, J., Xu, X., Klimov, A. I., Russell, C. A., Burke, D. F., Smith, D. J., Fouchier, R. A., and Eichelberger, M. C. (2011). Discordant antigenic drift of neuraminidase and hemagglutinin in H1N1 and H3N2 influenza viruses. Proc Natl Acad Sci USA 108, 20748-20753.

Schulman, J. L., Khakpour, M., and Kilbourne, E. D. (1968). Protective effects of specific immunity to viral neuraminidase on influenza virus infection of mice. Journal of virology 2, 778-786.

Smith, K., Garman, L., Wrammert, J., Zheng, N.Y., Capra, J. D., Ahmed, R., and Wilson, P. C. (2009). Rapid generation of fully human monoclonal antibodies specific to a vaccinating antigen. Nature protocols 4, 372-384.

Sultana, I., Yang, K., Getie-Kebtie, M., Couzens, L., Markoff, L., Alterman, M., and Eichelberger, M. C. (2014). Stability of neuraminidase in inactivated influenza vaccines. Vaccine 32, 2225-2230.

Vavricka, C. J., Li, Q., Wu, Y., Qi, J., Wang, M., Liu, Y., Gao, F., Liu, J., Feng, E., He, J., et al. (2011). Structural and functional analysis of laninamivir and its octanoate prodrug reveals group specific mechanisms for influenza NA inhibition. PLoS pathogens 7, e1002249.

Wagner, R., Matrosovich, M., and Klenk, H. D. (2002). Functional balance between haemagglutinin and neuraminidase in influenza virus infections. Rev Med Virol 12, 159-166.

Wan, H., Gao, J., Xu, K., Chen, H., Couzens, L. K., Rivers, K. H., Easterbrook, J. D., Yang, K., Zhong, L., Rajabi, M., et al. (2013). Molecular basis for broad neuraminidase immunity: conserved epitopes in seasonal and pandemic H1N1 as well as H5N1 influenza viruses. Journal of virology 87, 9290-9300.

Wan, H., Yang, H., Shore, D. A., Garten, R. J., Couzens, L., Gao, J., Jiang, L., Carney, P. J., Villanueva, J., Stevens, J., et al. (2015). Structural characterization of a protective epitope spanning A(H1N1)pdm09 influenza virus neuraminidase monomers. Nat Commun 6, 6114.

Wardemann, H., Yurasov, S., Schaefer, A., Young, J. W., Meffre, E., and Nussenzweig, M. C. (2003). Predominant autoantibody production by early human B cell precursors. Science 301, 1374-1377.

Westgeest, K. B., Bestebroer, T. M., Spronken, M. I., Gao, J., Couzens, L., Osterhaus, A. D., Eichelberger, M., Fouchier, R. A., and de Graaf, M. (2015). Optimization of an enzyme-linked lectin assay suitable for rapid antigenic characterization of the neuraminidase of human influenza A(H3N2) viruses. J Virol Methods 217, 55-63.

WHO (2016). Influenza (seasonal) fact sheet. wwwwhoint/mediacentre/factsheets/fs211/en.

Wilson, J. R., Guo, Z., Reber, A., Kamal, R. P., Music, N., Gansebom, S., Bai, Y., Levine, M., Carney, P., and Tzeng, W.-P. (2016). An influenza A virus (H7N9) anti-neuraminidase monoclonal antibody with prophylactic and therapeutic activity in vivo. Antiviral research 135, 48-55.

Wohlbold, T. J., and Krammer, F. (2014). In the shadow of hemagglutinin: a growing interest in influenza viral neuraminidase and its role as a vaccine antigen. Viruses 6, 2465-2494.

Wohlbold, T. J., Nachbagauer, R., Xu, H., Tan, G. S., Hirsh, A., Brokstad, K. A., Cox, R. J., Palese, P., and Krammer, F. (2015). Vaccination with adjuvanted recombinant neuraminidase induces broad heterologous, but not heterosubtypic, cross-protection against influenza virus infection in mice. MBio 6, e02556.

Wohlbold, T. J., Podolsky, K. A., Chromikova, V., Kirkpatrick, E., Falconieri, V., Meade, P., Amanat, F., Tan, J., tenOever, B. R., Tan, G. S., et al. (2017). Broadly protective murine monoclonal antibodies against influenza B virus target highly conserved neuraminidase epitopes. Nat Microbiol.

Wrammert, J., Koutsonanos, D., Li, G. M., Edupuganti, S., Sui, J., Morrissey, M., McCausland, M., Skountzou, I., Hornig, M., Lipkin, W. I., et al. (2011). Broadly cross-reactive antibodies dominate the human B cell response against 2009 pandemic H1N1 influenza virus infection. The Journal of experimental medicine 208, 181-193.

Wrammert, J., Smith, K., Miller, J., Langley, W. A., Kokko, K., Larsen, C., Zheng, N.Y., Mays, I., Garman, L., Helms, C., et al. (2008). Rapid cloning of high-affinity human monoclonal antibodies against influenza virus. Nature 453, 667-671.

Wu, Y., Qin, G., Gao, F., Liu, Y., Vavricka, C. J., Qi, J., Jiang, H., Yu, K., and Gao, G. F. (2013). Induced opening of influenza virus neuraminidase N2 150-loop suggests an important role in inhibitor binding. Sci Rep 3, 1551.

---

SEQUENCE LISTING

```
Sequence total quantity: 232
SEQ ID NO: 1            moltype = DNA  length = 374
FEATURE                 Location/Qualifiers
source                  1..374
                        mol_type = genomic DNA
                        organism = Homo sapiens
SEQUENCE: 1
gaggtgcagc tggtggagtc tgggggaggc ttggttaagc ctggacaatc gcttagactc    60
tcctgtgcag cctctggatt cactttcact aatgcctgga tgagttgggt ccgccaggct   120
ccagggaagg ggctggagtg ggttggccgt atcaaaacca aaactgaagg cgagacagta   180
gactacgctg cacccgtgaa aggcagaatc accatctcaa gagatgactc aaagaacatg   240
gtgtatctgc aattgaagag cctgaaaatc gaggacgcag ccgtttacta ctgtaccaca   300
ggtcttacac gttcgagtct cggcggcttc gttgactact ggggcccggg aaccctggtc   360
accgtctcct cagc                                                     374

SEQ ID NO: 2            moltype = AA  length = 124
FEATURE                 Location/Qualifiers
source                  1..124
                        mol_type = protein
                        organism = Homo sapiens
SEQUENCE: 2
EVQLVESGGG LVKPGQSLRL SCAASGFTFT NAWMSWVRQA PGKGLEWVGR IKTKTEGETV     60
DYAAPVKGRI TISRDDSKNM VYLQLKSLKI EDAAVYYCTT GLTRSSLGGF VDYWGPGTLV   120
TVSS                                                                124

SEQ ID NO: 3            moltype = AA  length = 15
FEATURE                 Location/Qualifiers
source                  1..15
                        mol_type = protein
                        organism = Homo sapiens
SEQUENCE: 3
AATGCCTGGA TGAGT                                                     15

SEQ ID NO: 4            moltype = AA  length = 5
FEATURE                 Location/Qualifiers
source                  1..5
                        mol_type = protein
                        organism = Homo sapiens
SEQUENCE: 4
NAWMS                                                                 5

SEQ ID NO: 5            moltype = DNA  length = 57
FEATURE                 Location/Qualifiers
source                  1..57
                        mol_type = genomic DNA
                        organism = Homo sapiens
SEQUENCE: 5
cgtatcaaaa ccaaaactga aggcgagaca gtagactacg ctgcacccgt gaaaggc        57

SEQ ID NO: 6            moltype = AA  length = 19
FEATURE                 Location/Qualifiers
source                  1..19
                        mol_type = protein
                        organism = Homo sapiens
SEQUENCE: 6
RIKTKTEGET VDYAAPVKG                                                 19

SEQ ID NO: 7            moltype = DNA  length = 45
FEATURE                 Location/Qualifiers
source                  1..45
                        mol_type = genomic DNA
                        organism = Homo sapiens
```

```
SEQUENCE: 7
accacaggtc ttacacgttc gagtctcggc ggcttcgttg actac              45

SEQ ID NO: 8             moltype = AA   length = 15
FEATURE                  Location/Qualifiers
source                   1..15
                         mol_type = protein
                         organism = Homo sapiens
SEQUENCE: 8
TTGLTRSSLG GFVDY                                               15

SEQ ID NO: 9             moltype = DNA   length = 340
FEATURE                  Location/Qualifiers
source                   1..340
                         mol_type = genomic DNA
                         organism = Homo sapiens
SEQUENCE: 9
gacatcgtga tgacccagtc tccggactcc ctgactgtgt ctctgggcga gagggccacc   60
atcaactgca ggtccagcca gactgttttg tccagctcca acaatgagaa cttcttagct  120
tggtaccagc agaaatcagg acagcctcct aacctgctca tttactgggc atctacccgg  180
gcatccgggg tccctgaccg attcagtggc agcgggtctg ggacagattt cactctcact  240
atcagcagcc tgcagactga agatgtggca gtttattact gtctccaata tcttactact  300
cctcggacgt tcggccaagg gaccaaggtg gaaatcaaac                        340

SEQ ID NO: 10            moltype = AA   length = 113
FEATURE                  Location/Qualifiers
source                   1..113
                         mol_type = protein
                         organism = Homo sapiens
SEQUENCE: 10
DIVMTQSPDS LTVSLGERAT INCRSSQTVL SSSNNENFLA WYQQKSGQPP NLLIYWASTR   60
ASGVPDRFSG SGSGTDFTLT ISSLQTEDVA VYYCLQYLTT PRTFGQGTKV EIK         113

SEQ ID NO: 11            moltype = DNA   length = 51
FEATURE                  Location/Qualifiers
source                   1..51
                         mol_type = genomic DNA
                         organism = Homo sapiens
SEQUENCE: 11
aggtccagcc agactgtttt gtccagctcc aacaatgaga acttcttagc t           51

SEQ ID NO: 12            moltype = AA   length = 17
FEATURE                  Location/Qualifiers
source                   1..17
                         mol_type = protein
                         organism = Homo sapiens
SEQUENCE: 12
RSSQTVLSSS NNENFLA                                              17

SEQ ID NO: 13            moltype = DNA   length = 21
FEATURE                  Location/Qualifiers
source                   1..21
                         mol_type = genomic DNA
                         organism = Homo sapiens
SEQUENCE: 13
tgggcatcta cccgggcatc c                                         21

SEQ ID NO: 14            moltype = AA   length = 7
FEATURE                  Location/Qualifiers
source                   1..7
                         mol_type = protein
                         organism = Homo sapiens
SEQUENCE: 14
WASTRAS                                                         7

SEQ ID NO: 15            moltype = DNA   length = 27
FEATURE                  Location/Qualifiers
source                   1..27
                         mol_type = genomic DNA
                         organism = Homo sapiens
SEQUENCE: 15
ctccaatatc ttactactcc tcggacg                                   27

SEQ ID NO: 16            moltype = AA   length = 9
FEATURE                  Location/Qualifiers
source                   1..9
                         mol_type = protein
                         organism = Homo sapiens
SEQUENCE: 16
```

LQYLTTPRT 9

```
SEQ ID NO: 17          moltype = DNA   length = 380
FEATURE                Location/Qualifiers
source                 1..380
                       mol_type = genomic DNA
                       organism = Homo sapiens
SEQUENCE: 17
gtgcagctgg tggagtctgg gggaggcttg gtcaagcctg gagggtccct gagactctcc    60
tgtgcagcct ctggattcac cttcagtgac tactacatga gctggatccg ccaggctcca   120
gggaaggggc tggagtggat ttcatacatt agtagtagta gtacttacac agactacgca   180
gactctgtga agggccgatt caccgtctcc agagacaacg ccaagaactc attgtatcta   240
caaatgaaca acctgagagc cgaggacacg gccgtgtatt actgtgcgac cgtggccgac   300
accgcgtata gcagaggcag gccacaaatt acccactttg acaactgggg ccaggaaacc   360
ctggtcaccg tctcctcagc                                               380

SEQ ID NO: 18          moltype = AA    length = 126
FEATURE                Location/Qualifiers
source                 1..126
                       mol_type = protein
                       organism = Homo sapiens
SEQUENCE: 18
VQLVESGGGL VKPGGSLRLS CAASGFTFSD YYMSWIRQAP GKGLEWISYI SSSSTYTDYA    60
DSVKGRFTVS RDNAKNSLYL QMNNLRAEDT AVYYCATVAD TAYSRGRPQI THFDNWGQGT   120
LVTVSS                                                              126

SEQ ID NO: 19          moltype = DNA   length = 15
FEATURE                Location/Qualifiers
source                 1..15
                       mol_type = genomic DNA
                       organism = Homo sapiens
SEQUENCE: 19
gactactaca tgagc                                                     15

SEQ ID NO: 20          moltype = AA    length = 5
FEATURE                Location/Qualifiers
source                 1..5
                       mol_type = protein
                       organism = Homo sapiens
SEQUENCE: 20
DYYMS                                                                 5

SEQ ID NO: 21          moltype = DNA   length = 51
FEATURE                Location/Qualifiers
source                 1..51
                       mol_type = genomic DNA
                       organism = Homo sapiens
SEQUENCE: 21
tacattagta gtagtagtac ttacacagac tacgcagact ctgtgaaggg c              51

SEQ ID NO: 22          moltype = AA    length = 17
FEATURE                Location/Qualifiers
source                 1..17
                       mol_type = protein
                       organism = Homo sapiens
SEQUENCE: 22
YISSSSTYTD YADSVKG                                                   17

SEQ ID NO: 23          moltype = DNA   length = 60
FEATURE                Location/Qualifiers
source                 1..60
                       mol_type = genomic DNA
                       organism = Homo sapiens
SEQUENCE: 23
gcgaccgtgg ccgacaccgc gtatagcaga ggcaggccac aaattaccca ctttgacaac    60

SEQ ID NO: 24          moltype = AA    length = 20
FEATURE                Location/Qualifiers
source                 1..20
                       mol_type = protein
                       organism = Homo sapiens
SEQUENCE: 24
ATVADTAYSR GRPQITHFDN                                                20

SEQ ID NO: 25          moltype = DNA   length = 319
FEATURE                Location/Qualifiers
source                 1..319
                       mol_type = genomic DNA
                       organism = Homo sapiens
```

```
SEQUENCE: 25
tcctatgagc tgactcagcc accctcaatg tccgtgtccc caggacagac agccaccatc    60
acctgttttg gagataaatt gggggaaaag tatgcttact ggtatcagca gaagcctggc   120
cagtcccctc tactggtcat ctatcaagat accaagcggc cctcaggat ccctgagcgg    180
ttctctggct ccaactctgg gaacacagcc actctgacca tcagcgggac ccaggctatg   240
gatgaggctg actattactg tcagacgtgg gacagcaccc ttgtgttttt cggcggaggg   300
accaagctga ccgtcctag                                                319

SEQ ID NO: 26           moltype = AA   length = 106
FEATURE                 Location/Qualifiers
source                  1..106
                        mol_type = protein
                        organism = Homo sapiens
SEQUENCE: 26
SYELTQPPSM SVSPGQTATI TCFGDKLGEK YAYWYQQKPG QSPLLVIYQD TKRPSGIPER    60
FSGSNSGNTA TLTISGTQAM DEADYYCQTW DSTLVFFGGG TKLTVL                  106

SEQ ID NO: 27           moltype = DNA   length = 33
FEATURE                 Location/Qualifiers
source                  1..33
                        mol_type = genomic DNA
                        organism = Homo sapiens
SEQUENCE: 27
tttggagata aattgggga aaagtatgct tac                                  33

SEQ ID NO: 28           moltype = AA   length = 11
FEATURE                 Location/Qualifiers
source                  1..11
                        mol_type = protein
                        organism = Homo sapiens
SEQUENCE: 28
FGDKLGEKYA Y                                                         11

SEQ ID NO: 29           moltype = DNA   length = 21
FEATURE                 Location/Qualifiers
source                  1..21
                        mol_type = genomic DNA
                        organism = Homo sapiens
SEQUENCE: 29
caagatacca agcggccctc a                                              21

SEQ ID NO: 30           moltype = AA   length = 7
FEATURE                 Location/Qualifiers
source                  1..7
                        mol_type = protein
                        organism = Homo sapiens
SEQUENCE: 30
QDTKRPS                                                               7

SEQ ID NO: 31           moltype = DNA   length = 27
FEATURE                 Location/Qualifiers
source                  1..27
                        mol_type = genomic DNA
                        organism = Homo sapiens
SEQUENCE: 31
cagacgtggg acagcaccct tgtgttt                                        27

SEQ ID NO: 32           moltype = AA   length = 9
FEATURE                 Location/Qualifiers
source                  1..9
                        mol_type = protein
                        organism = Homo sapiens
SEQUENCE: 32
QTWDSTLVF                                                             9

SEQ ID NO: 33           moltype = DNA   length = 379
FEATURE                 Location/Qualifiers
source                  1..379
                        mol_type = genomic DNA
                        organism = Homo sapiens
SEQUENCE: 33
gtgcagctgg tggagtctgg gggaggcgtg gtccagcctg gggggtccct aagactctcc    60
tgtgcagtgt ctggactcac catcaatgac cttgtcatcc actgggtccg ccagcctcca   120
gacaagggc tggagtgggt ggcagttatg gggtatgatg gcgaaacaa agactatgca    180
gaatccgtga agggccgatt cagcatctc ggggacaatc cccagaacac actgtatctg    240
cagataaaca gcctgagagt cgaggacacg gctgtatatt actgtgcgag agcatcatac   300
ttcggggagt aagagacga gtactactcc ttcgccatgg acgtctgggg ccaagggacc    360
acggtcaccg tctcctcag                                                379
```

```
SEQ ID NO: 34              moltype = AA   length = 126
FEATURE                    Location/Qualifiers
source                     1..126
                           mol_type = protein
                           organism = Homo sapiens
SEQUENCE: 34
VQLVESGGGV VQPGGSLRLS CAVSGLTIND LVIHWVRQPP DKGLEWVAVM GYDGGNKDYA    60
ESVKGRFSIS GDNPQNTLYL QINSLRVEDT AVYYCARASY FGELRDEYYS FAMDVWGQGT   120
TVTVSS                                                              126

SEQ ID NO: 35              moltype = DNA   length = 15
FEATURE                    Location/Qualifiers
source                     1..15
                           mol_type = genomic DNA
                           organism = Homo sapiens
SEQUENCE: 35
gaccttgtca tccac                                                     15

SEQ ID NO: 36              moltype = AA   length = 5
FEATURE                    Location/Qualifiers
source                     1..5
                           mol_type = protein
                           organism = Homo sapiens
SEQUENCE: 36
DLVIH                                                                 5

SEQ ID NO: 37              moltype = DNA   length = 51
FEATURE                    Location/Qualifiers
source                     1..51
                           mol_type = genomic DNA
                           organism = Homo sapiens
SEQUENCE: 37
gttatggggt atgatggcgg aaacaaagac tatgcagaat ccgtgaaggg c              51

SEQ ID NO: 38              moltype = AA   length = 17
FEATURE                    Location/Qualifiers
source                     1..17
                           mol_type = protein
                           organism = Homo sapiens
SEQUENCE: 38
VMGYDGGNKD YAESVKG                                                   17

SEQ ID NO: 39              moltype = DNA   length = 60
FEATURE                    Location/Qualifiers
source                     1..60
                           mol_type = genomic DNA
                           organism = Homo sapiens
SEQUENCE: 39
gcgagagcat catacttcgg ggagttaaga gacgagtact actccttcgc catggacgtc    60

SEQ ID NO: 40              moltype = AA   length = 20
FEATURE                    Location/Qualifiers
source                     1..20
                           mol_type = protein
                           organism = Homo sapiens
SEQUENCE: 40
ARASYFGELR DEYYSFAMDV                                                20

SEQ ID NO: 41              moltype = DNA   length = 328
FEATURE                    Location/Qualifiers
source                     1..328
                           mol_type = genomic DNA
                           organism = Homo sapiens
SEQUENCE: 41
gaaattgtgt tgacgcagtc tccaggcacc ctgtctttgt ctccagggga aagaggcacc    60
ctctcctgca gggccagtca gagtgttagt aggagttact tagcctggta ccagcagaaa   120
cctggccagg ctcccaggct cctcatctat ggtgcatcca gcagggccac tggcatccca   180
gacaggttca gtggcagtgg gtctgggaca gacttcactc tcaccatcag cagactggag   240
cctgaagatt ttgcactgta ttactgtcag ctgtatggta cctcacctcc gtacactttt   300
ggccagggga ccaaggtgga aatcaaac                                      328

SEQ ID NO: 42              moltype = AA   length = 109
FEATURE                    Location/Qualifiers
source                     1..109
                           mol_type = protein
                           organism = Homo sapiens
SEQUENCE: 42
EIVLTQSPGT LSLSPGERGT LSCRASQSVS RSYLAWYQQK PGQAPRLLIY GASSRATGIP    60
DRFSGSGSGT DFTLTISRLE PEDFALYYCQ LYGTSPPYTF GQGTKVEIK               109
```

```
SEQ ID NO: 43            moltype = DNA  length = 36
FEATURE                  Location/Qualifiers
source                   1..36
                         mol_type = genomic DNA
                         organism = Homo sapiens
SEQUENCE: 43
agggccagtc agagtgttag taggagttac ttagcc                                36

SEQ ID NO: 44            moltype = AA  length = 12
FEATURE                  Location/Qualifiers
source                   1..12
                         mol_type = protein
                         organism = Homo sapiens
SEQUENCE: 44
RASQSVSRSY LA                                                          12

SEQ ID NO: 45            moltype = DNA  length = 21
FEATURE                  Location/Qualifiers
source                   1..21
                         mol_type = genomic DNA
                         organism = Homo sapiens
SEQUENCE: 45
ggtgcatcca gcagggccac t                                                21

SEQ ID NO: 46            moltype = AA  length = 7
FEATURE                  Location/Qualifiers
source                   1..7
                         mol_type = protein
                         organism = Homo sapiens
SEQUENCE: 46
GASSRAT                                                                7

SEQ ID NO: 47            moltype = DNA  length = 30
FEATURE                  Location/Qualifiers
source                   1..30
                         mol_type = genomic DNA
                         organism = Homo sapiens
SEQUENCE: 47
cagctgtatg gtacctcacc tccgtacact                                       30

SEQ ID NO: 48            moltype = AA  length = 10
FEATURE                  Location/Qualifiers
source                   1..10
                         mol_type = protein
                         organism = Homo sapiens
SEQUENCE: 48
QLYGTSPPYT                                                             10

SEQ ID NO: 49            moltype = DNA  length = 380
FEATURE                  Location/Qualifiers
source                   1..380
                         mol_type = genomic DNA
                         organism = Homo sapiens
SEQUENCE: 49
gaggtgcagc tggtggagtc tgggggaggc ttggtaaagc ctggggggtc ccttagactc      60
tcctgtgcag cctctggatt cactgtcagt aatgcctgga tgagctgggt ccgccaggct     120
ccaggaaagg ggctggagtg ggttggtcgt attaagaaag aaagtgaggg tgggacaata     180
gactacggtg cacccgtgaa aggcagattc accatctcaa gagatgaatc aaaaaacata     240
ttgtatctgc acatgaagag cctgataacc gatgacacag ccgtgtacta ctgtaccatc     300
ccgaatcctc aaattgtggt ggtgactact actccacatt cccattgggg ccaggaacc     360
ctggtcaccg tctcctcagc                                                 380

SEQ ID NO: 50            moltype = AA  length = 126
FEATURE                  Location/Qualifiers
source                   1..126
                         mol_type = protein
                         organism = Homo sapiens
SEQUENCE: 50
EVQLVESGGG LVKPGGSLRL SCAASGFTVS NAWMSWVRQA PGKGLEWVGR IKKESEGGTI      60
DYGAPVKGRF TISRDESKNI LYLHMKSLIT DDTAVYYCTI PNPQIVVVTT TPHSHWGQGT     120
LVTVSS                                                                126

SEQ ID NO: 51            moltype = DNA  length = 15
FEATURE                  Location/Qualifiers
source                   1..15
                         mol_type = genomic DNA
                         organism = Homo sapiens
SEQUENCE: 51
```

```
aatgcctgga tgagc                                                      15

SEQ ID NO: 52              moltype = AA  length = 5
FEATURE                    Location/Qualifiers
source                     1..5
                           mol_type = protein
                           organism = Homo sapiens
SEQUENCE: 52
NAWMS                                                                  5

SEQ ID NO: 53              moltype = DNA  length = 57
FEATURE                    Location/Qualifiers
source                     1..57
                           mol_type = genomic DNA
                           organism = Homo sapiens
SEQUENCE: 53
cgtattaaga aagaaagtga gggtgggaca atagactacg gtgcacccgt gaaaggc         57

SEQ ID NO: 54              moltype = AA  length = 19
FEATURE                    Location/Qualifiers
source                     1..19
                           mol_type = protein
                           organism = Homo sapiens
SEQUENCE: 54
RIKKESEGGT IDYGAPVKG                                                  19

SEQ ID NO: 55              moltype = DNA  length = 51
FEATURE                    Location/Qualifiers
source                     1..51
                           mol_type = genomic DNA
                           organism = Homo sapiens
SEQUENCE: 55
accatcccga atcctcaaat tgtggtggtg actactactc cacattccca t               51

SEQ ID NO: 56              moltype = AA  length = 17
FEATURE                    Location/Qualifiers
source                     1..17
                           mol_type = protein
                           organism = Homo sapiens
SEQUENCE: 56
TIPNPQIVVV TTTPHSH                                                    17

SEQ ID NO: 57              moltype = DNA  length = 325
FEATURE                    Location/Qualifiers
source                     1..325
                           mol_type = genomic DNA
                           organism = Homo sapiens
SEQUENCE: 57
tcctatgagc tgactcagcc accctcagtg tcagtggccc caggaaagac ggccaggatt     60
acctgtgggg gaaacaacat tggaagtaaa aatgtgcact ggtaccagca gaagccaggc    120
caggcccctg tgttggtcat ctattatgat agtgaccgat ccctgagcga cccctgagcga    180
ttctctggct ccaactctgg gaacacggcc accctgacca tcagcagggt cgaggccggg    240
gatgaggccg actattactg tcaggtgtgg gatagtagta gtgatcattg ggtgttcggc    300
ggagggacca agctggccgt cctag                                          325

SEQ ID NO: 58              moltype = AA  length = 108
FEATURE                    Location/Qualifiers
source                     1..108
                           mol_type = protein
                           organism = Homo sapiens
SEQUENCE: 58
SYELTQPPSV SVAPGKTARI TCGGNNIGSK NVHWYQQKPG QAPVLVIYYD SDRPSAIPER     60
FSGSNSGNTA TLTISRVEAG DEADYYCQVW DSSSDHWVFG GGTKLAVL                 108

SEQ ID NO: 59              moltype = DNA  length = 33
FEATURE                    Location/Qualifiers
source                     1..33
                           mol_type = genomic DNA
                           organism = Homo sapiens
SEQUENCE: 59
gggggaaaca acattggaag taaaaatgtg cac                                  33

SEQ ID NO: 60              moltype = AA  length = 11
FEATURE                    Location/Qualifiers
source                     1..11
                           mol_type = protein
                           organism = Homo sapiens
SEQUENCE: 60
GGNNIGSKNV H                                                          11
```

```
SEQ ID NO: 61            moltype = DNA  length = 21
FEATURE                  Location/Qualifiers
source                   1..21
                         mol_type = genomic DNA
                         organism = Homo sapiens
SEQUENCE: 61
tatgatagtg accggccctc a                                             21

SEQ ID NO: 62            moltype = AA  length = 7
FEATURE                  Location/Qualifiers
source                   1..7
                         mol_type = protein
                         organism = Homo sapiens
SEQUENCE: 62
YDSDRPS                                                             7

SEQ ID NO: 63            moltype = DNA  length = 33
FEATURE                  Location/Qualifiers
source                   1..33
                         mol_type = genomic DNA
                         organism = Homo sapiens
SEQUENCE: 63
caggtgtggg atagtagtag tgatcattgg gtg                                33

SEQ ID NO: 64            moltype = AA  length = 11
FEATURE                  Location/Qualifiers
source                   1..11
                         mol_type = protein
                         organism = Homo sapiens
SEQUENCE: 64
QVWDSSSDHW V                                                        11

SEQ ID NO: 65            moltype = DNA  length = 377
FEATURE                  Location/Qualifiers
source                   1..377
                         mol_type = genomic DNA
                         organism = Homo sapiens
SEQUENCE: 65
gaggtgcagc tgttggagtc tgggggaggc tcggtacagc ctgggggtc cctgagactc    60
tcctgtgaag cctctggatt caccttaaaa aacttcgcca tgacctgggt ccgcctgtct  120
ccagggaagg gactggagtg ggtctcatcc ataagcggag acgtggaag gacctactac   180
tcagaatctg ctaagggacg gttaatcatc tccagadaca atgccaacaa caggctgttt  240
ctacaaatgt acagcctgag agccgacgac acggccatat atttctgtgc gaaagatcgg  300
gtgtcgctgt ggttcgggga gaacaggggc tggttcgact cctgggggcca gggaaccctg  360
gtcaccgtct cctcagc                                                 377

SEQ ID NO: 66            moltype = AA  length = 125
FEATURE                  Location/Qualifiers
source                   1..125
                         mol_type = protein
                         organism = Homo sapiens
SEQUENCE: 66
EVQLLESGGG SVQPGGSLRL SCEASGFTFK NFAMTWVRLS PGKGLEWVSS ISGDGGRTYY   60
SESAKGRLII SRDNANNRLF LQMYSLRADD TAIYFCAKDR VSLWFGENRG WFDSWGQGTL  120
VTVSS                                                              125

SEQ ID NO: 67            moltype = DNA  length = 15
FEATURE                  Location/Qualifiers
source                   1..15
                         mol_type = genomic DNA
                         organism = Homo sapiens
SEQUENCE: 67
aacttcgcca tgacc                                                    15

SEQ ID NO: 68            moltype = AA  length = 5
FEATURE                  Location/Qualifiers
source                   1..5
                         mol_type = protein
                         organism = Homo sapiens
SEQUENCE: 68
NFAMT                                                               5

SEQ ID NO: 69            moltype = DNA  length = 51
FEATURE                  Location/Qualifiers
source                   1..51
                         mol_type = genomic DNA
                         organism = Homo sapiens
SEQUENCE: 69
```

-continued

```
tccataagcg gagacggtgg aaggacctac tactcagaat ctgctaaggg a           51

SEQ ID NO: 70           moltype = AA   length = 17
FEATURE                 Location/Qualifiers
source                  1..17
                        mol_type = protein
                        organism = Homo sapiens
SEQUENCE: 70
SISGDGGRTY YSESAKG                                                 17

SEQ ID NO: 71           moltype = DNA  length = 54
FEATURE                 Location/Qualifiers
source                  1..54
                        mol_type = genomic DNA
                        organism = Homo sapiens
SEQUENCE: 71
gcgaaagatc gggtgtcgct gtggttcggg gagaacaggg gctggttcga ctcc        54

SEQ ID NO: 72           moltype = AA   length = 18
FEATURE                 Location/Qualifiers
source                  1..18
                        mol_type = protein
                        organism = Homo sapiens
SEQUENCE: 72
AKDRVSLWFG ENRGWFDS                                                18

SEQ ID NO: 73           moltype = DNA  length = 333
FEATURE                 Location/Qualifiers
source                  1..333
                        mol_type = genomic DNA
                        organism = Homo sapiens
SEQUENCE: 73
aattttatgc tgactcagcc ccactctgtg tcggagtctc cggggaagac ggtgaccatc  60
tcctgcaccg gcagcagtgg caacatcgcc cgcttcctg tgcagtggta tcagcaacgc  120
ccggcagtg gccctatcac tgtgatctat gagaatagtc aaagaccctc tggggtccct  180
gatcggttct ctggctccat cgacacctcc tccaattctg cctccctcac catctctgga  240
ctgaagattg aagacgaggg agactactac tgtcagtctt atgatctcaa caattattgg  300
gtgttcggcg gagggaccaa actgaccgtc cta                               333

SEQ ID NO: 74           moltype = AA   length = 111
FEATURE                 Location/Qualifiers
source                  1..111
                        mol_type = protein
                        organism = Homo sapiens
SEQUENCE: 74
NFMLTQPHSV SESPGKTVTI SCTGSSGNIA RFSVQWYQQR PGSGPITVIY ENSQRPSGVP  60
DRFSGSIDTS SNSASLTISG LKIEDEGDYY CQSYDLNNYW VFGGGTKLTV L          111

SEQ ID NO: 75           moltype = DNA  length = 39
FEATURE                 Location/Qualifiers
source                  1..39
                        mol_type = genomic DNA
                        organism = Homo sapiens
SEQUENCE: 75
accggcagca gtggcaacat cgcccgcttc tctgtgcag                         39

SEQ ID NO: 76           moltype = AA   length = 13
FEATURE                 Location/Qualifiers
source                  1..13
                        mol_type = protein
                        organism = Homo sapiens
SEQUENCE: 76
TGSSGNIARF SVQ                                                     13

SEQ ID NO: 77           moltype = DNA  length = 21
FEATURE                 Location/Qualifiers
source                  1..21
                        mol_type = genomic DNA
                        organism = Homo sapiens
SEQUENCE: 77
gagaatagtc aaagaccctc t                                            21

SEQ ID NO: 78           moltype = AA   length = 7
FEATURE                 Location/Qualifiers
source                  1..7
                        mol_type = protein
                        organism = Homo sapiens
SEQUENCE: 78
ENSQRPS                                                            7
```

```
SEQ ID NO: 79            moltype = DNA   length = 30
FEATURE                  Location/Qualifiers
source                   1..30
                         mol_type = genomic DNA
                         organism = Homo sapiens
SEQUENCE: 79
cagtcttatg atctcaacaa ttattgggtg                                         30

SEQ ID NO: 80            moltype = AA   length = 10
FEATURE                  Location/Qualifiers
source                   1..10
                         mol_type = protein
                         organism = Homo sapiens
SEQUENCE: 80
QSYDLNNYWV                                                               10

SEQ ID NO: 81            moltype = DNA   length = 374
FEATURE                  Location/Qualifiers
source                   1..374
                         mol_type = genomic DNA
                         organism = Homo sapiens
SEQUENCE: 81
gaggtgcagc tggtggagtc tgggggaggc ttggtgcagc ctgggggtc cctaagactc         60
tcctgtgcag cctctggatt catcttcaga agttatgaaa tgaactgggt ccgccaggct       120
ccagggaagg gcctggagtg gatttcatac attagtagta gtggttcaac catgttctac       180
gcagactctg tgaagggccg attcaccgtc tccagaggca atggcagaaa ctcactgtat       240
ctgcaaatgg acagcctgag agccgaggac acggctgttt attactgtgc gagaaatggc       300
ccaaaagaag gcagcagttg ggacgactgg ttcgacccct ggggccaggg aactctggtc       360
accgtctcct cagc                                                         374

SEQ ID NO: 82            moltype = AA   length = 124
FEATURE                  Location/Qualifiers
source                   1..124
                         mol_type = protein
                         organism = Homo sapiens
SEQUENCE: 82
EVQLVESGGG LVQPGGSLRL SCAASGFIFR SYEMNWVRQA PGKGLEWISY ISSSGSTMFY         60
ADSVKGRFTV SRGNGENSLY LQMDSLRAED TAVYYCARNG PKEGSSWDDW FDPWGQGTLV       120
TVSS                                                                    124

SEQ ID NO: 83            moltype = AA   length = 15
FEATURE                  Location/Qualifiers
source                   1..15
                         mol_type = protein
                         organism = Homo sapiens
SEQUENCE: 83
AGTTATGAAA TGAAC                                                         15

SEQ ID NO: 84            moltype = AA   length = 5
FEATURE                  Location/Qualifiers
source                   1..5
                         mol_type = protein
                         organism = Homo sapiens
SEQUENCE: 84
SYEMN                                                                    5

SEQ ID NO: 85            moltype = DNA   length = 51
FEATURE                  Location/Qualifiers
source                   1..51
                         mol_type = genomic DNA
                         organism = Homo sapiens
SEQUENCE: 85
tacattagta gtagtggttc aaccatgttc tacgcagact ctgtgaaggg c                 51

SEQ ID NO: 86            moltype = AA   length = 17
FEATURE                  Location/Qualifiers
source                   1..17
                         mol_type = protein
                         organism = Homo sapiens
SEQUENCE: 86
YISSSGSTMF YADSVKG                                                       17

SEQ ID NO: 87            moltype = DNA   length = 51
FEATURE                  Location/Qualifiers
source                   1..51
                         mol_type = genomic DNA
                         organism = Homo sapiens
SEQUENCE: 87
```

```
gcgagaaatg gcccaaaaga aggcagcagt tgggacgact ggttcgaccc c              51

SEQ ID NO: 88          moltype = AA   length = 17
FEATURE                Location/Qualifiers
source                 1..17
                       mol_type = protein
                       organism = Homo sapiens
SEQUENCE: 88
ARNGPKEGSS WDDWFDP                                                    17

SEQ ID NO: 89          moltype = DNA  length = 325
FEATURE                Location/Qualifiers
source                 1..325
                       mol_type = genomic DNA
                       organism = Homo sapiens
SEQUENCE: 89
tcctatgagc tgactcagga ccctgctgtg tctgtggcct tgggacagac aatcaggatc     60
acatgccaag gagacaccct cagaagctat tctgcaagtt ggtaccagca gaagccagga    120
caggcccctc tagttgtcat ctttggtgat aacaataggc cctcaggat cccagaccga    180
ttctctggct ccaggttagg agacacagct tccttgacca tcactggggc tcaggcggaa    240
gatgaggctg actattactg tagttcccgg gacagcaata caaccccct atatgtcttc    300
ggaactggga ccaaggtcac cgtcc                                          325

SEQ ID NO: 90          moltype = AA   length = 108
FEATURE                Location/Qualifiers
source                 1..108
                       mol_type = protein
                       organism = Homo sapiens
SEQUENCE: 90
SYELTQDPAV SVALGQTIRI TCQGDTLRSY SASWYQQKPG QAPLVVIFGD NNRPSGIPDR     60
FSGSRLGDTA SLTITGAQAE DEADYYCSSR DSNNNPLYVF GTGTKVTV                 108

SEQ ID NO: 91          moltype = DNA  length = 33
FEATURE                Location/Qualifiers
source                 1..33
                       mol_type = genomic DNA
                       organism = Homo sapiens
SEQUENCE: 91
caaggagaca ccctcagaag ctattctgca agt                                  33

SEQ ID NO: 92          moltype = AA   length = 11
FEATURE                Location/Qualifiers
source                 1..11
                       mol_type = protein
                       organism = Homo sapiens
SEQUENCE: 92
QGDTLRSYSA S                                                          11

SEQ ID NO: 93          moltype = DNA  length = 21
FEATURE                Location/Qualifiers
source                 1..21
                       mol_type = genomic DNA
                       organism = Homo sapiens
SEQUENCE: 93
ggtgataaca ataggccctc a                                               21

SEQ ID NO: 94          moltype = AA   length = 7
FEATURE                Location/Qualifiers
source                 1..7
                       mol_type = protein
                       organism = Homo sapiens
SEQUENCE: 94
GDNNRPS                                                                7

SEQ ID NO: 95          moltype = DNA  length = 36
FEATURE                Location/Qualifiers
source                 1..36
                       mol_type = genomic DNA
                       organism = Homo sapiens
SEQUENCE: 95
agttcccggg acagcaataa caacccccta tatgtc                               36

SEQ ID NO: 96          moltype = AA   length = 12
FEATURE                Location/Qualifiers
source                 1..12
                       mol_type = protein
                       organism = Homo sapiens
SEQUENCE: 96
SSRDSNNNPL YV                                                         12
```

```
SEQ ID NO: 97            moltype = DNA  length = 365
FEATURE                  Location/Qualifiers
source                   1..365
                         mol_type = genomic DNA
                         organism = Homo sapiens
SEQUENCE: 97
gtgcagctgg tgcagtctgg gcctgaggtg aagaagtctg gggcctcagt gaagatttcc    60
tgcaaggctt ctggatacac cttcagtaac tatgctgtac attgggtgcg ccaggccccc   120
ggacaaaggc ctgagtggat ggggtggagc aacgctggca gtgctggcca aaaatattca   180
cagaatttcc agggcagact caccattgtc agggacacat ccgcgaacac agtcttcatg   240
gagctgagca gcctgacatc tgaggacacg gctgtatatt actgtgcgag accagtgaga   300
aacggcatag cacctagtgc tatcgaatac tggggccagg gaaccctggt caccgtctcc   360
tcagc                                                                365

SEQ ID NO: 98            moltype = AA  length = 121
FEATURE                  Location/Qualifiers
source                   1..121
                         mol_type = protein
                         organism = Homo sapiens
SEQUENCE: 98
VQLVQSGPEV KKSGASVKIS CKASGYTFSN YAVHWVRQAP GQRPEWMGWS NAGSGATKYS    60
QNFQGRLTIV RDTSANTVFM ELSSLTSEDT AVYYCARPVR NGIAPSAIEY WGQGTLVTVS   120
S                                                                    121

SEQ ID NO: 99            moltype = DNA  length = 15
FEATURE                  Location/Qualifiers
source                   1..15
                         mol_type = genomic DNA
                         organism = Homo sapiens
SEQUENCE: 99
aactatgctg tacat                                                      15

SEQ ID NO: 100           moltype = AA  length = 5
FEATURE                  Location/Qualifiers
source                   1..5
                         mol_type = protein
                         organism = Homo sapiens
SEQUENCE: 100
NYAVH                                                                  5

SEQ ID NO: 101           moltype = DNA  length = 51
FEATURE                  Location/Qualifiers
source                   1..51
                         mol_type = genomic DNA
                         organism = Homo sapiens
SEQUENCE: 101
tggagcaacg ctggcagtgg tgccacaaaa tattcacaga atttccaggg c              51

SEQ ID NO: 102           moltype = AA  length = 17
FEATURE                  Location/Qualifiers
source                   1..17
                         mol_type = protein
                         organism = Homo sapiens
SEQUENCE: 102
WSNAGSGATK YSQNFQG                                                    17

SEQ ID NO: 103           moltype = DNA  length = 45
FEATURE                  Location/Qualifiers
source                   1..45
                         mol_type = genomic DNA
                         organism = Homo sapiens
SEQUENCE: 103
gcgagaccag tgagaaacgg catagcacct agtgctatcg aatac                     45

SEQ ID NO: 104           moltype = AA  length = 15
FEATURE                  Location/Qualifiers
source                   1..15
                         mol_type = protein
                         organism = Homo sapiens
SEQUENCE: 104
ARPVRNGIAP SAIEY                                                      15

SEQ ID NO: 105           moltype = DNA  length = 337
FEATURE                  Location/Qualifiers
source                   1..337
                         mol_type = genomic DNA
                         organism = Homo sapiens
SEQUENCE: 105
```

```
gacatcgtga tgacccagtc tccagactcc ctggctgtgt ctctgggcga gagggccacc    60
atcaactgca agtccagcca gagtgttttt tacaggtcca ccaataagaa ctacttagct   120
tggtaccagc agaaaccagg acagcctcct aagttgctca ttcactgggc atctacccgg   180
gaatccgggg tccctgaccg attcagtggc agcgggtctg ggacagattt cactctcacc   240
atcagcagcc tgcaggctga agatgtggca gtttattact gtcagcaata ttataatacg   300
atcactttcg gccctgggac caaagtggat atcaaac                            337

SEQ ID NO: 106          moltype = AA   length = 112
FEATURE                 Location/Qualifiers
source                  1..112
                        mol_type = protein
                        organism = Homo sapiens
SEQUENCE: 106
DIVMTQSPDS LAVSLGERAT INCKSSQSVF YRSTNKNYLA WYQQKPGQPP KLLIHWASTR    60
ESGVPDRFSG SGSGTDFTLT ISSLQAEDVA VYYCQQYYNT ITFGPGTKVD IK           112

SEQ ID NO: 107          moltype = DNA   length = 51
FEATURE                 Location/Qualifiers
source                  1..51
                        mol_type = genomic DNA
                        organism = Homo sapiens
SEQUENCE: 107
aagtccagcc agagtgtttt ttacaggtcc accaataaga actacttagc t             51

SEQ ID NO: 108          moltype = AA   length = 17
FEATURE                 Location/Qualifiers
source                  1..17
                        mol_type = protein
                        organism = Homo sapiens
SEQUENCE: 108
KSSQSVFYRS TNKNYLA                                                    17

SEQ ID NO: 109          moltype = DNA   length = 21
FEATURE                 Location/Qualifiers
source                  1..21
                        mol_type = genomic DNA
                        organism = Homo sapiens
SEQUENCE: 109
tgggcatcta cccgggaatc c                                               21

SEQ ID NO: 110          moltype = AA   length = 7
FEATURE                 Location/Qualifiers
source                  1..7
                        mol_type = protein
                        organism = Homo sapiens
SEQUENCE: 110
WASTRES                                                                7

SEQ ID NO: 111          moltype = DNA   length = 24
FEATURE                 Location/Qualifiers
source                  1..24
                        mol_type = genomic DNA
                        organism = Homo sapiens
SEQUENCE: 111
cagcaatatt ataatacgat cact                                            24

SEQ ID NO: 112          moltype = AA   length = 8
FEATURE                 Location/Qualifiers
source                  1..8
                        mol_type = protein
                        organism = Homo sapiens
SEQUENCE: 112
QQYYNTIT                                                               8

SEQ ID NO: 113          moltype = DNA   length = 386
FEATURE                 Location/Qualifiers
source                  1..386
                        mol_type = genomic DNA
                        organism = Homo sapiens
SEQUENCE: 113
caggtgcagc tgcaggagtc gggcccagga ctggtgaagc cttcggagac cctgtccctc    60
acctgcactg tctctggtgg ctcccctcagt tgtggtactt actactgggg ctggatccgc   120
cagccccag ggaaggatct ggagtggctt gggagtatct attgtagtgg aaacacctac    180
tacaacccgt ccctcaagag tcaagtcacc atatccgtgg acacgtccaa gaaagagttc    240
tccctgaagc tgagctctgt gaccgccgca gacacggctg tgtattactg tgcgagacat    300
gcaggacatc ttgcgccttt tggagtggac ctaactgatg ttttgatat ctggggccga    360
gggacaatgg tcaccgtctc ttcagc                                         386

SEQ ID NO: 114          moltype = AA   length = 128
```

| FEATURE | Location/Qualifiers |
|---|---|
| source | 1..128<br>mol_type = protein<br>organism = Homo sapiens |

SEQUENCE: 114
```
QVQLQESGPG LVKPSETLSL TCTVSGGSLS CGTYYWGWIR QPPGKDLEWL GSIYCSGNTY   60
YNPSLKSQVT ISVDTSKKEF SLKLSSVTAA DTAVYYCARH AGHLAPFGVD LTDGFDIWGR  120
GTMVTVSS                                                           128
```

| SEQ ID NO: 115<br>FEATURE | moltype = DNA  length = 21 |
|---|---|
| source | 1..21<br>mol_type = genomic DNA<br>organism = Homo sapiens |

SEQUENCE: 115
```
tgtggtactt actactgggg c                                             21
```

| SEQ ID NO: 116<br>FEATURE | moltype = AA  length = 7 |
|---|---|
| source | 1..7<br>mol_type = protein<br>organism = Homo sapiens |

SEQUENCE: 116
```
CGTYYWG                                                              7
```

| SEQ ID NO: 117<br>FEATURE | moltype = DNA  length = 48 |
|---|---|
| source | 1..48<br>mol_type = genomic DNA<br>organism = Homo sapiens |

SEQUENCE: 117
```
agtatctatt gtagtggaaa cacctactac aacccgtccc tcaagagt                48
```

| SEQ ID NO: 118<br>FEATURE | moltype = AA  length = 16 |
|---|---|
| source | 1..16<br>mol_type = protein<br>organism = Homo sapiens |

SEQUENCE: 118
```
SIYCSGNTYY NPSLKS                                                   16
```

| SEQ ID NO: 119<br>FEATURE | moltype = DNA  length = 60 |
|---|---|
| source | 1..60<br>mol_type = genomic DNA<br>organism = Homo sapiens |

SEQUENCE: 119
```
gcgagacatg caggacatct tgcgcctttt ggagtggacc taactgatgg ttttgatatc   60
```

| SEQ ID NO: 120<br>FEATURE | moltype = AA  length = 20 |
|---|---|
| source | 1..20<br>mol_type = protein<br>organism = Homo sapiens |

SEQUENCE: 120
```
ARHAGHLAPF GVDLTDGFDI                                               20
```

| SEQ ID NO: 121<br>FEATURE | moltype = DNA  length = 333 |
|---|---|
| source | 1..333<br>mol_type = genomic DNA<br>organism = Homo sapiens |

SEQUENCE: 121
```
cagtctgtgc tgacgcagcc gcccctcagtg tccggggccc caggacagag ggtcaccatc   60
tcctgcactg ggagtagttc aacattgggg gcaggttatg atgtacactg gtatcagaag  120
cttccagcaa cagcccccaa actcctcatc tatggtaaca acaatcgacc ctcagggtc   180
cctgaccgat tctctggctc caagtctggc acctcagcct ccctggccat cactgggctc  240
caggctgagg atgaggctga ttattactgc cagtcctatg acaacagcct gagtggtttt  300
gtggtattcg gcggagggac caagctgacc gtc                                333
```

| SEQ ID NO: 122<br>FEATURE | moltype = AA  length = 111 |
|---|---|
| source | 1..111<br>mol_type = protein<br>organism = Homo sapiens |

SEQUENCE: 122
```
QSVLTQPPSV SGAPGQRVTI SCTGSSSNIG AGYDVHWYQK LPATAPKLLI YGNNNRPSGV   60
PDRFSGSKSG TSASLAITGL QAEDEADYYC QSYDNSLSGF VVFGGGTKLT V           111
```

```
SEQ ID NO: 123              moltype = DNA  length = 42
FEATURE                     Location/Qualifiers
source                      1..42
                            mol_type = genomic DNA
                            organism = Homo sapiens
SEQUENCE: 123
actgggagta gttccaacat tggggcaggt tatgatgtac ac                          42

SEQ ID NO: 124              moltype = AA   length = 14
FEATURE                     Location/Qualifiers
source                      1..14
                            mol_type = protein
                            organism = Homo sapiens
SEQUENCE: 124
TGSSSNIGAG YDVH                                                         14

SEQ ID NO: 125              moltype = DNA  length = 21
FEATURE                     Location/Qualifiers
source                      1..21
                            mol_type = genomic DNA
                            organism = Homo sapiens
SEQUENCE: 125
ggtaacaaca atcgaccctc a                                                 21

SEQ ID NO: 126              moltype = AA   length = 7
FEATURE                     Location/Qualifiers
source                      1..7
                            mol_type = protein
                            organism = Homo sapiens
SEQUENCE: 126
GNNNRPS                                                                  7

SEQ ID NO: 127              moltype = DNA  length = 36
FEATURE                     Location/Qualifiers
source                      1..36
                            mol_type = genomic DNA
                            organism = Homo sapiens
SEQUENCE: 127
cagtcctatg acaacagcct gagtggtttt gtggta                                 36

SEQ ID NO: 128              moltype = AA   length = 12
FEATURE                     Location/Qualifiers
source                      1..12
                            mol_type = protein
                            organism = Homo sapiens
SEQUENCE: 128
QSYDNSLSGF VV                                                           12

SEQ ID NO: 129              moltype = DNA  length = 359
FEATURE                     Location/Qualifiers
source                      1..359
                            mol_type = genomic DNA
                            organism = Homo sapiens
SEQUENCE: 129
gaggtgcagc tggtggagtc tgggggaggc ctggtcaggc cggggggtc  cctgagactc       60
tcctgtgcag cctctggatt caccttccct ggctatagca tgagctggat ccgccaggct      120
ccagggaagg ggctggagtg ggtctcatcc attaatggta atagtaattc catatactac      180
ggagactcag tgaagggccg gttcaccatc gccagagaca acgccaagaa cttactatat      240
ctgcaaatga acagcctgag ggccgacgac acggctattt attactgtgc gagaggcggc      300
gtagcactgg ctcaggctga ctactggggc cagggagccc tggtcaccgt ctcctcagc      359

SEQ ID NO: 130              moltype = AA   length = 119
FEATURE                     Location/Qualifiers
source                      1..119
                            mol_type = protein
                            organism = Homo sapiens
SEQUENCE: 130
EVQLVESGGG LVRPGGSLRL SCAASGFTFP GYSMSWIRQA PGKGLEWVSS INGNSNSIYY        60
GDSVKGRFTI ARDNAKNLLY LQMNSLRADD TAIYYCARGG VALAQADYWG QGALVTVSS       119

SEQ ID NO: 131              moltype = DNA  length = 15
FEATURE                     Location/Qualifiers
source                      1..15
                            mol_type = genomic DNA
                            organism = Homo sapiens
SEQUENCE: 131
ggctatagca tgagc                                                        15

SEQ ID NO: 132              moltype = AA   length = 5
```

```
FEATURE              Location/Qualifiers
source               1..5
                     mol_type = protein
                     organism = Homo sapiens
SEQUENCE: 132
GYSMS                                                                5

SEQ ID NO: 133       moltype = DNA  length = 51
FEATURE              Location/Qualifiers
source               1..51
                     mol_type = genomic DNA
                     organism = Homo sapiens
SEQUENCE: 133
tccattaatg gtaatagtaa ttccatatac tacggagact cagtgaaggg c              51

SEQ ID NO: 134       moltype = AA  length = 17
FEATURE              Location/Qualifiers
source               1..17
                     mol_type = protein
                     organism = Homo sapiens
SEQUENCE: 134
SINGNSNSIY YGDSVKG                                                   17

SEQ ID NO: 135       moltype = DNA  length = 36
FEATURE              Location/Qualifiers
source               1..36
                     mol_type = genomic DNA
                     organism = Homo sapiens
SEQUENCE: 135
gcgagaggcg gcgtagcact ggctcaggct gactac                              36

SEQ ID NO: 136       moltype = AA  length = 12
FEATURE              Location/Qualifiers
source               1..12
                     mol_type = protein
                     organism = Homo sapiens
SEQUENCE: 136
ARGGVALAQA DY                                                        12

SEQ ID NO: 137       moltype = DNA  length = 322
FEATURE              Location/Qualifiers
source               1..322
                     mol_type = genomic DNA
                     organism = Homo sapiens
SEQUENCE: 137
gacatccaga tgacccagtc tccatcctcc ctgtctgcat ctgtgggaga cagagtcacc    60
atcacttgcc gggcaagtca gagcattacc accttgttaa attggtatca gcagaaacca   120
gggaaagccc ctaaactcct gatcgctgct gcatccagtt tgcaaagggg ggtcccatcg   180
aggttcagtg gcagtggatc tgggacagat ttcactctca ccatcatgag tctgcaacct   240
gaagatgttg cgacttacta ctgtcaccag acttacaaaa ccttgtggac gttcggccag   300
gggaccaagg tggaaatcaa ac                                            322

SEQ ID NO: 138       moltype = AA  length = 107
FEATURE              Location/Qualifiers
source               1..107
                     mol_type = protein
                     organism = Homo sapiens
SEQUENCE: 138
DIQMTQSPSS LSASVGDRVT ITCRASQSIT TLLNWYQQKP GKAPKLLIAA ASSLQRGVPS    60
RFSGSGSGTD FTLTIMSLQP EDVATYYCHQ TYKTLWTFGQ GTKVEIK                 107

SEQ ID NO: 139       moltype = DNA  length = 33
FEATURE              Location/Qualifiers
source               1..33
                     mol_type = genomic DNA
                     organism = Homo sapiens
SEQUENCE: 139
cgggcaagtc agagcattac caccttgtta aat                                 33

SEQ ID NO: 140       moltype = AA  length = 11
FEATURE              Location/Qualifiers
source               1..11
                     mol_type = protein
                     organism = Homo sapiens
SEQUENCE: 140
RASQSITTLL N                                                         11

SEQ ID NO: 141       moltype = DNA  length = 21
FEATURE              Location/Qualifiers
```

```
source                  1..21
                        mol_type = genomic DNA
                        organism = Homo sapiens
SEQUENCE: 141
gctgcatcca gtttgcaaag g                                               21

SEQ ID NO: 142          moltype = AA   length = 7
FEATURE                 Location/Qualifiers
source                  1..7
                        mol_type = protein
                        organism = Homo sapiens
SEQUENCE: 142
AASSLQR                                                               7

SEQ ID NO: 143          moltype = DNA  length = 27
FEATURE                 Location/Qualifiers
source                  1..27
                        mol_type = genomic DNA
                        organism = Homo sapiens
SEQUENCE: 143
caccagactt acaaaacctt gtggacg                                         27

SEQ ID NO: 144          moltype = AA   length = 9
FEATURE                 Location/Qualifiers
source                  1..9
                        mol_type = protein
                        organism = Homo sapiens
SEQUENCE: 144
HQTYKTLWT                                                             9

SEQ ID NO: 145          moltype = DNA  length = 371
FEATURE                 Location/Qualifiers
source                  1..371
                        mol_type = genomic DNA
                        organism = Homo sapiens
SEQUENCE: 145
caggtgcagc tgcaggagtc cgactcagga ctggtcaggc cctcacagac cctgtcactc     60
acctgcgctg tctctggtga ctccatcacc actagcactt actcctggaa ttggatccgg    120
cagacaccag ggaagggcct ggagtggatt ggatatatct atcctgctgg gagtcccatc    180
tacaatccgt ccctgaaggg tcgagtcact atatcaatag acaagtccaa aaaccagttc    240
tccctgaact tgagctctgt gaccgccgcg gacacggcca tgtattactg tgccaccagg    300
tctagaccga caattggtat tggtgcttac gatgtctggg gccaagggac aatggtcacc    360
gtctcttcag c                                                         371

SEQ ID NO: 146          moltype = AA   length = 123
FEATURE                 Location/Qualifiers
source                  1..123
                        mol_type = protein
                        organism = Homo sapiens
SEQUENCE: 146
QVQLQESDSG LVRPSQTLSL TCAVSGDSIT TSTYSWNWIR QTPGKGLEWI GYIYPAGSPI     60
YNPSLKGRVT ISIDKSKNQF SLNLSSVTAA DTAMYYCATR SRPTIGIGAY DVWGQGTMVT    120
VSS                                                                  123

SEQ ID NO: 147          moltype = DNA  length = 21
FEATURE                 Location/Qualifiers
source                  1..21
                        mol_type = genomic DNA
                        organism = Homo sapiens
SEQUENCE: 147
actagcactt actcctggaa t                                               21

SEQ ID NO: 148          moltype = AA   length = 7
FEATURE                 Location/Qualifiers
source                  1..7
                        mol_type = protein
                        organism = Homo sapiens
SEQUENCE: 148
TSTYSWN                                                               7

SEQ ID NO: 149          moltype = DNA  length = 48
FEATURE                 Location/Qualifiers
source                  1..48
                        mol_type = genomic DNA
                        organism = Homo sapiens
SEQUENCE: 149
tatatctatc ctgctgggag tcccatctac aatccgtccc tgaagggt                  48

SEQ ID NO: 150          moltype = AA   length = 16
```

```
FEATURE                 Location/Qualifiers
source                  1..16
                        mol_type = protein
                        organism = Homo sapiens
SEQUENCE: 150
YIYPAGSPIY NPSLKG                                                           16

SEQ ID NO: 151          moltype = DNA   length = 45
FEATURE                 Location/Qualifiers
source                  1..45
                        mol_type = genomic DNA
                        organism = Homo sapiens
SEQUENCE: 151
gccacccggt ctagaccgac aattggtatt ggtgcttacg atgtc              45

SEQ ID NO: 152          moltype = AA    length = 15
FEATURE                 Location/Qualifiers
source                  1..15
                        mol_type = protein
                        organism = Homo sapiens
SEQUENCE: 152
ATRSRPTIGI GAYDV                                                            15

SEQ ID NO: 153          moltype = DNA   length = 322
FEATURE                 Location/Qualifiers
source                  1..322
                        mol_type = genomic DNA
                        organism = Homo sapiens
SEQUENCE: 153
gaaatagtga tgacgcagtc tccagccgcc ctgtctgtgt ctctaggggg tagagccacc    60
ctctcctgca gggccactga gcgtgttaac agcgacttag cctggtacca gcagaaacct   120
ggccaggctc ccaggctcct catctacggt gcatccacca gggcctctaa tgtcccagcc   180
aggttcagtg gcggtgggtc tggaacagac ttcattctca ccatcagcag cctgcagtct   240
gaagattttg gagtttacta ctgtcagcag tataagacct ggcctcggac gttcggccaa   300
gggaccaagg tggaaatcaa ac                                           322

SEQ ID NO: 154          moltype = AA    length = 107
FEATURE                 Location/Qualifiers
source                  1..107
                        mol_type = protein
                        organism = Homo sapiens
SEQUENCE: 154
EIVMTQSPAA LSVSLGGRAT LSCRATERVN SDLAWYQQKP GQAPRLLIYG ASTRASNVPA    60
RFSGGGSGTD FILTISSLQS EDFGVYYCQQ YKTWPRTFGQ GTKVEIK                 107

SEQ ID NO: 155          moltype = DNA   length = 33
FEATURE                 Location/Qualifiers
source                  1..33
                        mol_type = genomic DNA
                        organism = Homo sapiens
SEQUENCE: 155
agggccactg agcgtgttaa cagcgactta gcc                                        33

SEQ ID NO: 156          moltype = AA    length = 11
FEATURE                 Location/Qualifiers
source                  1..11
                        mol_type = protein
                        organism = Homo sapiens
SEQUENCE: 156
RATERVNSDL A                                                                11

SEQ ID NO: 157          moltype = DNA   length = 21
FEATURE                 Location/Qualifiers
source                  1..21
                        mol_type = genomic DNA
                        organism = Homo sapiens
SEQUENCE: 157
ggtgcatcca ccagggcctc t                                                     21

SEQ ID NO: 158          moltype = AA    length = 7
FEATURE                 Location/Qualifiers
source                  1..7
                        mol_type = protein
                        organism = Homo sapiens
SEQUENCE: 158
GASTRAS                                                                      7

SEQ ID NO: 159          moltype = DNA   length = 27
FEATURE                 Location/Qualifiers
```

```
source                  1..27
                        mol_type = genomic DNA
                        organism = Homo sapiens
SEQUENCE: 159
cagcagtata agacctggcc tcggacg                                            27

SEQ ID NO: 160          moltype = AA  length = 9
FEATURE                 Location/Qualifiers
source                  1..9
                        mol_type = protein
                        organism = Homo sapiens
SEQUENCE: 160
QQYKTWPRT                                                                 9

SEQ ID NO: 161          moltype = DNA  length = 395
FEATURE                 Location/Qualifiers
source                  1..395
                        mol_type = genomic DNA
                        organism = Homo sapiens
SEQUENCE: 161
gaggtgcagc tggtggagtc tgggggaggc ttggtccagc ctgggggtc cctgagactc         60
tcctgtgcag tctctggatt cacctttacg agctattgga tgagctgggt ccgccagact        120
ccagggaaag gctgagtg gtggccaac ataaaggaag atggaagtca gaaataccat           180
gtggactctg tgaagggccg attcaccatc tccagagaca cgccaagaa ctcactattt         240
ctgcaaatga acagcctgag agccgaggac acggccgtgt attactgtgc gagagctcat        300
gagtcgttct atttctctgg tagtactact ttttacgccg gaccggggc ttttgatatc         360
tggggccaag ggacaatggt caccgtctct tcagc                                   395

SEQ ID NO: 162          moltype = AA  length = 131
FEATURE                 Location/Qualifiers
source                  1..131
                        mol_type = protein
                        organism = Homo sapiens
SEQUENCE: 162
EVQLVESGGG LVQPGGSLRL SCAVSGFTFT SYWMSWVRQT PGKGLEWVAN IKEDGSQKYH         60
VDSVKGRFTI SRDNAKNSLF LQMNSLRAED TAVYYCARAH ESFYFSGSTT FYAGPGAFDI        120
WGQGTMVTVS S                                                             131

SEQ ID NO: 163          moltype = DNA  length = 15
FEATURE                 Location/Qualifiers
source                  1..15
                        mol_type = genomic DNA
                        organism = Homo sapiens
SEQUENCE: 163
agctattgga tgagc                                                         15

SEQ ID NO: 164          moltype = AA  length = 5
FEATURE                 Location/Qualifiers
source                  1..5
                        mol_type = protein
                        organism = Homo sapiens
SEQUENCE: 164
SYWMS                                                                     5

SEQ ID NO: 165          moltype = DNA  length = 51
FEATURE                 Location/Qualifiers
source                  1..51
                        mol_type = genomic DNA
                        organism = Homo sapiens
SEQUENCE: 165
aacataaagg aagatggaag tcagaaatac catgtggact ctgtgaaggg c                 51

SEQ ID NO: 166          moltype = AA  length = 17
FEATURE                 Location/Qualifiers
source                  1..17
                        mol_type = protein
                        organism = Homo sapiens
SEQUENCE: 166
NIKEDGSQKY HVDSVKG                                                       17

SEQ ID NO: 167          moltype = DNA  length = 72
FEATURE                 Location/Qualifiers
source                  1..72
                        mol_type = genomic DNA
                        organism = Homo sapiens
SEQUENCE: 167
gcgagagctc atgagtcgtt ctatttctct ggtagtacta cttttacgc cggaccgggg         60
gcttttgata tc                                                            72
```

-continued

```
SEQ ID NO: 168            moltype = AA   length = 24
FEATURE                   Location/Qualifiers
source                    1..24
                          mol_type = protein
                          organism = Homo sapiens
SEQUENCE: 168
ARAHESFYFS GSTTFYAGPG AFDI                                          24

SEQ ID NO: 169            moltype = DNA   length = 331
FEATURE                   Location/Qualifiers
source                    1..331
                          mol_type = genomic DNA
                          organism = Homo sapiens
SEQUENCE: 169
cagtctgccc tgactcagcc tgcctccgtg tctgggtctc ctggacagtc gatcaccatc    60
tcctgcactg gaaccagcag tgatattggg agttataaac ttgtctcctg gtaccaacag   120
cacccaggca aagcccccca actcttgatt tatgacgtca gtaagcggcc ctcagggggtt  180
tctaatcgct tctctggctc caagtctggc aacacggcct ccctgacaat ctctgggctc   240
caggctgagg acgaggctga ttattactgc tgctcatatg caggtagtag cattgtgctt   300
ttcggcggag ggaccaagct gaccgtccta g                                  331

SEQ ID NO: 170            moltype = AA   length = 110
FEATURE                   Location/Qualifiers
source                    1..110
                          mol_type = protein
                          organism = Homo sapiens
SEQUENCE: 170
QSALTQPASV SGSPGQSITI SCTGTSSDIG SYKLVSWYQQ HPGKAPQLLI YDVSKRPSGV    60
SNRFSGSKSG NTASLTISGL QAEDEADYYC CSYAGSSIVL FGGGTKLTVL              110

SEQ ID NO: 171            moltype = DNA   length = 42
FEATURE                   Location/Qualifiers
source                    1..42
                          mol_type = genomic DNA
                          organism = Homo sapiens
SEQUENCE: 171
actggaacca gcagtgatat tgggagttat aaacttgtct cc                       42

SEQ ID NO: 172            moltype = AA   length = 14
FEATURE                   Location/Qualifiers
source                    1..14
                          mol_type = protein
                          organism = Homo sapiens
SEQUENCE: 172
TGTSSDIGSY KLVS                                                      14

SEQ ID NO: 173            moltype = DNA   length = 21
FEATURE                   Location/Qualifiers
source                    1..21
                          mol_type = genomic DNA
                          organism = Homo sapiens
SEQUENCE: 173
gacgtcagta agcggccctc a                                              21

SEQ ID NO: 174            moltype = AA   length = 7
FEATURE                   Location/Qualifiers
source                    1..7
                          mol_type = protein
                          organism = Homo sapiens
SEQUENCE: 174
DVSKRPS                                                               7

SEQ ID NO: 175            moltype = DNA   length = 30
FEATURE                   Location/Qualifiers
source                    1..30
                          mol_type = genomic DNA
                          organism = Homo sapiens
SEQUENCE: 175
tgctcatatg caggtagtag cattgtgctt                                     30

SEQ ID NO: 176            moltype = AA   length = 10
FEATURE                   Location/Qualifiers
source                    1..10
                          mol_type = protein
                          organism = Homo sapiens
SEQUENCE: 176
CSYAGSSIVL                                                           10

SEQ ID NO: 177            moltype = DNA   length = 367
```

| FEATURE | Location/Qualifiers |
|---|---|
| source | 1..367<br>mol_type = genomic DNA<br>organism = Homo sapiens |

SEQUENCE: 177

```
gaggtgcagc tggtggagtc tgggggaggc ctggtcaagc ctgggggtc cctgagactc      60
tcctgtgcag cctctggatt caccttcagt acttgtacca tgaactgggt ccgccaggtt    120
ccagggaagg ggctggagtg ggtctcatcc attagtagta ctagtacttc catatactac    180
gcagactcag tgaagggccg attcaccatc tccagagaca acgccaacaa ctcactgtat    240
ctgcaaatga acagcctgag agccgaggac acggctgtat attactgtgc cgggataatt    300
ggaagtacgg cggactacta ctacatcgac gtctgggca aagggaccac ggtcaccgtc    360
tcctcag                                                               367
```

| SEQ ID NO: 178 | moltype = AA length = 122 |
|---|---|
| FEATURE | Location/Qualifiers |
| source | 1..122<br>mol_type = protein<br>organism = Homo sapiens |

SEQUENCE: 178

```
EVQLVESGGG LVKPGGSLRL SCAASGFTFS TCTMNWVRQV PGKGLEWVSS ISSTSTSIYY     60
ADSVKGRFTI SRDNANNSLY LQMNSLRAED TAVYYCAGII GSTADYYYID VWGKGTTVTV   120
SS                                                                    122
```

| SEQ ID NO: 179 | moltype = AA length = 15 |
|---|---|
| FEATURE | Location/Qualifiers |
| source | 1..15<br>mol_type = protein<br>organism = Homo sapiens |

SEQUENCE: 179

```
ACTTGTACCA TGAAC                                                       15
```

| SEQ ID NO: 180 | moltype = AA length = 5 |
|---|---|
| FEATURE | Location/Qualifiers |
| source | 1..5<br>mol_type = protein<br>organism = Homo sapiens |

SEQUENCE: 180

```
TCTMN                                                                   5
```

| SEQ ID NO: 181 | moltype = DNA length = 51 |
|---|---|
| FEATURE | Location/Qualifiers |
| source | 1..51<br>mol_type = genomic DNA<br>organism = Homo sapiens |

SEQUENCE: 181

```
tccattagta gtactagtac ttccatatac tacgcagact cagtgaaggg c                51
```

| SEQ ID NO: 182 | moltype = AA length = 17 |
|---|---|
| FEATURE | Location/Qualifiers |
| source | 1..17<br>mol_type = protein<br>organism = Homo sapiens |

SEQUENCE: 182

```
SISSTSTSIY YADSVKG                                                     17
```

| SEQ ID NO: 183 | moltype = DNA length = 45 |
|---|---|
| FEATURE | Location/Qualifiers |
| source | 1..45<br>mol_type = genomic DNA<br>organism = Homo sapiens |

SEQUENCE: 183

```
gccgggataa ttggaagtac ggcggactac tactacatcg acgtc                      45
```

| SEQ ID NO: 184 | moltype = AA length = 15 |
|---|---|
| FEATURE | Location/Qualifiers |
| source | 1..15<br>mol_type = protein<br>organism = Homo sapiens |

SEQUENCE: 184

```
AGIIGSTADY YYIDV                                                       15
```

| SEQ ID NO: 185 | moltype = DNA length = 322 |
|---|---|
| FEATURE | Location/Qualifiers |
| source | 1..322<br>mol_type = genomic DNA<br>organism = Homo sapiens |

SEQUENCE: 185

```
gacatccaga tgacccagtc tccatccttc ctgtctgcat ctgtaggaga cagagtcacc      60
atcacttgcc gggccagtca gggcattagc agttatttag cctggtatca gcaaaaacca    120
```

```
gggaaagccc ctaagctcct gatctatgct gcttccactt tgcaaagtgg ggtcccatca   180
aggttcagcg gcagtggatc tgggacagag ttcactctca caatcagcag cctgcagcct   240
gaagattttg caacttacta ctgtcaccag cttaatagtt accgctacac tttcggcgga   300
gggaccaagg tggaaatcaa ac                                            322

SEQ ID NO: 186          moltype = AA   length = 107
FEATURE                 Location/Qualifiers
source                  1..107
                        mol_type = protein
                        organism = Homo sapiens
SEQUENCE: 186
DIQMTQSPSF LSASVGDRVT ITCRASQGIS SYLAWYQQKP GKAPKLLIYA ASTLQSGVPS   60
RFSGSGSGTE FTLTISSLQP EDFATYYCHQ LNSYRYTFGG GTKVEIK                 107

SEQ ID NO: 187          moltype = DNA   length = 33
FEATURE                 Location/Qualifiers
source                  1..33
                        mol_type = genomic DNA
                        organism = Homo sapiens
SEQUENCE: 187
cgggccagtc agggcattag cagttattta gcc                                33

SEQ ID NO: 188          moltype = AA   length = 11
FEATURE                 Location/Qualifiers
source                  1..11
                        mol_type = protein
                        organism = Homo sapiens
SEQUENCE: 188
RASQGISSYL A                                                        11

SEQ ID NO: 189          moltype = DNA   length = 21
FEATURE                 Location/Qualifiers
source                  1..21
                        mol_type = genomic DNA
                        organism = Homo sapiens
SEQUENCE: 189
gctgcttcca ctttgcaaag t                                             21

SEQ ID NO: 190          moltype = AA   length = 7
FEATURE                 Location/Qualifiers
source                  1..7
                        mol_type = protein
                        organism = Homo sapiens
SEQUENCE: 190
AASTLQS                                                             7

SEQ ID NO: 191          moltype = DNA   length = 27
FEATURE                 Location/Qualifiers
source                  1..27
                        mol_type = genomic DNA
                        organism = Homo sapiens
SEQUENCE: 191
caccagctta atagttaccg ctacact                                       27

SEQ ID NO: 192          moltype = AA   length = 9
FEATURE                 Location/Qualifiers
source                  1..9
                        mol_type = protein
                        organism = Homo sapiens
SEQUENCE: 192
HQLNSYRYT                                                           9

SEQ ID NO: 193          moltype = DNA   length = 377
FEATURE                 Location/Qualifiers
source                  1..377
                        mol_type = genomic DNA
                        organism = Homo sapiens
SEQUENCE: 193
caggtgcagc tgcaggagtc gggcccagga ttggtgaagt cttcacagac cctgtccctc   60
acctgcactg tctctggtgc ctccatcagc agtgattatt acttctggac ctggatccgg   120
cagcccgccg gaagggact ggaatggatt ggtacatct ataccagtgg gagcagtagt    180
tacaatccct ccctcaggag tcgagtcagc atatcagtag acacgtccaa gaaccacttc   240
tccctgaagc tgagctctgt gaccgccaca gacacggccg tgtattactg tgcgagagaa   300
gtggcacggg ataccagtgg ttattactac tactttgatt cctggggcca gggaaccctg   360
gtcaccgtct cctcagc                                                  377

SEQ ID NO: 194          moltype = AA   length = 125
FEATURE                 Location/Qualifiers
source                  1..125
```

```
                        mol_type = protein
                        organism = Homo sapiens
SEQUENCE: 194
QVQLQESGPG LVKSSQTLSL TCTVSGASIS SDYYFWTWIR QPAGKGLEWI GYIYTSGSSS    60
YNPSLRSRVS ISVDTSKNHF SLKLSSVTAT DTAVYYCARE VARDTSGYYY YFDSWGQGTL   120
VTVSS                                                              125

SEQ ID NO: 195          moltype = DNA   length = 21
FEATURE                 Location/Qualifiers
source                  1..21
                        mol_type = genomic DNA
                        organism = Homo sapiens
SEQUENCE: 195
agtgattatt acttctggac c                                             21

SEQ ID NO: 196          moltype = AA    length = 7
FEATURE                 Location/Qualifiers
source                  1..7
                        mol_type = protein
                        organism = Homo sapiens
SEQUENCE: 196
SDYYFWT                                                              7

SEQ ID NO: 197          moltype = DNA   length = 48
FEATURE                 Location/Qualifiers
source                  1..48
                        mol_type = genomic DNA
                        organism = Homo sapiens
SEQUENCE: 197
tacatctata ccagtgggag cagtagttac aatccctccc tcaggagt                48

SEQ ID NO: 198          moltype = AA    length = 16
FEATURE                 Location/Qualifiers
source                  1..16
                        mol_type = protein
                        organism = Homo sapiens
SEQUENCE: 198
YIYTSGSSSY NPSLRS                                                   16

SEQ ID NO: 199          moltype = DNA   length = 51
FEATURE                 Location/Qualifiers
source                  1..51
                        mol_type = genomic DNA
                        organism = Homo sapiens
SEQUENCE: 199
gcgagagaag tggcacggga taccagtggt tattactact actttgattc c            51

SEQ ID NO: 200          moltype = AA    length = 17
FEATURE                 Location/Qualifiers
source                  1..17
                        mol_type = protein
                        organism = Homo sapiens
SEQUENCE: 200
AREVARDTSG YYYYFDS                                                  17

SEQ ID NO: 201          moltype = DNA   length = 326
FEATURE                 Location/Qualifiers
source                  1..326
                        mol_type = genomic DNA
                        organism = Homo sapiens
SEQUENCE: 201
cagtctgtgc tgacgcagcc gccctcagtg tctggggccc cagggcagag ggtcaccatc   60
tcctgcactg ggagcagctc caacatcggg gcaggttatg aagtacactg gtaccagcag  120
tttccaggaa cagcccccaa actcctcatc tatgctgact acaatcggcc ctcaggggtc  180
cctgaccgat tctctggctc caggtctggc acctcagcct ccctggccat cactggactc  240
caggctgagg atgaggctga ttattactgc cagtcctatg acaacacttt gaaactcttc  300
ggaactggga ccaaggtcac cgtcct                                       326

SEQ ID NO: 202          moltype = AA    length = 108
FEATURE                 Location/Qualifiers
source                  1..108
                        mol_type = protein
                        organism = Homo sapiens
SEQUENCE: 202
QSVLTQPPSV SGAPGQRVTI SCTGSSSNIG AGYEVHWYQQ FPGTAPKLLI YADYNRPSGV    60
PDRFSGSRSG TSASLAITGL QAEDEADYYC QSYDNTLKLF GTGTKVTV                108

SEQ ID NO: 203          moltype = DNA   length = 42
FEATURE                 Location/Qualifiers
```

-continued

```
source                       1..42
                             mol_type = genomic DNA
                             organism = Homo sapiens
SEQUENCE: 203
actgggagca gctccaacat cggggcaggt tatgaagtac ac                         42

SEQ ID NO: 204               moltype = AA  length = 14
FEATURE                      Location/Qualifiers
source                       1..14
                             mol_type = protein
                             organism = Homo sapiens
SEQUENCE: 204
TGSSSNIGAG YEVH                                                        14

SEQ ID NO: 205               moltype = DNA  length = 21
FEATURE                      Location/Qualifiers
source                       1..21
                             mol_type = genomic DNA
                             organism = Homo sapiens
SEQUENCE: 205
gctgactaca atcggccctc a                                                21

SEQ ID NO: 206               moltype = AA  length = 7
FEATURE                      Location/Qualifiers
source                       1..7
                             mol_type = protein
                             organism = Homo sapiens
SEQUENCE: 206
ADYNRPS                                                                 7

SEQ ID NO: 207               moltype = DNA  length = 27
FEATURE                      Location/Qualifiers
source                       1..27
                             mol_type = genomic DNA
                             organism = Homo sapiens
SEQUENCE: 207
cagtcctatg acaacacttt gaaactc                                          27

SEQ ID NO: 208               moltype = AA  length = 9
FEATURE                      Location/Qualifiers
source                       1..9
                             mol_type = protein
                             organism = Homo sapiens
SEQUENCE: 208
QSYDNTLKL                                                               9

SEQ ID NO: 209               moltype = AA  length = 117
FEATURE                      Location/Qualifiers
source                       1..117
                             mol_type = protein
                             organism = Homo sapiens
SEQUENCE: 209
EVQLVESGGG LVKPGGSLRL ACAASGFSLS NYSMTWVRQA PGKELEWVSS IGSSSNYIEY       60
AGSVKGRFTI SRDNAKNSLY LQMNSLRVED TAVYYCARDF GYEFDFWGQG SLVTVSS         117

SEQ ID NO: 210               moltype = AA  length = 13
FEATURE                      Location/Qualifiers
source                       1..13
                             mol_type = protein
                             organism = Homo sapiens
SEQUENCE: 210
AASGFSLSNY SMT                                                         13

SEQ ID NO: 211               moltype = AA  length = 10
FEATURE                      Location/Qualifiers
source                       1..10
                             mol_type = protein
                             organism = Homo sapiens
SEQUENCE: 211
SIGSSSNYIE                                                             10

SEQ ID NO: 212               moltype = AA  length = 10
FEATURE                      Location/Qualifiers
source                       1..10
                             mol_type = protein
                             organism = Homo sapiens
SEQUENCE: 212
ARDFGYEFDF                                                             10
```

-continued

```
SEQ ID NO: 213            moltype = AA   length = 111
FEATURE                   Location/Qualifiers
source                    1..111
                          mol_type = protein
                          organism = Homo sapiens
SEQUENCE: 213
DIVMTQSPLS LPVTPGEPAS ISCRSSQSLL YSNGYNYLDW YLQKPGQSPQ LLIYLGSNRA    60
SGVPDRFSGS GSGTDFTLKI SRVEAEDVGV YYCMQGLQTP TFGQGTKVEI K            111

SEQ ID NO: 214            moltype = AA   length = 16
FEATURE                   Location/Qualifiers
source                    1..16
                          mol_type = protein
                          organism = Homo sapiens
SEQUENCE: 214
RSSQSLLYSN GYNYLD                                                    16

SEQ ID NO: 215            moltype = AA   length = 8
FEATURE                   Location/Qualifiers
source                    1..8
                          mol_type = protein
                          organism = Homo sapiens
SEQUENCE: 215
YLGSNRAS                                                              8

SEQ ID NO: 216            moltype = AA   length = 8
FEATURE                   Location/Qualifiers
source                    1..8
                          mol_type = protein
                          organism = Homo sapiens
SEQUENCE: 216
MQGLQTPT                                                              8

SEQ ID NO: 217            moltype = AA   length = 126
FEATURE                   Location/Qualifiers
source                    1..126
                          mol_type = protein
                          organism = Homo sapiens
SEQUENCE: 217
VQLVESGGGV VQPGRSLRLS CTSSGFHFND YFMHWVRQAP GNGLEWVAVM GHDGSNKDFS    60
DSMKGRATIS GDNSQNTLYL QINSLRVEDS AVYYCARASY FGELRADHYS FAMDVWGQGT   120
MVTVSS                                                              126

SEQ ID NO: 218            moltype = AA   length = 13
FEATURE                   Location/Qualifiers
source                    1..13
                          mol_type = protein
                          organism = Homo sapiens
SEQUENCE: 218
TSSGFHFNDY FMH                                                       13

SEQ ID NO: 219            moltype = AA   length = 10
FEATURE                   Location/Qualifiers
source                    1..10
                          mol_type = protein
                          organism = Homo sapiens
SEQUENCE: 219
VMGHDGSNKD                                                           10

SEQ ID NO: 220            moltype = AA   length = 20
FEATURE                   Location/Qualifiers
source                    1..20
                          mol_type = protein
                          organism = Homo sapiens
SEQUENCE: 220
ARASYFGELR ADHYSFAMDV                                                20

SEQ ID NO: 221            moltype = AA   length = 109
FEATURE                   Location/Qualifiers
source                    1..109
                          mol_type = protein
                          organism = Homo sapiens
SEQUENCE: 221
EIVLTQSPGI LSLSPGERGT LSCRASQSVS RSDLAWYQQK PGQAPRLLIY GASSRATGIP    60
DRFSGSGSGT DFTLTITRLE PEDFAVYYCQ QYGTSPPYTF GQGTKVEIK               109

SEQ ID NO: 222            moltype = AA   length = 12
FEATURE                   Location/Qualifiers
source                    1..12
```

```
                           mol_type = protein
                           organism = Homo sapiens
SEQUENCE: 222
RASQSVSRSD LA                                                          12

SEQ ID NO: 223             moltype = AA   length = 8
FEATURE                    Location/Qualifiers
source                     1..8
                           mol_type = protein
                           organism = Homo sapiens
SEQUENCE: 223
YGASSRAT                                                               8

SEQ ID NO: 224             moltype = AA   length = 10
FEATURE                    Location/Qualifiers
source                     1..10
                           mol_type = protein
                           organism = Homo sapiens
SEQUENCE: 224
QQYGTSPPYT                                                             10

SEQ ID NO: 225             moltype = AA   length = 118
FEATURE                    Location/Qualifiers
source                     1..118
                           mol_type = protein
                           organism = Homo sapiens
SEQUENCE: 225
EVQLVESGGG LVQPGGSLRL SCAVSGLTVS GNYMSWVRQA PGKGLEWVSV LYTNGKTFYA       60
DSVKGRFIIS RDNAKNTLSL QMNSLRAEDT AVYFCTTNWD FYYYFNNWGQ GTLVTVSS         118

SEQ ID NO: 226             moltype = AA   length = 13
FEATURE                    Location/Qualifiers
source                     1..13
                           mol_type = protein
                           organism = Homo sapiens
SEQUENCE: 226
AVSGLTVSGN YMS                                                         13

SEQ ID NO: 227             moltype = AA   length = 9
FEATURE                    Location/Qualifiers
source                     1..9
                           mol_type = protein
                           organism = Homo sapiens
SEQUENCE: 227
VLYTNGKTF                                                              9

SEQ ID NO: 228             moltype = AA   length = 12
FEATURE                    Location/Qualifiers
source                     1..12
                           mol_type = protein
                           organism = Synthetic construct
SEQUENCE: 228
TTNWDFYYYF NN                                                          12

SEQ ID NO: 229             moltype = AA   length = 107
FEATURE                    Location/Qualifiers
source                     1..107
                           mol_type = protein
                           organism = Homo sapiens
SEQUENCE: 229
DIQMTQSPST LSASVGDRVT ITCRASQGIT TWLAWYQQKP GKAPRLLIYQ ASSLESGVPL       60
RFSGSGSGTE FTLTISSLQP DDFATYYCQQ YNNYPYTFGQ GTKVEIK                    107

SEQ ID NO: 230             moltype = AA   length = 11
FEATURE                    Location/Qualifiers
source                     1..11
                           mol_type = protein
                           organism = Homo sapiens
SEQUENCE: 230
RASQGITTWL A                                                           11

SEQ ID NO: 231             moltype = AA   length = 8
FEATURE                    Location/Qualifiers
source                     1..8
                           mol_type = protein
                           organism = Homo sapiens
SEQUENCE: 231
YQASSLES                                                               8
```

-continued

```
SEQ ID NO: 232          moltype = AA  length = 9
FEATURE                 Location/Qualifiers
source                  1..9
                        mol_type = protein
                        organism = Homo sapiens
SEQUENCE: 232
QQYNNYPYT                                                      9
```

The invention claimed is:

1. An antibody or antibody fragment comprising a heavy chain variable region comprising a CDR1 of SEQ ID NO: 4, a CDR2 of SEQ ID NO: 6 and CDR3 of SEQ ID NO: 8, and a light chain variable region comprising a CDR1 of SEQ ID NO: 12, a CDR2 of SEQ ID NO: 14 and CDR3 of SEQ ID NO: 16 wherein the antibody or antibody fragment is capable of binding to influenza neuraminidase (NA) protein.

2. The antibody or antibody fragment of claim 1, wherein the heavy chain variable region and the light chain variable region comprise first and second polypeptides.

3. The binding agent of claim 2, wherein the antibody or antibody fragment is a monoclonal antibody.

4. The antibody or antibody fragment of claim 2, wherein the binding agent is an antibody fragment.

5. The antibody or antibody fragment of claim 1, wherein the heavy chain variable region and the light chain variable region comprise a single polypeptide chain.

6. A polynucleotide or polynucleotides encoding an antibody or antibody fragment of claim 1.

7. A pharmaceutical preparation comprising an antibody or antibody fragment of claim 1.

8. A method comprising administering a therapeutic dose of the pharmaceutical preparation of claim 7 to a subject.

9. The method of claim 8, wherein said binding agent is co-administered with one or more additional therapeutic agents.

10. The antibody or antibody fragment of claim 1, comprising a heavy chain variable region of SEQ ID NO: 1 and a light chain variable region of SEQ ID NO: 9.

* * * * *